(12) United States Patent
Baum et al.

(10) Patent No.: US 8,609,936 B2
(45) Date of Patent: Dec. 17, 2013

(54) **HEMIPTERAN-AND COLEOPTERAN ACTIVE TOXIN PROTEINS FROM *BACILLUS THURINGIENSIS***

(75) Inventors: James Baum, Webster Groves, MO (US); Stanislaw Flasinski, Chesterfield, MO (US); Gregory R. Heck, Crystal Lake Park, MO (US); Stephen R. Penn, Chesterfield, MO (US); Uma Rao Sukuru, St. Charles, MO (US); Xiaohong Shi, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 722 days.

(21) Appl. No.: 12/109,122

(22) Filed: Apr. 24, 2008

(65) Prior Publication Data

US 2008/0295207 A1    Nov. 27, 2008

Related U.S. Application Data

(60) Provisional application No. 60/914,364, filed on Apr. 27, 2007.

(51) Int. Cl.
| | | |
|---|---|---|
| *A01H 5/00* | (2006.01) | |
| *A01H 5/10* | (2006.01) | |
| *C12N 15/82* | (2006.01) | |
| *C12N 15/32* | (2006.01) | |

(52) U.S. Cl.
USPC ................ 800/302; 536/23.71; 424/93.2

(58) Field of Classification Search
None
See application file for complete search history.

(56) References Cited

U.S. PATENT DOCUMENTS

| | | | |
|---|---|---|---|
| 5,723,440 | A | 3/1998 | Stockhoff et al. |
| 5,885,963 | A | 3/1999 | Stockhoff et al. |
| 5,942,658 | A * | 8/1999 | Donovan et al. ............. 800/279 |
| 2006/0021087 | A1 | 1/2006 | Baum et al. |
| 2006/0242732 | A1 | 10/2006 | Carozzi et al. |
| 2010/0064394 | A1 * | 3/2010 | Baum et al. ................... 800/301 |

FOREIGN PATENT DOCUMENTS

| | | |
|---|---|---|
| WO | 9314205 | 7/1993 |
| WO | 96/39843 A1 | 12/1996 |
| WO | 01/71042 A2 | 9/2001 |
| WO | 2005/110068 A2 | 11/2005 |
| WO | 2006/107761 A2 | 10/2006 |
| WO | 2007027776 | 3/2007 |

OTHER PUBLICATIONS

Huang et al (2007, J. Invert. Pathol. 95:175-180.*
New England Biolabs, Random Primer 12, Jun. 2004, http://web.archive.org/web/20040619083054/http://www.neb.com/nebecomm/products/productS1255.asp, 1 page.
New England Biolabs, Random Primer 24, Jun. 2004, http://web.archive.org/web/20040618195247/http://www.neb.com/nebecomm/products/productS1256.asp, 1 page.
EMBL Accession DQ836184, *Bacillus thuringiensis* strain F14-1 Cry51Aa1 (cry51Aa1) gene,complete CDs, http://srs.ebi.ac.uk/srsbin/cgi-bin/wgetz?-e+[EMBL:DQ836184]+-newId, created Aug. 1, 2007, 2 pages.
Huang, Da-Fang, et al., Microbial control and biotechnology research on *Bacillus thuringiensis* in China, Journal of Invertebrate Pathology, Mar. 31, 2007, pp. 175-180, vol. 95 No. 3.
International Search Report and Written Opinion dated Nov. 24, 2008 for PCT/US2008/005542 filed Apr. 25, 2008.
Baum, James A., et al., Binary Toxins from *Bacillus thuringiensis* Active against the Western Corn Rootworm, *Diabrotica virgifera virgifera* LeConte, Applied and Environmental Microbiology, Aug. 2004, pp. 4889-4898, vol. 70 No. 8.
Chan, Siew Wee, et al., Unusual Amino Acid Determinants of Host Range in the Mtx2 Family of Mosquitocidal Toxins, The Journal of Biological Chemistry, Jun. 14, 1996, pp. 14183-14187, vol. 271 No. 24.
Liu, Jian-Wei, et al., New Gene from Nine *Bacillus sphaericus* Strains Encoding Highly Conserved 35.8-Kilodalton Mosquitocidal Toxins, Applied and Environmental Microbiology, Jun. 1996, pp. 2174-2176, vol. 62 No. 6.
Wellman-Desbiens, Elisabeth, et al., Development of a *Bacillus thuringiensis*-Based Assay on *Lygus hesperus*, Journal of Economic Entomology, Oct. 2005, pp. 1469-1479, vol. 98 No. 5.
Thanabalu, Thirumaran, et al., A *Bacillus sphaericus* Gene Encoding a Novel Type of Mosquitocidal Toxin of 31.8 kDa, Gene, 1996, pp. 85-89, vol. 170 No. 1.
Crickmore, N. et al., Revision of the Nomenclature for the *Bacillus thuringiensis* Pesticidal Crystal Proteins, Microbiology and Molecular Biology Review, Sep. 1998, pp. 807-813, vol. 62 No. 3.
NCBI Accession No. D0836184, *Bacillus thuringiensis* strain F14-1 Cry51Aa1 (cry51Aa1) gene, obtained Oct. 1, 2010 from http://www.ncbi.nlm.nih.gov/nuccore/112253718, 1 page.
Revision history for NCBI Accession DQ836184, *Bacillus thuringiensis* strain F14-1 Cry51Aa1(cry51Aa1) gene, obtained on Oct. 1, 2010 from http://www.ncbi.nlm.nih.gov/sviewer/girevhist.cgi?val=DQ836184.1&log$=seqview, 1 page.
NCBI Sample GenBank Record obtained Oct. 1, 2010 from http://www.ncbi.nlm.nih.gov/Sitemap/samplerecord.html, 17 pages.
Correspondence from NCBI dated Sep. 24, 2010 re Date of First Public Release for DQ836184, 2 pages.
Extended European Search Report for EP Application 08754143.9 dated Oct. 6, 2010, 6 pages.
Hofte, Herman et al, Insecticidal Crystal Proteins of *Bacillus thuringiensis*, Microbiological Reviews, Jun. 1989, pp. 242-255, vol. 53 No. 2, American Society for Microbiology.
EBI Accession No. GSP: ABB68459, "*Drosophila melanogaster* Polypeptide SEQ ID No. 32169. Dyderpskrp Rgkptagtag Rkisprkpgr Veerrsnfned Rplgrrrsek Erttpssald", XP 002600478, Mar. 2002, Database Geneseq.

* cited by examiner

*Primary Examiner* — Anne Kubelik

(74) *Attorney, Agent, or Firm* — Thompson Coburn LLP; J. Wendy Davis

(57) ABSTRACT

A novel *Bacillus thuringiensis* crystal protein exhibiting insect inhibitory activity is disclosed. Growth of *Lygus* insects is significantly inhibited by providing the novel crystal protein in *Lygus* insect diet. Polynucleotides encoding the crystal protein, transgenic plants and microorganisms that contain the polynucleotides, isolated peptides derived from the crystal protein, and antibodies directed against the crystal protein are also provided. Methods of using the crystal protein and polynucleotides encoding the crystal protein to control Hemipteran insects are also disclosed.

17 Claims, 6 Drawing Sheets

Figure 1.

```
Matrix: EBLOSUM62
Gap_penalty: 10.0
Extend_penalty: 0.5
Identity:      96/376 (25.5%)

Cry15Aa1      1 MAIMN--DIAQDAARAWDIIAGPFIRPGTTPTNRQLFNYQIGNIEVEPGN    48
                |||::  .:..:|...|    ||....|....:  |.|.|...::....
TIC807        1 MAILDLKSLVLNAINYW----GPKNNNGIQGGD---FGYPISEKQIDTSI    43

Cry15Aa1     49 LNFS---VVP---------ELDFSVSQDLFNNTSVQQSQTASFNESRTET    86
                :.|:    ::|         |..|:.:|.|.|||.:||||||.||.:..|.|
TIC807       44 ITFTHPRLIPYDLTIPQNLETIFTTTQVLTNNTDLQQSQTVSFAKKTTTT    93

Cry15Aa1     87 TSTAVTHGVKSGVTVSASAKFNAKILVKSI-----EQTITTTVSTEYNFS   131
                |||:.|:|...|..:|.:.:....:.:..|      :.:.|....:...:|.|
TIC807       94 TSTSTTNGWTEGGKISDTLEEKVSVSIPFIGEGGGKNSTTIEANFAHNSS   143

Cry15Aa1    132 STTTRTNTVTRGWSIAQPVLVPPHSRVTATLQIYKGDFTVPVLL-----S   176
                :||.:...:....|:|:|||||||..:|.|||.|...|:||:|..|    |
TIC807      144 TTTFQQASTDIEWNISQPVLVPPSKQVVATLVIMGGNFTIPMDLMTTIDS   193

Cry15Aa1    177 LRVYGQTG-----TLAGNPS------FPSLYAATYENTLLGRIREHIAPP   215
                ...|....      |....:|.     |.|.|.|.::.|.                |
TIC807      194 TEHYSHYSGYPILTWISSPDNSYSGPFMSWYFANWPNL-----------P   232

Cry15Aa1    216 ALFRASNAYISNGVQAIWRGTATTRVSQGLYSVVRIDERPLAGYSGETRT   265
                :.|...:    .|.|  .:.:|:..:|||.|:||.|:.||.|:...........:|
TIC807      233 SGFGPLNS--DNTV--TYTGSVVSQVSAGVYATVRFDQYDIHNLRTIEKT   278

Cry15Aa1    266 YYL-PVTLSNSSQILTPGSLGSEIPIINPVPNASCKKENSPIIIHHDREK   314
                :|.  ..||.|      |.:|.|.|....|    ..|||..:
TIC807      279 WYARHATLHN----------GKKISINNVTEMA----PTSPIKTN      309

Cry15Aa1    315 HRERDYDKEHICHDQAEKYERDYDKE        340

TIC807      310                                    309
```

Figure 6

```
TIC807      ---MAILDLKSLVLNAINYWGPKNNNGIQGGDFGYPISEKQIDTSIITFTHPRLIPYDLT
Cry51Aa1    MIFLAILDLKSLVLNAINYWGPKNNNGIQGGDFGYPISEKQIDTSIITSTHPRLIPHDLT
               :***********************************************  ******:***

TIC807      IPQNLETIFTTTQVLTNNTDLQQSQTVSFAKKTTTTTSTSTTNGWTEGGKISDTLEEKVS
Cry51Aa1    IPQNLETIFTTTQVLTNNTDLQQSQTVSFAKKTTTTTSTSTTNGWTEGGKISDTLEEKVS
            ************************************************************

TIC807      VSIPFIGEGGGKNSTTIEANFAHNSSTTTFQQASTDIEWNISQPVLVPPSKQVVATLVIM
Cry51Aa1    VSIPFIGEGGGKNSTTIEANFAHNSSTTTFQQASTDIEWNISQPVLVPPRKQVVATLVIM
            *************************************************.*********

TIC807      GGNFTIPMDLMTTIDSTEHYSHYSGYPILTWISSPDNSYSGPFMSWYFANWPNLPSGFGP
Cry51Aa1    GGNFTIPMDLMTTIDSTEHYS---GYPILTWISSPDNSYNGPFMSWYFANWPNLPSGFGP
            *********************   *************** ********************

TIC807      LNSDNTVTYTGSVVSQVSAGVYATVRFDQYDIHNLRTIEKTWYARHATLHNGKKISINNV
Cry51Aa1    LNSDNTVTYTGSVVSQVSAGVYATVRFDQYDIHNLRTIEKTWYARHATLHNGKKISINNV
            ************************************************************

TIC807      TEMAPTSPIKTN     (SEQ ID NO:5)
Cry51Aa1    TEMAPTSPIKTN     (SEQ ID NO:59)
            ************
```

HEMIPTERAN-AND COLEOPTERAN ACTIVE TOXIN PROTEINS FROM BACILLUS THURINGIENSIS

CROSS-REFERENCE TO RELATED APPLICATIONS

This application claims priority to U.S. Provisional Patent Application No. 60/914,364, filed Apr. 27, 2007.

STATEMENT REGARDING FEDERALLY SPONSORED RESEARCH OR DEVELOPMENT

Not Applicable.

APPENDIX

Not Applicable.

INCORPORATION OF SEQUENCE LISTING

A paper copy of the Sequence Listing and a computer readable form of the sequence listing provided herein, containing the file named "38-21(54839) SEQ LIST", which is 126976 bytes in size (measured in MS-DOS), and are herein incorporated by reference. This Sequence Listing consists of SEQ ID NOs:1-59.

BACKGROUND OF THE INVENTION

1. Field of the Invention

This invention relates generally to the field of insect inhibitory *Bacillus thuringiensis* proteins and, more particularly, to *B. thuringiensis* crystal proteins that inhibit hemipteran insects. Isolated polynucleotides and proteins, transgenic plants and related methods that provide for inhibition of hemipteran insects are described. Also described are methods for combining the *B. thuringiensis* crystal proteins that inhibit hemipteran insects with distinct insect control agents to obtain increased levels of hemipteran insect inhibition, hemipteran insect resistance management, or an expanded spectrum of insect pest control.

2. Related Art

*Bacillus thuringiensis* Crystal Proteins

The Gram-positive soil bacterium *Bacillus thuringiensis* is well known for its production of proteinaceous parasporal crystals, or δ-endotoxins, that are toxic to a variety of Lepidopteran, Coleopteran, and Dipteran larvae. *B. thuringiensis* produces crystal proteins during sporulation which are specifically toxic to certain species of insects. Many different strains of *B. thuringiensis* have been shown to produce insecticidal crystal proteins, and compositions comprising *B. thuringiensis* strains which produce proteins having insecticidal activity have been used commercially as environmentally-acceptable insecticides because of their toxicity to the specific target insect, and non-toxicity to plants and other non-targeted organisms.

Commercial formulations of naturally occurring *B. thuringiensis* isolates have long been used for the biological control of agricultural insect pests. In commercial production, the spores and crystals obtained from the fermentation process are concentrated and formulated for foliar application according to conventional agricultural practices.

Nomenclature of Crystal Proteins

A review by Hofte et al., (Hofte and Whiteley, Microbiol. Rev., 53:242-255, 1989) describes the general state of the art with respect to the majority of insecticidal *B. thuringiensis* strains that have been identified which are active against insects of the Order Lepidoptera, i.e., caterpillar insects. This treatise also describes *B. thuringiensis* strains having insecticidal activity against insects of the Orders Diptera (i.e., flies and mosquitoes) and Coleoptera (i.e., beetles). A number of genes encoding crystal proteins have been cloned from several strains of *B. thuringiensis*. Hofte et al. (1989) discusses the genes and proteins that were identified in *B. thuringiensis* prior to 1990, and sets forth the nomenclature and classification scheme which has traditionally been applied to *B. thuringiensis* genes and proteins. Cry1 genes encode Lepidopteran-toxic Cry1 proteins. Cry2 genes encode Cry2 proteins that are toxic to both Lepidopterans and Dipterans. Cry3 genes encode Coleopteran-toxic Cry3 proteins, while Cry4 genes encode Dipteran-toxic Cry4 proteins, etc.

Recently a new nomenclature has been proposed which systematically classifies the Cry proteins based upon amino acid sequence homology rather than upon insect target specificities. This classification scheme and a comprehensive list of insect inhibitory *B. thuringiensis* genes is summarized in the listing of Insecticidal Toxin Proteins as set forth in the Neil Crickmore website accessed through Cambridge University on the world wide web at lifesci.sussex.ac.uk/home/Neil_Crickmore/Bt/index.html.

Mode of Crystal Protein Toxicity

All δ-endotoxin crystals are toxic to insect larvae by ingestion. Solubilization of the crystal in the midgut of the insect releases the protoxin form of the δ.-endotoxin which, in most instances, is subsequently processed to an active toxin by midgut protease. The activated toxins recognize and bind to the brush-border of the insect midgut epithelium through receptor proteins. Several putative crystal protein receptors have been isolated from certain insect larvae (Jurat-Fuentes J L, Adang M J. Biochemistry. 45(32):9688, 2006; Griffitts J S et al., Science. 307(5711):922, 2005; Jurat-Fuentes J L, Adang M J. Eur J. Biochem.; 271(15):3127, 2004). The binding of active toxins is followed by intercalation and aggregation of toxin molecules to form pores within the midgut epithelium. This process leads to osmotic imbalance, swelling, lysis of the cells lining the midgut epithelium, and eventual larvae mortality. With the advent of molecular genetic techniques, various δ.-endotoxin genes have been isolated and their DNA sequences determined. These genes have been used to construct certain genetically engineered *B. thuringiensis* products that have been approved for commercial use. Recent developments have seen new δ.-endotoxin delivery systems developed, including plants that contain and express genetically engineered δ.-endotoxin genes. Control of Lepidopteran and Coleopteran pests in a variety of transgenic crop plants including corn, cotton, potato, tomato and rice that express δ.-endotoxin genes is well established. Advantages associated with expression of the δ.-endotoxin genes in crop plants include increased yields and decreased use of chemical insecticides. The advantages of transgenic crops that express insect inhibitory δ.-endotoxin genes has lead to widespread use in crops such as corn and cotton.

Unfortunately, the δ.-endotoxin genes that are currently available do not provide for control of all insect pests that plague crop production. In particular, Hemipteran insects still must be controlled by use of insecticides in crops where they cause damage. The Hemipteran or "piercing/sucking" insects are especially damaging to plants in that they are also known to transmit damaging plant viruses and cause plants to be more susceptible to bacterial and fungal infection. There is thus a need for additional materials and methods that would permit inhibition of Hemipteran insect pests in crops. There is also a need to obtain several different types of Hemipteran insect control agents with distinct modes of action for use in transgenic plants as Hemipteran insect resistance management tools.

Given the need for Hemipteran insect control agents, a variety of approaches have been disclosed. U.S. Pat. No. 5,723,440 describes a Cyt1Ba1 protein with purported activity against Hemipteran insects. However, Wellman-Desbiens and Cote (J. Econ. Entomol. 98(5):1469-1479., 2005) were unable to confirm this activity with the Hemipteran insect *Lygus hesperus*. U.S. Pat. No. 5,885,963 discloses the use of *B. thuringiensis israelensis* Cyt toxins that purportedly inhibit Hemipteran pests. More recently, US20060242732 discloses *B. thuringiensis* crystal proteins with activity against the Hemipteran insect *Lygus lineolaris*. These proteins are unrelated to the Cyt proteins described in U.S. Pat. Nos. 5,723,440 and 5,885,963.

SUMMARY OF THE INVENTION

It is in view of the above problems that the present invention was developed.

The invention first relates to an isolated polynucleotide which encodes a TIC807 insect inhibitory protein or an insect inhibitory protein fragment derived therefrom, wherein the insect inhibitory protein or protein fragment comprises a polypeptide sequence that has at least about 70% sequence identity to a corresponding polypeptide sequence contained within SEQ ID NO:5. The polynucleotide sequences of the invention can also encode polypeptide sequences with at least about 80%, 90%, 95%, or 100% sequence identity to the corresponding insect inhibitory polypeptide sequence contained within SEQ ID NO:5. In certain embodiments, the polynucleotide encodes the polypeptide sequence of SEQ ID NO:5.

Isolated polynucleotides of the invention can encode a TIC807 insect inhibitory protein or insect inhibitory protein fragment derived therefrom that inhibits a Hemipteran insect, a Heteropteran insect or a Homopteran insect. The Hemipteran insect can be a *Lygus* insect and the Homopteran insect can be an aphid, a hopper, or a whitefly. The encoded TIC807 insect inhibitory protein or insect inhibitory protein fragment derived therefrom inhibits *Lygus* at a *Lygus* diet concentration of at least about 5 ppm, 50 ppm, 250 ppm, or 500 ppm (parts per million) of the TIC807 protein or protein fragment in the *Lygus* diet. The TIC807 insect inhibitory protein fragment encoded by the polynucleotide comprises a peptide sequence of at least 250 amino acid residues. This isolated polynucleotide encoding the TIC807 protein can be modified for improved expression in plants compared to the native coding sequence. One embodiment of a TIC807 encoding polynucleotide that is designed for expression in plants is provided as SEQ ID NO:6. Other embodiments of TIC807 encoding polynucleotides for expression in plants are provided as SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53. In other embodiments, the polynucleotide designed for expression in plants encodes a TIC807 protein with an N-terminal chloroplast or plastid targeting peptide. One embodiment is provided in SEQ ID NO:7 and comprises a polynucleotide designed for expression of the TIC807 toxin in plants that is also linked in frame to a nucleotide sequence encoding a plastid targeting peptide. The plastid targeting peptide is operably linked to TIC807 upon expression and functions to direct the insertion of the TIC807 toxin into the plant plastid.

Other isolated polynucleotides of the invention include polynucleotides that hybridize under high stringency conditions with either the native *Bacillus thuringiensis* TIC807 gene (SEQ ID NO:4) or with the gene designed for improved plant expression of TIC807, which has an enriched G+C content (SEQ ID NO:6) compared to the native coding sequence set forth at SEQ ID NO:4. Polynucleotides that hybridize under stringent conditions can be selected from the group consisting of SEQ ID NO:4, SEQ ID NO:6 and SEQ ID NO:7.

The invention further provides for transgenic plants or plant parts derived therefrom comprising a TIC807 insect inhibitory protein or an insect inhibitory protein fragment derived therefrom, wherein the TIC807 insect inhibitory protein or protein fragment comprises a polypeptide sequence that has at least about 70% sequence identity to a corresponding polypeptide sequence contained within SEQ ID NO:5. The transgenic plant or plant part comprises the TIC807 protein or protein fragment at a concentration from at least about 5 µg to about 250 µg of the TIC807 protein or protein fragment per gram fresh weight plant tissue, or any amount in between. The TIC807 insect inhibitory protein fragment encoded by the polynucleotide comprises a peptide sequence of at least 250 amino acid residues. The transgenic plant part can be a cell, a leaf, a stem, a flower, a sepal, a fruit, a root, or a seed.

The invention also provides for transformed host cells comprising a polynucleotide which encodes a TIC807 insect inhibitory protein or an insect inhibitory protein fragment derived therefrom, wherein the insect inhibitory protein or protein fragment comprises a polypeptide sequence that has at least about 70% sequence identity to a corresponding polypeptide sequence contained within SEQ ID NO:5. The TIC807 insect inhibitory protein fragment encoded by the polynucleotide comprises a peptide sequence of at least 250 amino acid residues. The transformed host cell can be a bacterial cell or a plant cell. Transformed plant cells of the invention can be selected from the group consisting of barley, corn, oat, rice, rye, sorghum, turf grass, sugarcane, wheat, alfalfa, banana, broccoli, bean, cabbage, canola, carrot, cassava, cauliflower, celery, citrus, cotton, a cucurbit, eucalyptus, flax, garlic, grape, onion, lettuce, pea, peanut, pepper, potato, poplar, pine, sunflower, safflower, soybean, strawberry, sugar beet, sweet potato, tobacco, tomato, ornamental, shrub, nut, chickpea, pigeonpea, millets, hops, and pasture grass plant cells. In certain embodiments, the transformed plant cell is a cotton plant cell. Plants derived from the transformed plant host cells, seeds produced from the plants derived from the transformed host cell, and progeny plants from that seed are also contemplated by the invention. Transformed bacterial host cells of the invention can be selected from the group consisting of an *Agrobacterium*, a *Bacillus*, an *Escherichia*, a *Salmonella*, a *Pseudomonas*, and a *Rhizobium* bacterial cell. In certain embodiments, the transformed bacterial cell is a *Bacillus thuringiensis* cell. Another embodiment of the invention relates to a biologically-pure or isolated culture of an *Escherichia coli* strain SIC8088 harboring vector pIC17040, deposited on Mar. 16, 2007 with the Agricultural Research Culture Collection, Northern Regional Research Laboratory (NRRL), Peoria, Ill., USA and having Accession No. NRRLB-50030.

The invention further provides methods for controlling *Lygus* comprising the steps of: (a) providing a *Lygus* inhibitory amount of a TIC807 insect inhibitory protein or an insect inhibitory protein fragment derived therefrom, wherein the insect inhibitory protein or protein fragment comprises a polypeptide sequence that has at least about 70% sequence identity to a corresponding polypeptide sequence contained within SEQ ID NO:5; and (b) contacting the *Lygus* with the inhibitory amount of the polypeptide sequence, thereby controlling a *Lygus* insect. The polypeptide sequence used in this method can also have at least about 90% or 100% sequence identity to the corresponding a corresponding insect inhibitory polypeptide sequence contained within SEQ ID NO:5. The TIC807 insect inhibitory protein fragment encoded by the polynucleotide comprises a peptide sequence of at least 250 amino acid residues. In one embodiment of this method, the *Lygus* inhibitory amount of the polypeptide sequence can be provided in a *Lygus* diet in step (a) and the *Lygus* can be contacted in step (b) by permitting the *Lygus* to feed on the diet. In a more particular embodiment of the method, the *Lygus* diet is a transgenic plant. When the *Lygus* diet of this method is a transgenic plant, the *Lygus* inhibitory amount of the polypeptide sequence is from at least about 5 µg to about 250 µg per gram fresh weight tissue of the transgenic plant. In other embodiments of this method, the *Lygus* inhibitory amount of the polypeptide sequence is provided in step (a) by spraying a composition comprising the polypeptide on a plant. The composition used in this embodiment of the method comprises bacterial cells or bacterial spores that express the polypeptide. In particular embodiments of the method, the bacterial cells or bacterial spores are *Bacillus* cells or *Bacillus* spores. The composition used in this method can also comprise parasporal crystals containing the polypeptide. In any of these methods of controlling *Lygus*, the plant can be infested with *Lygus*.

The invention also provides for isolated oligonucleotides comprising at least 12 contiguous nucleotides of a sequence contained within the native *Bacillus thuringiensis* TIC807 protein encoded by SEQ ID NO:4 or contained within the complement of SEQ ID NO:4. Such isolated oligonucleotides are useful for detecting either SEQ ID NO:4 or related polynucleotides that encode insect inhibitory proteins related to TIC807. Isolated oligonucleotides comprising at least 12 contiguous nucleotides of a sequence contained within SEQ ID NO:6, SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53 or contained within the complement of SEQ ID NO:6, SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53 are also provided by the invention. These isolated oligonucleotides are useful for detecting either SEQ ID NO:6, a polynucleotide designed for use in plants encoding a TIC807 protein or related polynucleotides that encode TIC807 proteins. Kits for detection of a polynucleotide sequence in a sample that comprise an oligonucleotide that specifically hybridizes to a polynucleotide sequence of SEQ ID NO:6 or a complement thereof and a control polynucleotide that hybridizes to the oligonucleotide are also provided by this invention.

Other embodiments of the invention include compositions comprising at least two degenerate oligonucleotide primers of at least 12 nucleotides, wherein nucleotide sequences of the degenerate oligonucleotide primers are derived from the polypeptide sequence of SEQ ID NO:5. These oligonucleotide primer compositions are useful for detecting polynucleotide sequences in either plant or bacterial samples that encode TIC807 proteins.

The invention further provides methods for detecting or isolating a polynucleotide that encodes a TIC807 protein or a TIC807 related protein in a sample that comprise the steps of: (a) selecting a pair of degenerate oligonucleotide primers capable of producing an amplicon, wherein nucleotide sequences of the degenerate oligonucleotide primers are derived from a TIC807 polypeptide sequence of SEQ ID NO:5; (b) producing an amplicon from the polynucleotide sequence in the sample; and (c) detecting or isolating the amplicon, thereby detecting or isolating a polynucleotide that encodes a TIC807 protein or a TIC807 related protein in a sample. In this method the detected or isolated amplicon can encode a polypeptide that has at least 45%, 70%, or 90% sequence identity to TIC807 (SEQ ID NO:5). Other methods for detecting or isolating a polynucleotide that encodes a TIC807 protein in a sample provided herein comprise the steps of: (a) selecting a degenerate oligonucleotide or collection of degenerate oligonucleotides, wherein nucleotide sequences of the degenerate oligonucleotide primers are derived from a TIC807 polypeptide sequence of SEQ ID NO:5; (b) hybridizing the degenerate oligonucleotide or collection of degenerate oligonucleotides to the sample; (c) detecting hybridization in the sample to a polynucleotide, thereby detecting polynucleotide that encodes a TIC807 protein in a sample, and (d) isolating the polynucleotide detected by hybridization in step (c). In this method, the detected polynucleotide can encode a polypeptide that has at least 45%, 70%, or 90% sequence identity to TIC807 (SEQ ID NO:5).

The invention also provides methods for expressing a TIC807 protein in a plant that comprise the steps of: (a) inserting into a plant cell genome a nucleic acid sequence comprising in the 5' to 3' direction a recombinant, double-stranded DNA molecule, wherein the recombinant, double-stranded DNA molecule comprises: i. a promoter that functions in the plant cell; ii. a polynucleotide sequence encoding a polypeptide comprising a TIC807 insect inhibitory protein or an insect inhibitory protein fragment derived therefrom, wherein the insect inhibitory protein or protein fragment comprises a polypeptide sequence that has at least about 70% sequence identity to a corresponding polypeptide sequence contained within SEQ ID NO:5; and iii. a 3' non-translated nucleotide sequence that functions in the cells of the plant to cause polyadenylation, wherein said promoter, said polynucleotide sequence, and said 3' non-translated nucleotide sequence are operably linked (b) obtaining a transformed plant cell containing the nucleic acid sequence of step (a); and (c) regenerating from the transformed plant cell a transformed plant that expresses the TIC807 protein. In this method, the polynucleotide sequence of step (a) can encode either a TIC807 protein that has at least 90% sequence identity to SEQ ID NO:5 or can encode the TIC807 protein of SEQ ID NO:5. This polynucleotide sequence can be SEQ ID NO:6 or another sequence designed for expression in plants that encodes a TIC807 protein. Polynucleotide sequences designed for expression in plants include, but are not limited to, SEQ ID NO:6, SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53. The TIC807 insect inhibitory protein fragment encoded by the polynucleotide comprises a peptide sequence of at least 250 amino acid residues. In other embodiments of this method, the polynucleotide sequence of step (a) that encodes a TIC807 protein is operably linked to a polynucleotide sequence that encodes a plastid targeting polypeptide. The polypeptide of SEQ ID NO:8 comprises a TIC807 protein that is operably linked to the plastid targeting polypeptide that can be used in certain embodiments of this method.

The invention further provides recombinant DNA vectors comprising in the 5' to 3' direction: i. a promoter that functions in the plant cell; ii. a polynucleotide sequence encoding a polypeptide comprising a TIC807 insect inhibitory protein or an insect inhibitory protein fragment derived therefrom, wherein said insect inhibitory protein or protein fragment comprises a polypeptide sequence that has at least about 70% sequence identity to a corresponding polypeptide sequence contained within SEQ ID NO:5; and iii. a 3' non-translated nucleotide sequence that functions in the cells of the plant to cause polyadenylation, where the promoter, said polynucleotide sequence, and said 3' non-translated nucleotide sequence are operably linked. In these vectors, the polynucleotide sequence can also encode either a TIC807 protein that has at least 90% sequence identity to SEQ ID NO:5 or can encode the TIC807 protein of SEQ ID NO:5. The TIC807 insect inhibitory protein fragment encoded by the polynucleotide comprises a peptide sequence of at least 250 amino acid residues. The polynucleotide sequence encoding the TIC807 protein can be a sequence that is designed for expression in plants. Polynucleotide sequences designed for expression in plants include, but are not limited to, SEQ ID NO:6, SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53. In other embodiments, the polynucleotide sequence that encodes a TIC807 protein is operably linked to a polynucleotide sequence that encodes a plastid targeting polypeptide. A vector of the invention can comprise a polynucleotide sequence encodes the polypeptide of SEQ ID NO:8, such as the polynucleotide sequence is SEQ ID NO:7. Vectors of the invention can further comprise a polynucleotide that encodes a selectable marker gene. A selectable marker gene that confers resistance to AMPA, atrazine, bromoxynil, dalapon, dicamba, glyphosate, hygromycin, methotrexate, neomycin, phosphinotricin, a sulfonylurea or 2,4-D or combinations thereof can be used in the vectors of the invention.

Also provided by this invention are commodity products produced from a plant or seed wherein the commodity product contains a detectable amount of a TIC807 protein or a polynucleotide that encodes a TIC807 protein. This commodity product can be derived from a cotton plant or cotton plant seed, or similarly from corn, rice, wheat, soy, chickpea, pigeonpea, sugarcane, sugarbeet, and the like. For example, when the commodity product is derived from a cotton plant or cotton plant seed, the commodity product can be lint, oil, meal, or hulls.

The invention also provides a method for controlling at least one insect pest comprising the steps of: (a) providing at least two different insect pest inhibitory agents in a composition, the composition comprising (i) an insect inhibitory amount of a TIC807 protein and an insect inhibitory amount of (ii) at least one ribonucleotide sequence that functions upon ingestion by the insect pest to inhibit a biological function within the insect pest and/or (iii) an insect inhibitory amount of at least one insect inhibitory protein other than a TIC807 protein; and (b) contacting the insect pest or pests with an inhibitory amount of the composition. In this method, the insect pest controlled can be a hemipteran insect, a heteropteran insect or a homopteran insect. One hemipteran insect controlled by the method is a Lygus insect. A homopteran insect controlled by the method is an aphid, a hopper or a whitefly. In this method, a TIC807 insect inhibitory protein or protein fragment comprises a polypeptide sequence that has at least about 70% sequence identity to a corresponding polypeptide sequence contained within SEQ ID NO:5. A TIC807 protein used in the method can also comprise a TIC807 insect inhibitory protein fragment of at least 250 amino acid residues in length. When a biological function is inhibited by a ribonucleotide, the biological function within the insect pest in ii) can be an essential biological function. The essential biological function inhibited by the method can be provided by an essential protein or ribonucleic acid of the insect pest, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis. The essential biological function can be inhibited in Lygus by a ribonucleotide sequence that comprises from about 21 to about 5000 contiguous nucleotides exhibiting from about 80 to about 100% sequence identity to a nucleotide coding sequence selected from the group consisting of SEQ ID NO:24 through SEQ ID NO:39. In other embodiments of this method, the one insect inhibitory protein other than a TIC807 protein can be derived from Bacillus thuringiensis. This insect inhibitory protein other than a TIC 807 protein can be selected from the group consisting of AXMI-027, AXMI-036, AXMI-038, AXMI-018, AXMI-020, AXMI-021, AXMI-010, AXMI-003, AXMI-008, AXMI-006, AXMI-007, AXMI-009, AXMI-014, ET29, ET37, AXMI-004, AXMI-028, AXMI-029, AXMI-007, AXMI-008, AXMI-0080rf2, AXMI-009, AXMI-014, TIC809, TIC810, TIC812, TIC127 and TIC128. In other embodiments where two Lygus inhibitory proteins other than a TIC807 protein are expressed in the plant, the two Lygus inhibitory proteins can comprise TIC809 and TIC810. In other embodiments of the method, both a first and a second insect pest can be controlled by the composition. In these embodiments of the method, the second insect pest can be inhibited by either the ribonucleotide sequence of the composition or by the protein other than a TIC807 protein of the composition. This second insect pest can be a lepidopteran insect pest. The second insect pest can be inhibited by a protein selected from the group consisting of a Cry1A protein, a Cry1B protein, a Cry1C, a Cry1A/Cry1F chimeric protein, and a Cry2Ab protein. In certain embodiments of the method of controlling at least one insect pest, the composition provides for a synergistic insect inhibitory effect. In other embodiments of the method of controlling at least one insect pest, the composition provides for an additive insect inhibitory effect. In the methods of controlling at least one insect pest, the composition can be a transgenic plant.

The invention also provides a method for protecting a plant from Lygus infestation comprising expressing a Lygus inhibitory amount of at least two different Lygus inhibitory agents in the plant, where the Lygus inhibitory agents comprise (i) a Lygus inhibitory amount of a TIC807 protein; (ii) a Lygus inhibitory amount of at least one Lygus inhibitory protein other than a TIC807 protein and/or (iii) a Lygus inhibitory amount of at least one ribonucleotide sequence that functions upon ingestion by the Lygus to inhibit a biological function within the Lygus. This essential biological function in Lygus can be provided by an essential protein or ribonucleic acid of the Lygus, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis. This essential biological function in *Lygus* can be inhibited by a ribonucleotide sequence that comprises from about 21 to about 5000 contiguous nucleotides exhibiting from about 80 to about 100% sequence identity to a nucleotide coding sequence selected from the group consisting SEQ ID NO:24 through SEQ ID NO:39. In certain embodiments of this method, the *Lygus* inhibitory protein other than a TIC807 protein is derived from *Bacillus thuringiensis*. The *Lygus* inhibitory protein other than TIC807 can be selected from the group consisting of AXMI-027, AXMI-036, AXMI-038, AXMI-018, AXMI-020, AXMI-021, AXMI-010, AXMI-003, AXMI-008, AXMI-006, AXMI-007, AXMI-009, AXMI-014, ET29, ET37, AXMI-004, AXMI-028, AXMI-029, AXMI-007, AXMI-008, AXMI-0080rf2, AXMI-009, AXMI-014, TIC809, TIC810, TIC812, TIC127 and TIC128. In other embodiments where two *Lygus* inhibitory proteins other than a TIC807 protein are expressed in the plant, the two *Lygus* inhibitory proteins can comprise TIC809 and TIC810. In this method, a TIC807 insect inhibitory protein or protein fragment comprises a polypeptide sequence that has at least about 70% sequence identity to a corresponding polypeptide sequence contained within SEQ ID NO:5. A TIC807 protein used in the method can also comprise a TIC807 insect inhibitory protein fragment of at least 250 amino acid residues in length. In certain embodiments of this method, expression of the *Lygus* inhibitory agents provides for a synergistic *Lygus* inhibitory effect. In other embodiments of this method, expression of the *Lygus* inhibitory agents provides for an additive *Lygus* inhibitory effect. By using this method, the plant can be protected from *Lygus hesperus* or *Lygus lineolaris*.

The invention further provides for isolated proteins, wherein the isolated protein comprises a polypeptide sequence of at least 9 amino acids in length that is contained within SEQ ID NO:5. The isolated protein can have a polypeptide sequence at least 12, 16, 32 or 250 amino acids in length. The isolated protein of at least 32 amino acids in length can have a polypeptide sequence at least about 80%, 90%, or 95% sequence identity to a corresponding polypeptide sequence contained within SEQ ID NO:5. The isolated protein of the invention can be an insect inhibitory protein when it is at least 250 amino acids in length. The isolated insect inhibitory protein of at least 250 amino acids can inhibit *Lygus*. In certain embodiments, the isolated insect inhibitory protein of at least 250 amino acids inhibits *Lygus* at a *Lygus* diet concentration of the protein of at least about 5 ppm, 50 ppm, 250 ppm, or 500 ppm. The isolated protein can also be the protein of SEQ ID NO:5. The isolated protein can further comprise a carrier protein. This carrier protein can be an albumin or a KLH protein. Isolated proteins of the invention can also further comprise a covalent modification selected from the group consisting of an indicator reagent, an amino acid spacer, an amino acid linker, a signal sequence, a chloroplast transit peptide sequence, a vacuolar targeting sequence, a stop transfer sequence, a transmembrane domain, a protein purification ligand, or a combination thereof.

The invention also provides for antibodies that specifically bind to a TIC807 protein or peptide epitope derived therefrom, where the TIC807 protein or epitope comprising at least 9 contiguous amino acids of SEQ ID NO:5.

The invention further provides kits for detection of a TIC807 protein in a sample that comprises: a) an antibody that specifically binds to a TIC807 protein or peptide epitope derived therefrom, the protein or epitope comprising at least 9 contiguous amino acids of SEQ ID NO:5; and b) a control TIC807 protein or peptide epitope derived therefrom that comprises at least 9 contiguous amino acids of SEQ ID NO:5.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings:

FIG. 1 illustrates a Needleman-Wunsch global alignment between TIC807 (SEQ ID NO:5) and Cry15Aa (SEQ ID NO:41).

FIG. 6 illustrates the ClustalW comparison of TIC807 (SEQ ID NO:5) and Cry51Aa1 (SEQ ID NO:59).

DETAILED DESCRIPTION OF THE PREFERRED EMBODIMENTS

I. Definitions

Figure 2:
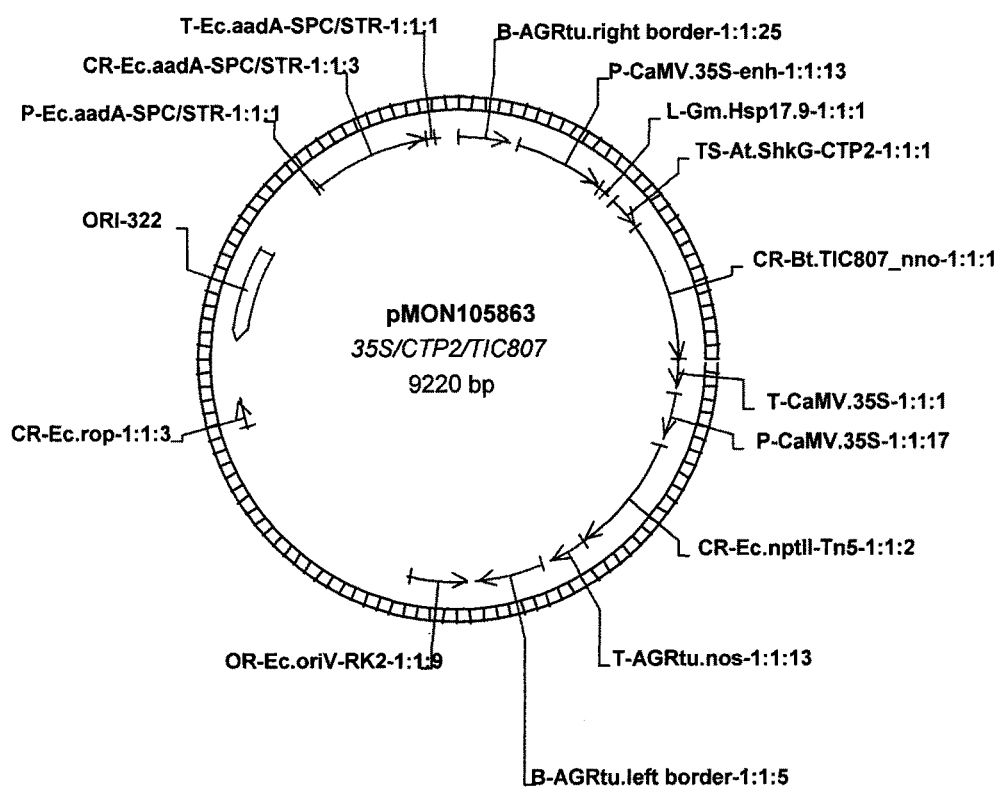
FIG. 2 illustrates the *Agrobacterium*-mediated plant transformation vector pMON105863 that contains both a plastid targeted TIC807 plant expression cassette and a neomycin selection cassette within the *Agrobacterium* border sequences.
Figure 3:
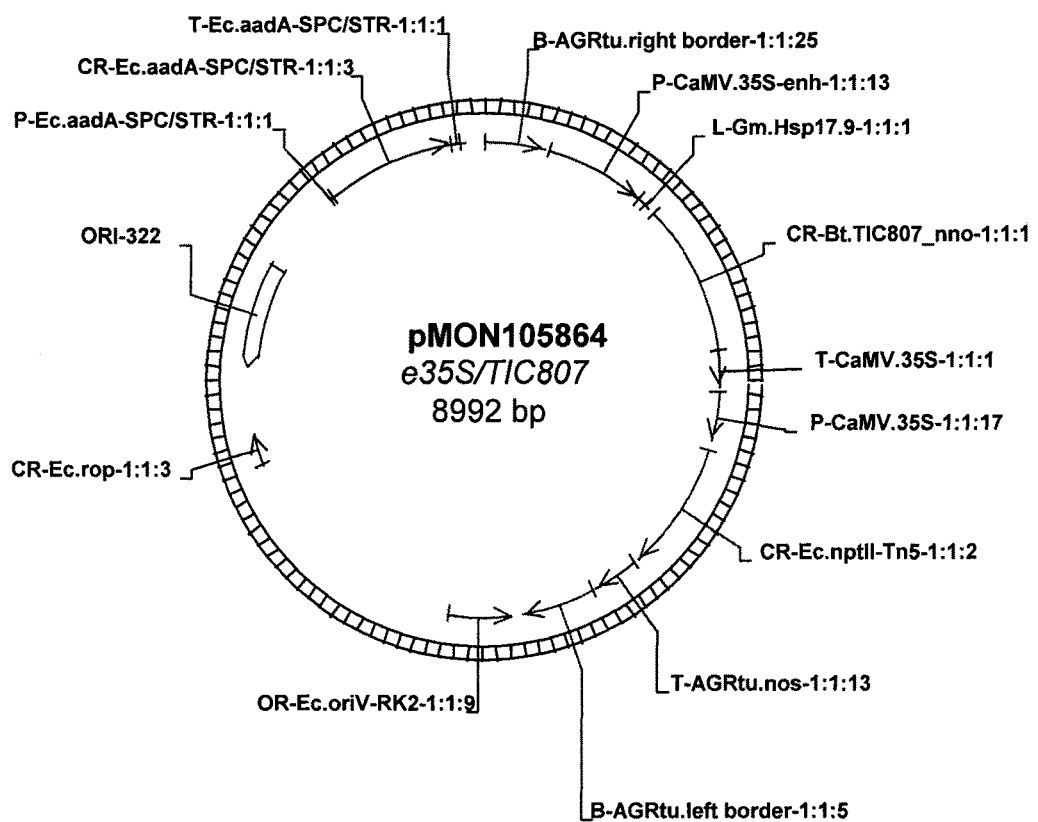
FIG. 3 illustrates the *Agrobacterium*-mediated plant transformation vector pMON105864 that contains both a TIC807 plant expression cassette and a neomycin selection cassette within the *Agrobacterium* border sequences.
Figure 4:
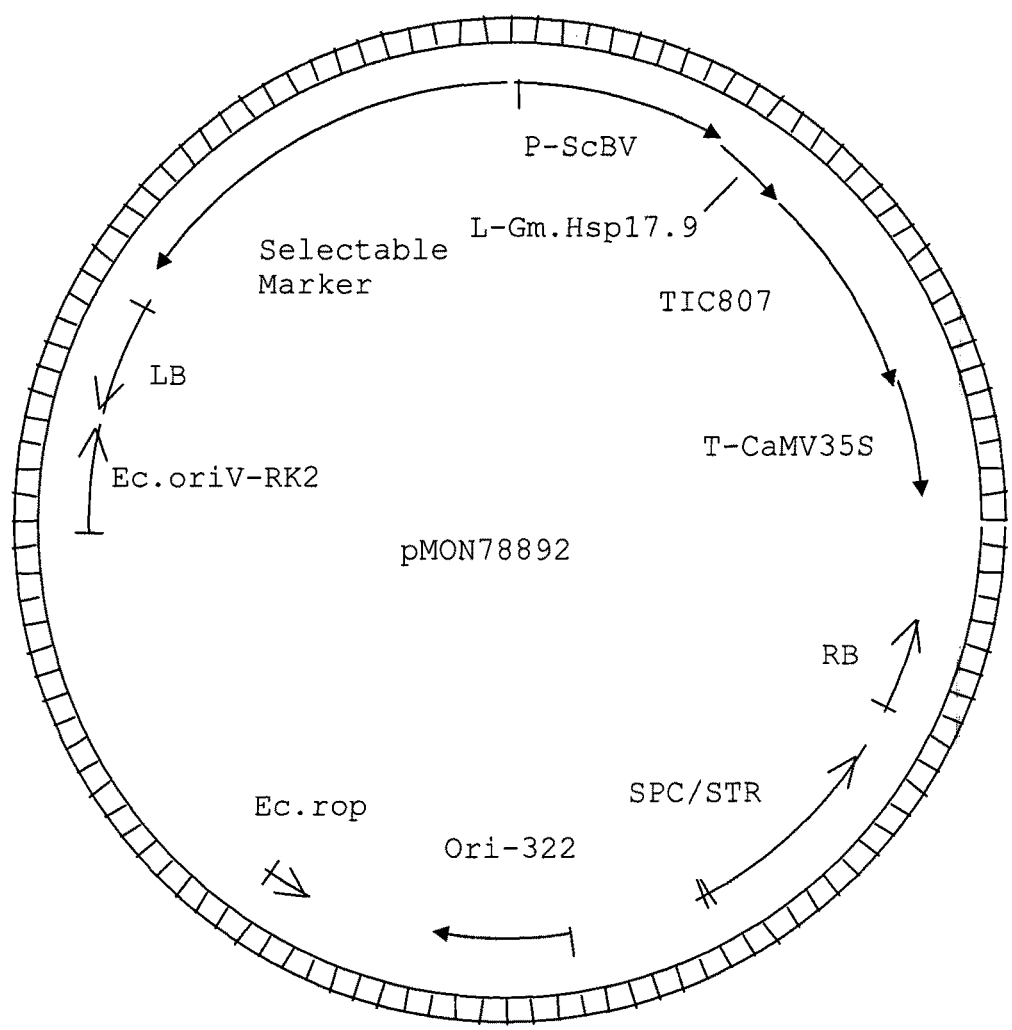
FIG. 4 illustrates the Agrobacterium-mediated plant transformation vector pMON78892 that contains both a plastid targeted TIC807 plant expression cassette and a neomycin selection cassette within the *Agrobacterium* border sequences.

As used herein, the phrase "additive effect", in reference to insect inhibition, refers to an inhibitory effect obtained by combining at least two distinct insect inhibitory agents that is either: a) quantitatively equivalent to the predicted additive effect of the combination of the two agents and/or is b) qualitatively equivalent to the combination of effects obtained from each agent administered on its own. Examples of quantitative effects include, but are not limited to, changes in $LC_{50}$, $EC_{50}$, $IC_{50}$, percent mortality, or percent stunting values indicative of increased insect inhibitory activity against a known insect target of both insect inhibitory agents. Examples of additive qualitative effects include, but are not limited, to an expanded spectrum of insect inhibition (i.e., hemipteran and lepidopteran insects) that reflects the simple combination of the spectrum exhibited by each insect inhibitory agent (i.e., the combination of hemipteran insect inhibition provided by one agent and lepidopteran insect inhibition provided by another agent).

The phrase "Consensus sequence" as used herein refers to an amino acid, DNA or RNA sequence created by aligning two or more homologous sequences and deriving a new sequence that represents the common amino acid, DNA or RNA sequence.

The term "Construct" as used herein refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e., operably linked.

The phrase "biological functional equivalents" as used herein refers to peptides, polypeptides and proteins that contain a sequence or structural feature similar to a TIC807 protein of the present invention, and which exhibit the same or similar insect inhibitory activity of a TIC807 protein of the present invention. Biological functional equivalents also include peptides, polypeptides and proteins that react with (i.e., specifically bind) to monoclonal and/or polyclonal antibodies raised against a TIC807 protein and that exhibit the same or similar insect inhibitory activity as a TIC807 protein.

The phrase "DNA construct" as used herein refers to any DNA molecule in which two or more ordinarily distinct DNA sequences have been covalently linked. Examples of DNA constructs include but are not limited to plasmids, cosmids, viruses, BACs (bacterial artificial chromosome), YACs (yeast artificial chromosome), plant minichromosomes, autonomously replicating sequences, phage, or linear or circular single-stranded or double-stranded DNA sequences, derived from any source, that are capable of genomic integration or autonomous replication. DNA constructs can be assembled by a variety of methods including, but not limited to, recombinant DNA techniques, DNA synthesis techniques, PCR (Polymerase Chain Reaction) techniques, or any combination of techniques.

The phrase "a heterologous promoter", as used herein in the context of a DNA construct, refers to either: i) a promoter that is derived from a source distinct from the operably linked structural gene or ii) a promoter derived from the same source as the operably linked structural gene, where the promoter's sequence is modified from its original form. The phrase "high stringency hybridization conditions" refers to nucleic acid hybridization conditions comprising a salt concentration of about 1×SSC, a detergent concentration of about 0.1% SDS, and a temperature of about 50° C., or equivalents thereof. The term "homolog" as used herein refers to a gene related to a second gene by identity of either the DNA sequences or the encoded protein sequences. Genes that are homologs can be genes separated by the event of speciation (see "ortholog"). Genes that are homologs may also be genes separated by the event of genetic duplication (see "paralog"). Homologs can be from the same or a different organism and may perform the same biological function in either the same or a different organism.

The term "insect" as used herein refers to any embryonic, larval, nymph or adult form of an Arachnid, Coleopteran, Ctenophalides, Dipteran, Hemipteran, Homopteran, Heteropteran, Hymenopteran or Lepidopteran insect.

The phrase "an insect inhibitory amount", refers to an amount of a TIC807 polypeptide, a ribonucleotide, or a protein other than a TIC807 protein that results in any measurable inhibition of insect growth, insect development, insect reproduction, insect feeding behavior, insect mating behavior and/or any measurable decrease in the adverse effects caused by insect feeding on a plant. Similarly, a "*Lygus* inhibitory amount" refers to an amount of a TIC807 polypeptide, a ribonucleotide, or a protein other than a TIC807 protein that results in any measurable inhibition of *Lygus* growth, *Lygus* development, *Lygus* reproduction, *Lygus* feeding behavior, *Lygus* mating behavior and/or any measurable decrease in the adverse effects caused by *Lygus* feeding on a plant.

As used herein when referring to an "isolated DNA molecule", it is intended that the DNA molecule be one that is present, alone or in combination with other compositions, but not within its natural environment. For example, a coding sequence, intron sequence, untranslated leader sequence, promoter sequence, transcriptional termination sequence, and the like, that are naturally found within the DNA of a plant genome are not considered to be isolated from the plant genome so long as they are within the plant genome from which it was first observed. However, each of these components, and subparts of these components, would be "isolated" within the scope of this disclosure so long as the structures and components are not within the plant genome. Similarly, a nucleotide sequence encoding a *Bacillus thuringiensis* insecticidal protein or any insecticidal variant of that protein would be an isolated nucleotide sequence so long as the nucleotide sequence was not within the DNA of the *Bacillus thuringiensis* bacterium from which the structure was first observed. An artificial nucleotide sequence encoding the same amino acid sequence or a substantially identical amino acid sequence that the native *B. thuringiensis* nucleotide sequence encodes would be considered to be isolated for the purposes of this disclosure. For the purposes of this disclosure, any transgenic nucleotide sequence, i.e., the nucleotide sequence of the DNA inserted into the genome of the cells of a plant would be considered to be an isolated nucleotide sequence whether it is present within the plasmid used to transform plant cells from which transgenic event arose, within the genome of the transgenic event, present in detectable amounts in tissues, progeny, biological samples or commodity products derived from the transgenic event. The nucleotide sequence or any fragment derived therefrom would therefore be considered to be isolated or isolatable if the DNA molecule can be extracted from cells, or tissues, or homogenate from a plant or seed or plant organ; or can be produced as an amplicon from extracted DNA or RNA from cells, or tissues, or homogenate from a plant or seed or plant organ, any of which is derived from such materials derived from the transgenic event.

The phrase "ribonucleotide sequence that functions upon ingestion by the insect pest to inhibit a biological function" refers to RNA sequence that comprises a sequence that is substantially homologous to an RNA molecule encoded by a nucleotide sequence within the genome of the insect, that provides for inhibition of the insect.

As used herein, the term "substantially homologous" or "substantial homology", with reference to a nucleic acid or polypeptide sequence, refers to a nucleotide or polypeptide sequence that has about 65% to about 70% sequence identity, or more preferably from about 80% to about 85% sequence identity, or most preferable from about 90% to about 95% sequence identity, to about 99% or 100% sequence identity, with another nucleotide or polypeptide sequence.

As used herein, the phrase "synergistic effect", in reference to insect inhibition, refers to an inhibitory effect obtained by combining at least two distinct insect inhibitory agents that is either: a) quantitatively greater than the predicted additive effect of the combination of the two agents and/or is b) qualitatively distinct from any effects obtained from either agent administered on its own. Examples of quantitative effects include, but are not limited to, changes in $LC_{50}$, $EC_{50}$, $IC_{50}$, percent mortality, or percent stunting values indicative of increased insect inhibitory activity against a known insect target of both insect inhibitory agents. Examples of synergistic qualitative effects include, but are not limited to, an expanded spectrum of insect inhibition (i.e., hemipteran, homopteran, and lepidopteran insects inhibition) that does not reflect the simple combination of the spectrum exhibited by each insect inhibitory agent alone (i.e., the combination of hemipteran insect inhibition provided by one agent and lepidopteran insect inhibition provided by another agent).

The phrase "TIC807 protein" as used herein refers to an insect inhibitory protein of at least 250 amino acids that display at least 70% sequence identity to a corresponding polypeptide sequence contained within SEQ ID NO:5.

The phrase "TIC807 related protein" as used herein refers to an insect inhibitory protein of at least 250 amino acids that display at least 45% sequence identity to a corresponding polypeptide sequence contained within SEQ ID NO:5.

The phrase "operably linked" as used herein refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter and is linked such that the resulting translation product is in frame with the translational open reading frame that encodes the protein desired. Nucleic acid sequences that can be operably linked include, but are not limited to, sequences that provide gene expression functions (i.e., gene expression elements such as promoters, 5' untranslated regions, introns, protein coding regions, 3' untranslated regions, polyadenylation sites, and/or transcriptional terminators), sequences that provide DNA transfer and/or integration functions (i.e., T-DNA border sequences, site specific recombinase recognition sites, integrase recognition sites), sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, site specific recombination sequences) and sequences that provide replication functions (i.e., bacterial origins of replication, autonomous replication sequences, centromeric sequences).

As used herein, the phrases or terms "sequence identity", "sequence similarity" or "homology" is used to describe sequence relationships between two or more nucleotide sequences. The percentage of "sequence identity" between two sequences is determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. A first nucleotide sequence when observed in the 5' to 3' direction is said to be a "complement" of, or complementary to, a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence.

As used herein, the phrase "corresponding polypeptide sequence contained within SEQ ID NO:5" refers to polypeptide sequence within SEQ ID NO:5 that will yield the highest percent identity when aligned with the other polypeptide sequence.

As used herein, a "comparison window" refers to a conceptual segment of at least 6 contiguous positions, usually about 50 to about 100, more usually about 100 to about 150, in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Those skilled in the art should refer to the detailed methods used for sequence alignment in the Wisconsin Genetics Software Package Release 7.0, Genetics Computer Group, 575 Science Drive Madison, Wis., USA) or refer to Ausubel et al. (1998) for a detailed discussion of sequence analysis.

The term "regeneration" as used herein refers to any method of obtaining a whole plant from any one of a seed, a plant cell, a group of plant cells, plant callus tissue, or an excised piece of a plant.

The term "transformation" as used herein refers to a process of introducing an exogenous DNA sequence (e.g., a vector, a recombinant DNA molecule) into a cell or protoplast in which that exogenous DNA is incorporated into a chromosome or is capable of autonomous replication.

The phrase "transgenic plant" refers to a plant or progeny thereof derived from a transformed plant cell or protoplast, wherein the plant DNA contains an introduced exogenous DNA molecule not originally present in a native, non-transgenic plant of the same species.

The phrases "stabilized RNA", "stabilized dsRNA", and "stabilized siRNA" refer to combinations of sense-oriented and anti-sense-oriented, transcribed RNA separated by short sequences that permit formation of a hairpin or stem loop structure in the RNA molecule. The phrase "vascular tissue" as used herein refers to any tissues or cells contained within the vascular bundle of a plant, including, but not limited to, phloem, protophloem, metaphloem, xylem, protoxylem, or metaxylem cells or tissues.

The term "vector" as used herein refers to any recombinant polynucleotide construct that may be used for the purpose of transformation, i.e., the introduction of heterologous DNA into a host cell.

II. Polynucleotides of the Invention

A variety of polynucleotides that encode TIC807 insect inhibitory proteins are contemplated by this invention. Such polynucleotides are useful for production of TIC807 insect inhibitory proteins in host cells when operably linked to suitable promoter, transcription termination and/or polyadenylation sequences. Such polynucleotides are also useful as probes for isolating homologous or substantially homologous polynucleotides that encode TIC807 proteins.

One source of polynucleotides that encode TIC807 is the *Bacillus thuringiensis* strain which contains the TIC807 polynucleotide of SEQ ID NO:4 that encodes the TIC807 polypeptide of SEQ ID NO:5. This polynucleotide sequence was originally isolated from a *Bacillus thuringiensis* host and is thus suitable for expression of the encoded TIC807 polypeptide in other bacterial hosts. For example, SEQ ID NO:4 can be used to express TIC807 protein in bacterial hosts that include but are not limited to *Agrobacterium*, a *Bacillus*, an *Escherichia*, a *Salmonella*, a *Pseudomonas*, and a *Rhizobium* bacterial host cells. The SEQ ID NO:4 probes are also useful as probes for isolating homologous or substantially homologous polynucleotides that encode TIC807 proteins. Such probes can be used to identify homologous or substantially homologous polynucleotides derived from *Bacillus* strains.

Polynucleotides that encode TIC807 proteins can also be synthesized de novo from a TIC807 polypeptide sequence. The sequence of the polynucleotide gene can be deduced from a TIC807 polypeptide sequence through use of the genetic code. Computer programs such as "BackTranslate" (GCG™ Package, Acclerys, Inc. San Diego, Calif.) can be used to convert a peptide sequence to the corresponding nucleotide sequence that encodes the peptide. Examples of a TIC807 polypeptide sequences that can be used to obtain corresponding nucleotide encoding sequences include, but are not limited to, the TIC807 polypeptide sequence of SEQ ID NO:5. Furthermore, synthetic TIC807 polynucleotide sequences of the invention can be designed so that they will be expressed in plants. U.S. Pat. No. 5,500,365 describes a method for synthesizing plant genes to improve the expression level of the protein encoded by the synthesized gene. This method relates to the modification of the structural gene sequences of the exogenous transgene, to cause them to be more efficiently transcribed, processed, translated and expressed by the plant. Features of genes that are expressed well in plants include elimination of sequences that can cause undesired intron splicing or polyadenylation in the coding region of a gene transcript while retaining substantially the amino acid sequence of the toxic portion of the insecticidal protein. A similar method for obtaining enhanced expression of transgenes in monocotyledonous plants is disclosed in U.S. Pat. No. 5,689,052. Exemplary polynucleotide sequences designed for expression of a TIC807 protein in plants include, but are not limited to, SEQ ID NO:6, SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53.

III. Isolated Oligonucleotides, Kits and Methods for Isolation and/or Detection of Polynucleotides that Encode TIC807 Proteins Isolated oligonucleotides for identifying, detecting, or isolating polynucleotides that encode TIC807 proteins are also provided by the present invention.

In one embodiment, the isolated oligonucleotides comprise at least 12 contiguous nucleotides of a sequence contained within the *Bacillus thuringiensis* TIC807 encoding gene of SEQ ID NO:4 or contained within the complement of SEQ ID NO:4. Such oligonucleotides can be used in hybridization or PCR based methods for identifying or isolating polynucleotides that encode TIC807 proteins from strains of *Bacillus thuringiensis*. Such oligonucleotides can also be used to confirm the presence or absence of a TIC807-encoding polynucleotide in a host cell. It is further recognized that the oligonucleotides can be used to mutagenize SEQ ID NO:4 when they comprise additional sequences that comprise mismatches to SEQ ID NO:4. Such "mutagenesis" oligos are useful for identification of TIC807 variants with enhanced insect inhibitory activity.

In another embodiment, the isolated oligonucleotides comprise at least 12 contiguous nucleotides of a sequence contained within the polynucleotide of SEQ ID NO:6 or contained within the complement of SEQ ID NO:6. The polynucleotide of SEQ ID NO:6 is specifically designed for expression in transgenic plants and encodes the TIC807 protein of SEQ ID NO:5. In still other embodiments, the isolated oligonucleotides comprise at least 12 contiguous nucleotides of a sequence contained within the polynucleotide of SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53 or contained within the complement of SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53. Such oligonucleotides can be used in hybridization or PCR based methods for detecting SEQ ID NO:6, SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53 polynucleotides in samples derived from transgenic plants. When the sample is a ribonucleic acid sample, the oligonucleotides can be used in hybridization or PCR based methods to quantitate levels of TIC807 transgene expression. When the sample is a deoxyribonucleic acid sample, the oligonucleotides can be used in hybridization or PCR based methods to determine the presence or absence of the TIC807 transgene in the sample. It is also anticipated that the SEQ ID NO:6 derived oligonucleotides can be used to determine the presence or absence of a TIC807 transgene in a deoxyribonucleic acid sample derived from a commodity product. Given the exquisite sensitivity of certain nucleic acid detection methods that employ oligonucleotides, it is anticipated that the SEQ ID NO:6 derived oligonucleotides can also be used to detect a TIC807 transgene in commodity products derived from pooled sources where only a fraction of the commodity product is derived from a transgenic plant containing SEQ ID NO:6. It is further recognized that the oligonucleotides can be used to mutagenize SEQ ID NO:6 when they comprise additional sequences that comprise mismatches to SEQ ID NO:6. Such "mutagenesis" oligonucleotides are useful for identification of TIC807 variants with enhanced insect inhibitory activity and/or enhanced expression in transgenic plant host cells.

It is of course understood that the oligonucleotides of the invention can further comprise additional sequences that are not identical or complementary to the polynucleotide sequences that encode TIC807 proteins. Additional sequences may include but are not limited to sequences used as adapters that facilitate cloning, mutagenesis, or detection. The oligonucleotides of the invention can further comprise additional covalent modifications. Covalent modifications would include, but are not limited to, detectable labels such as isotopes, fluorophores, and haptens. Biotin is one particularly useful hapten.

Kits for detection of a TIC807 polynucleotide sequence in a sample that comprise at least one oligonucleotide that specifically hybridizes to the polynucleotide sequence of SEQ ID NO:6, SEQ ID NO: 45, SEQ ID NO:46, SEQ ID NO:47, SEQ ID NO:48, SEQ ID NO:49, SEQ ID NO:50, SEQ ID NO:51, SEQ ID NO:52, SEQ ID NO:53 or a complement thereof are further contemplated by this invention. In the context of the kits of this invention, the term "specifically hybridize" means that the oligonucleotides will hybridize and detect SEQ ID NO:6, SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53 in a sample from a transgenic plant transformed with one or more copies of SEQ ID NO:6, SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53 but will not specifically hybridize and detect any sequences in a control non-transgenic plant that does not contain SEQ ID NO:6, SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53. These kits can also comprise a control polynucleotide that hybridizes to said oligonucleotide, instructions for use, and/or reagents for hybridizing or detecting hybridization of the oligonucleotides to SEQ ID NO:6, SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53. In certain applications, including but not limited to those application that use a Polymerase Chain Reaction, the kits will naturally comprise more than one oligonucleotide that specifically hybridizes to the polynucleotide sequence of SEQ ID NO:6, SEQ ID NO: 45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53.

IV. Degenerate Oligonucleotides, Degenerate Oligonucleotide Compositions and Methods of Use Degenerate oligonucleotides, compositions comprising degenerate oligonucleotides, and methods of using such oligonucleotides to identify, detect or isolate TIC807 protein encoding polynucleotides are also contemplated by this invention. Although such degenerate oligonucleotides are derived from SEQ ID NO:5, those skilled in the art appreciate that such oligonucleotides can be used to identify a variety of TIC807 proteins and TIC807-related proteins. Such TIC807 proteins are anticipated to have at least 70%, 80%, 90%, 95%, 98% or 100% amino acid identity to SEQ ID NO:5 and to have insect inhibitory activity. The TIC807 related proteins have at least 45% sequence identity to SEQ ID NO:5 and have insect inhibitory activity.

The design of degenerate oligonucleotides sequences from peptide sequences is accomplished through use of the genetic code, whereby codons corresponding to each of the encoded amino acids are synthesized. Degenerate oligonucleotides can comprise either pool of oligonucleotides comprising all of the potential sequences that encode a given peptide sequence. Alternatively, the degenerate oligonucleotides can also comprise a sequence that contains a neutral base (i.e., a base that can base pair adequately with all nucleotides at a given position). Neutral bases include, but are not limited to, inosine. Considerations involved in the design and use of degenerate oligonucleotide primers or probes are well known to those skilled in the art (see Molecular Cloning: A Laboratory Manual (Third Edition), Sambrook and Russell, Cold Spring Harbor Press, 2001).

This invention discloses and claims compositions comprising at least two degenerate oligonucleotide primers of at least 12 nucleotides from the polypeptide sequence of SEQ ID NO:5. Such compositions can be used in either hybridization or polymerase chain reaction based methods for isolation or detection of polynucleotides that encode TIC807 proteins or TIC807 related proteins. The degenerate oligonucleotides of this composition can further comprise additional sequences that are not identical or complementary to the polynucleotide sequences that encode TIC807 proteins. Additional sequences may include but are not limited to sequences used as adapters that facilitate cloning, mutagenesis, or detection. The degenerate oligonucleotides of the invention can further comprise additional covalent modifications. Covalent modifications would include, but are not limited to, detectable labels such as an isotopes, fluorophores, and haptens. Biotin is one particularly useful hapten.

Use of the degenerate oligonucleotide primers in PCR based methods of isolating or detecting polynucleotides that encode a TIC807 protein or a TIC807 related protein in a sample is specifically contemplated. In brief, a pair of degenerate oligonucleotide primers capable of producing an amplicon is selected and used in a polymerase chain reaction with a sample that contains a polynucleotide that encodes a TIC807 protein or a TIC807 related protein. A suitable source of samples for this method include, but are not limited to, various *Bacillus thuringiensis* strains. The degenerate oligonucleotides are capable of producing an amplicon when the oligonucleotides correspond to predicted sense and antisense strand sequences and are in a 5' to 3' orientation that will prime DNA polymerase-mediated synthesis of a DNA strand that is complementary to the other opposing oligonucleotide. The degenerate oligonucleotide primers are derived from a TIC807 polypeptide sequence of SEQ ID NO:5. This amplicon can be detected by use of an intercalating dye to produce an amplicon. The amplicon can also be isolated by cloning the isolated amplicon fragment into a plasmid, cosmid, bacteriophage, or other cloning vector. Once cloned, this amplicon can be further characterized by sequencing to determine the percent identity of the amplicon-encoded protein to TIC807 (SEQ ID NO:5). It is anticipated that polynucleotides encoding TIC807 proteins of at least 70% or at least 90% identity to SEQ ID NO:5 and TIC807-related proteins of at least 45% identity to SEQ ID NO:5 can be detected or isolated by these methods. Such TIC807 proteins or a TIC807 related proteins can subsequently be screened for insect inhibitory activity.

The degenerate TIC807 oligonucleotides can also be used as probes in hybridization based methods of detecting or isolating polynucleotides that encode TIC807 proteins or a TIC807 related proteins. Methods for detecting a polynucleotide that encodes a TIC807 protein in a sample first comprise selecting a degenerate oligonucleotide or collection of degenerate oligonucleotide derived from a TIC807 polypeptide sequence of SEQ ID NO:5. These degenerate oligonucleotides may further comprise detectable labels such as isotopes, fluorophores, and haptens. Biotin is one particularly useful hapten. The samples include, but are not limited to, samples derived from various *Bacillus thuringiensis* strains. The sample can be a library of plasmid, cosmid or bacteriophage clones derived from one or more *Bacillus thuringiensis* strains. The degenerate oligonucleotide or collection of degenerate oligonucleotides are hybridized to the sample under suitable hybridization stringency conditions. These conditions are related to the length of the degenerate oligonucleotide(s), the degree of degeneracy, their G+C content, the desired or projected percent sequence identity of target sequences in the sample and other factors. Hybridization to a polynucleotide is detected by methods including, but not limited to, radiometric, fluorometric, luminometric, and/or ELISA-based methods. Following detection, the polynucleotide can be isolated by serial dilution and re-hybridization. All of the above listed steps of degenerate oligonucleotide design, oligonucleotide labeling, library preparation, hybridization, detection and isolation are well know to those skilled in the art (see Molecular Cloning: A Laboratory Manual (Third Edition), Sambrook and Russell, Cold Spring Harbor Press, 2001). It is anticipated that polynucleotides encoding TIC807 proteins of at least 70% or at least 90% identity to SEQ ID NO:5 and TIC807-related proteins of at least 45% identity to SEQ ID NO:5 can be detected or isolated by these methods. Such TIC807 proteins or a TIC807 related proteins can subsequently be screened for insect inhibitory activity following expression in an acrystallifeorus *Bacillus thuringiensis* strain. The TIC807 or TIC807 related proteins can inhibit a hemipteran pest such as *Lygus*. Alternatively, the TIC807 or TIC807 related proteins can inhibit other insect pests including Arachnid, Coleopteran, Ctenophalides, Dipteran, Hymenopteran or Lepidopteran pests, or can inhibit both hemipteran pests and other families of insect pests.

V. DNA Constructs Comprising TIC807 Bacterial Expression Cassettes

To express TIC807 proteins in bacterial hosts, polynucleotides that encode TIC807 are operably linked to suitable promoters and transcriptional termination sequences that function in bacterial hosts to yield bacterial expression cassettes. Promoters and termination signals that function in bacterial cells can be derived from bacterial genes, bacteriophage genes or synthetic methods. These expression cassettes can then be transferred to suitable bacterial vectors that comprise replication origins and selectable markers via standard recombinant DNA techniques.

In the practice of this invention, bacterial promoters, termination signals and vectors that function in *Bacillus* hosts are particularly useful for expression of TIC807 polypeptides. In many instances, the TIC807 gene comprising its endogenous promoter and termination sequences can be used for expression of TIC807 proteins in *Bacillus* host cells that include but are not limited to *Bacillus thuringiensis* hosts. For such experiments, use of a shuttle vector that functions in both *E. coli* and *Bacillus* hosts is particularly useful. Examples of such shuttle vectors include, but are not limited to, vectors such as pEG854 described in U.S. Pat. No. 5,650,308. These shuttle vectors include antibiotic resistance marker genes permitting transformation of *Bacillus* hosts. Preferred *Bacillus thuringiensis* hosts include, but are not limited to, acrystalliferous (Cry protein deficient) *B. thuringiensis* host strains such as EG10368 and EG10650 (described in U.S. Pat. No. 5,759,538). When the TIC807 protein is expressed in a acrystalliferous (Cry protein deficient) *B. thuringiensis* host strains, the TIC807 protein is easily isolated as a parasporal crystal following induction of sporulation in the host cells. This facile *Bacillus thuringiensis* expression system can thus be used to test large numbers of TIC807 protein variants for insect inhibitory activity.

VI. DNA Constructs Comprising TIC807 Plant Expression Cassettes

The construction of expression cassettes for use in monocotyledonous plants or dicotyledonous plants is well established. Expression cassettes are DNA constructs where various promoter, coding, and polyadenylation sequences are operably linked. In general, expression cassettes typically comprise a promoter that is operably linked to a sequence of interest which is operably linked to a polyadenylation or terminator region. In certain instances including, but not limited to, the expression of transgenes in monocot plants, it may also be useful to include an intron sequence. When an intron sequence is included, it is typically placed in the 5' untranslated leader region of the transgene. In certain instances, it may also be useful to incorporate specific 5' untranslated sequences in a transgene to enhance transcript stability or to promote efficient translation of the transcript.

A variety of promoters can be used in the practice of this invention. One broad class of useful promoters is referred to as "constitutive" promoters in that they are active in most plant organs throughout plant development. For example, the promoter can be a viral promoter such as a CaMV35S or FMV35S promoter. The CaMV35S and FMV35S promoters are active in a variety of transformed plant tissues and most plant organs (e.g., callus, leaf, seed and root). Enhanced or duplicate versions of the CaMV35S and FMV35S promoters are particularly useful in the practice of this invention (U.S. Pat. No. 5,378,619). Other useful nopaline synthase (NOS) and octopine synthase (OCS) promoters (which are carried on tumor-inducing plasmids of *A. tumefaciens*), the cauliflower mosaic virus (CaMV) 19S promoters, a maize ubiquitin promoter, the rice Act1 promoter and the Figwort Mosaic Virus (FMV) 35S promoter (see e.g., U.S. Pat. No. 5,463,175). It is understood that this group of exemplary promoters is non-limiting and that one skilled in the art could employ other promoters that are not explicitly cited here in the practice of this invention.

Promoters that are active in certain plant tissues (i.e., tissue specific promoters) can also be used to drive expression of TIC807 proteins or other insect inhibitory agents. Since certain hemipteran insect pests are "piercing/sucking" insect that typically feed by inserting their proboscis into the vascular tissue of host plants, promoters that direct expression of insect inhibitory agents in the vascular tissue of the transgenic plants are particularly useful in the practice of this invention. Various Caulimovirus promoters, including but not limited to the CaMV35S, CaMV19S, FMV35S promoters and enhanced or duplicated versions thereof, typically deliver high levels of expression in vascular tissues and are thus useful for expression of TIC807 proteins or other insect inhibitory agents. Phloem-limited viruses such as the rice tungro virus (Bhattacharyya-Pakrasi et al., Plant J. 4[1] 71-79, 1993) and the commelina yellow mottle virus (Medberry et al., Plant Cell 4:185-192, 1992) also contain useful promoters that are active in vascular tissues. For control of hemipteran insects that feed on phloem, phloem cell-specific or phloem-preferred promoters can be used to express TIC807 proteins or other insect inhibitory agents in phloem of transgenic plants. Examples of useful phloem specific promoters include, but are not limited to, PP2-type gene promoters (U.S. Pat. No. 5,495,007), sucrose synthase promoters (Yang and Russell, Proc. Natl. Acad. Sci. USA 87:4144-4148, 1990), glutamine synthetase promoters (Edwards et al., Proc. Natl. Acad. Sci. USA 87:3459-3463, 1990), and phloem-specific plasma membrane H+-ATPase promoters (DeWitt et al., Plant J. 1[1]: 121-128, 1991), prunasin hydrolase promoters (U.S. Pat. No. 6,797,859), and a rice sucrose transporter (U.S. Pat. No. 7,186,821). For control of hemipteran pests that feed on xylem tissue, a variety of promoters that are active in xylem tissue including, but not limited to, protoxylem or metaxylem can be used. Promoters active in xylem tissue include, but are not limited to, promoters associated with phenylpropanoid biosynthetic pathways, such as the phenylalanine ammonia-lyase (PAL) promoters, cinnamate 4-hydroxylase (C4H) promoters, coumarate 3-hydroxylase promoters, O-methyl transferase (OMT) promoters, 4-coumarate:CoA ligase (4CL) promoters (U.S. Pat. No. 6,831,208), cinnamoyl-CoA reductase (CCR) promoters and cinnamyl alcohol dehydrogenase (CAD) promoters.

Transcriptional enhancer elements can also be used in conjunction with any promoter that is active in a plant cell or with any basal promoter element that requires an enhancer for activity in a plant cell. Transcriptional enhancer elements can activate transcription in various plant cells and are usually 100-200 base pairs long. The enhancer elements can be obtained by chemical synthesis or by isolation from regulatory elements that include such elements, and can comprise additional flanking nucleotides that contain useful restriction enzyme sites to facilitate subsequence manipulation. Enhancer elements can be typically placed within the region 5' to the mRNA cap site associated with a promoter, but can also be located in regions that are 3' to the cap site (i.e., within a 5' untranslated region, an intron, or 3' to a polyadenylation site) to provide for increased levels of expression of operably linked genes. Enhancer elements can also be multimerized (provided in any finite number of linked copies) to provide for increased expression of operably linked genes. Multimerized enhancers include, but are not limited to, duplicate, triplicate, or quadruplicate copies of enhancers in any orientation or combination of orientations. Enhancers are often derived from plant viral promoters, particularly those of the of the double-stranded DNA Culimoviridae group comprising the cauliviruses and the badnaviruses. The plant viral promoters or derived plant viral enhancers can provide strong constitutive expression of operably linked genes in transgenic plants. Enhancers derived from fragments of these promoters have been demonstrated to effectively enhance the performance of promoters driving the expression of transgenes in plants. Examples of plant viruses useful for isolating enhancers include, but are not limited to, the cauliflower mosaic virus (CaMV) (see, e.g., Odel et al., Nature 313:810, 1985), the figwort mosaic virus (U.S. Pat. No. 5,378,619), the carnation etched ring virus (CERV) (Hull et al., (1986) EMBO Journal 5:3083-3090), the cassaya vein mosaic virus (CsVMV) (Calvert et al. (1995) J. Gen. Virol. 76: 1271-1278 and U.S. Pat. No. 6,963,021), the mirabilis mosaic virus (MMV) (Dey et al. (1999) Plant Mol Biol. 40:771-82), the Cestrum yellow leaf curling virus (CmYLCV) (Stavolone et al. (2003) Plant Mol Biol. 53:663-73), the cotton leaf curl Multan virus (CLCuMV) (Xie et al. (2003) Plant Mol Biol. 53:1-14), the commelina yellow mottle virus (COYMV) (U.S. Pat. No. 6,963,021) and the peanut chlorotic streak caulimovirus (PCLSV) (U.S. Pat. No. 5,850,019). Duplications of enhancers are used in enhanced versions of the CaMV 35S and FMV 35S promoters Various 5' untranslated leader sequences can also be operably linked to a coding sequence of interest in a plant expression cassette. Thus the plant expression cassette can contain one or more 5' non-translated leader sequences which serve to increase expression of operably linked nucleic acid coding sequences encoding either TIC807 or other proteins of interest. Without seeking to be limited by theory, such 5' untranslated leader sequences can increase the translational efficiency of the resultant mRNA and/or increase the stability of the resultant mRNA to provide increased levels of the operably linked and encoded protein of interest in the transgenic plant. Examples of other useful 5' leader sequences include, but are not limited to, the dSSU 5', PetHSP70 5', and GmHSP17.9 5' untranslated leader sequences. A translational enhancer sequence derived from the untranslated leader sequence from the mRNA of the coat protein gene of alfalfa mosaic virus coat protein gene can be placed between the promoter and the gene of interest to increase translational efficiency of the operably linked gene of interest (U.S. Pat. No. 6,037,527).

An intron may also be included in the DNA expression construct, especially in instances when the sequence of interest is to be expressed in monocot plants. For monocot plant use, introns such as the maize hsp70 intron (U.S. Pat. No. 5,424,412), the maize ubiquitin intron, the Adh intron 1 (Callis et al., 1987), the sucrose synthase intron (Vasil et al., 1989) or the rice Act1 intron (McElroy et al., 1990) can be used. Dicot plant introns that are useful include introns such as the CAT-1 intron (Cazzonnelli and Velten, 2003), the pKANNI-BAL intron (Wesley et al., 2001; Collier et al., 2005), the PIV2 intron (Mankin et al., 1997) and the "Super Ubiquitin" intron (U.S. Pat. No. 6,596,925; Collier et al., 2005) that have been operably integrated into transgenes. It is understood that this group of exemplary introns is non-limiting and that one skilled in the art could employ other introns that are not explicitly cited here in the practice of this invention.

In other embodiments of the invention, sequences encoding peptides that provide for the localization of a TIC807 protein in subcellular organelles can be operably linked to the sequences that encode the TIC807 polypeptide. TIC807 polypeptides that are operably linked to a signal peptide are expected to enter the secretion pathway and can be retained by organelles such as the endoplasmic reticulum (ER) or targeted to the vacuole by operably linking the appropriate retention or targeting peptides to the C-terminus of the TIC807 polypeptide. Examples of vacuolar targeting peptides include, but are not limited to, a CTPP vacuolar targeting signal from the barley lectin gene. Examples of ER targeting peptides include, but are not limited to, a peptide comprising a KDEL amino acid sequence. Without seeking to be limited by theory, localization of TIC807 polypeptides in either the endoplasmic reticulum or the vacuole can provide for desirable properties such as increased expression in transgenic plants and/or increased efficacy in inhibiting insects in transgenic plants.

Localization of TIC807 proteins to plant plastids including, but not limited to, chloroplasts is specifically contemplated herein. Plastid localization is typically accomplished by the operable linkage of a chloroplast transit peptide sequence to the N-terminus of the TIC807 protein. Chloroplast transit peptides (or CTPs) that can be used to localize TIC807 proteins in transgenic plants can be derived from nuclear encoded plant proteins that are targeted to plastids. Nuclear encoded plant proteins that are targeted to plastids include, but are not limited to, proteins involved in lipid, starch, or amino acid biosynthesis, as well as proteins involved in photosynthesis. Specific chloroplast transit peptides that can be used include, but are not limited to, CTPs from nuclear encoded Granule Bound Starch Synthase genes, plastidial Fatty Acid Desaturase genes, EPSPS genes, and RUBISCO small subunit genes. An exemplary CTP is the *Arabidopsis* EPSPS CTP. An exemplary nucleic acid (SEQ ID NO:7) encoding an *Arabidopsis* EPSPS CTP that is operably linked to a TIC807 protein is provided herein. Without seeking to be limited by theory, localization of TIC807 polypeptides in plastids can provide for desirable properties such as increased expression in transgenic plants and/or increased efficacy in inhibiting insects in transgenic plants. Increased expression of other *Bacillus thuringiensis* proteins through use of chloroplast targeting peptides such as Cry1Bb (U.S. patent application Ser. No. 10/525,318), Cry2Ab (U.S. Pat. No. 6,489,542), and Cry3Bb (U.S. Pat. No. 6,501,009) has been documented. Without being limited by theory, increased expression of TIC807 protein in a transgenic plant can provide for increased levels of insect inhibition, an expanded spectrum of insect pest inhibition, and/or an increased degree of insect pest resistance management.

As noted above, the sequence of interest can also be operably linked to a 3' non-translated region containing a polyadenylation signal. This polyadenylation signal provides for the addition of a polyadenylate sequence to the 3' end of the RNA. The *Agrobacterium* tumor-inducing (Ti) plasmid nopaline synthase (NOS) gene 3' and the pea ssRUBISCO E9 gene 3' un-translated regions contain polyadenylate signals and represent non-limiting examples of such 3' untranslated regions that can be used in the practice of this invention. It is understood that this group of exemplary polyadenylation regions is non-limiting and that one skilled in the art could employ other polyadenylation regions that are not explicitly cited here in the practice of this invention.

The DNA constructs that comprise the plant expression cassettes described above are typically maintained in various vectors. Vectors contain sequences that provide for the replication of the vector and covalently linked sequences in a host cell. For example, bacterial vectors will contain origins of replication that permit replication of the vector in one or more bacterial hosts. *Agrobacterium*-mediated plant transformation vectors typically comprise sequences that permit replication in both *E. coli* and *Agrobacterium* as well as one or more "border" sequences positioned so as to permit integration of the expression cassette into the plant chromosome. Such *Agrobacterium* vectors can be adapted for use in either *Agrobacterium tumefaciens* or *Agrobacterium rhizogenes*. Selectable markers encoding genes that confer resistance to antibiotics are also typically included in the vectors to provide for their maintenance in bacterial hosts.

VII. Insect Inhibitory Transgenic Plants and Methods for Obtaining Insect Inhibitory Transgenic Plants Methods of obtaining a transgenic plant capable of inhibiting insects are also provided by this invention. First, expression vectors suitable for expression of the TIC807 protein in various dicot and monocot plants are introduced into a plant, a plant cell or a plant tissue using transformation techniques as described herein. Next a transgenic plant containing or comprising the TIC807 expression vector is obtained by regenerating that transgenic plant from the plant, plant cell or plant tissue that received the expression vector. The final step is to obtain a transgenic plant that expresses an insect inhibitory amount of the TIC807 polypeptide. Transgenic plants expressing insect inhibitory amounts of TIC807 proteins contemplated herein include, but not limited to, barley, corn, oat, rice, rye, sorghum, turf grass, sugarcane, wheat, alfalfa, banana, broccoli, bean, cabbage, canola, carrot, cassaya, cauliflower, celery, citrus, cotton, a cucurbit, eucalyptus, flax, garlic, grape, onion, lettuce, pea, peanut, pepper, potato, poplar, pine, sunflower, safflower, soybean, strawberry, sugar beet, sweet potato, tobacco, tomato, ornamental, shrub, nut, chickpea, pigeonpea, millets, hops, and pasture grass plants.

TIC807 expression vectors can be introduced into the chromosomes of a host plant via methods such as *Agrobacterium*-mediated transformation, *Rhizobium*-mediated transformation, *Sinorhizobium*-mediated transformation, particle-mediated transformation, DNA transfection, DNA electroporation, or "whiskers"-mediated transformation. Suitable methods for transformation of plants include any method by which DNA can be introduced into a cell, such as by electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6,384,301; and protoplast transformation as illustrated in U.S. Pat. No. 5,508,184, etc. Aforementioned methods of introducing transgenes are well known to those skilled in the art and are described in U.S. Patent Application No. 20050289673 (*Agrobacterium*-mediated transformation of corn), U.S. Pat. No. 7,002,058 (*Agrobacterium*-mediated transformation of soybean), U.S. Pat. No. 6,365,807 (particle mediated transformation of rice), and U.S. Pat. No. 5,004,863 (*Agrobacterium*-mediated transformation of cotton). Through the application of techniques such as these, the cells of virtually any plant species may be stably transformed, and these cells developed into transgenic plants. Other techniques that may be particularly useful in the context of cotton transformation are disclosed in U.S. Pat. Nos. 5,846,797, 5,159,135, and 6,624,344; and techniques for transforming *Brassica* plants in particular are disclosed, for example, in U.S. Pat. No. 5,750,871; and techniques for transforming soybean are disclosed in for example in Zhang et al., 1999, and U.S. Pat. No. 6,384,301; and techniques for transforming corn are disclosed in WO9506722. Methods of using bacteria such as *Rhizobium* or *Sinorhizobium* to transform plants are described in Broothaerts, et al., Nature. 2005, 10; 433:629-33. It is further understood that the TIC807 expression vector can comprise cis-acting site-specific recombination sites recognized by site-specific recombinases, including Cre, Flp, Gin, Pin, Sre, pinD, Int-B13, and R. Methods of integrating DNA molecules at specific locations in the genomes of transgenic plants through use of site-specific recombinases can then be used (U.S. Pat. No. 7,102,055). Those skilled in the art will further appreciate that any of these gene transfer techniques can be used to introduce the expression vector into the chromosome of a plant cell, a plant tissue or a plant.

The use of plant transformation vectors comprising two separate T-DNA molecules, one T-DNA containing the gene or genes of interest (i.e., one or more insect inhibitory genes of interest) and another T-DNA containing a selectable and/or scoreable marker gene are also contemplated. In these two T-DNA vectors, the plant expression cassette or cassettes comprising the gene or genes of interest are contained within one set of T-DNA border sequences and the plant expression cassette or cassettes comprising the selectable and/or scoreable marker genes are contained within another set of T-DNA border sequences. In preferred embodiments, the T-DNA border sequences flanking the plant expression cassettes comprise both a left and a right T-DNA border sequence that are operably oriented to provide for transfer and integration of the plant expression cassettes into the plant genome. When used with a suitable *Agrobacterium* host in *Agrobacterium*-mediated plant transformation, the two T-DNA vector provides for integration of one T-DNA molecule containing the gene or genes of interest at one chromosomal location and integration of the other T-DNA containing the selectable and/or scoreable marker into another chromosomal location. Transgenic plants containing both the gene(s) of interest and the selectable and/or scoreable marker genes are first obtained by selection and/or scoring for the marker gene(s) and screened for expression of the genes of interest. Distinct lines of transgenic plants containing both the marker gene(s) and gene(s) of interest are subsequently outcrossed to obtain a population of progeny transgenic plants segregating for both the marker gene(s) and gene(s) of interest. Progeny plants containing only the gene(s) of interest can be identified by any combination of DNA, RNA or protein analysis techniques. Methods for using two T-DNA vectors have been described in U.S. Pat. Nos. 6,265,638, 5,731,179, U.S. Patent Application Publication No. 2003110532A1, and U.S. Patent Application Publication No. 20050183170A1.

Methods of introducing plant minichromosomes comprising plant centromeres that provide for the maintenance of the recombinant minichromosome in a transgenic plant can also be used in practicing this invention (U.S. Pat. No. 6,972,197). In these embodiments of the invention, the transgenic plants harbor the minichromosomes as extrachromosomal elements that are not integrated into the chromosomes of the host plant.

Transgenic plants are typically obtained by linking the gene of interest (i.e., in this case a TIC807 expression cassette) to a selectable marker gene, introducing the linked transgenes into a plant cell, a plant tissue or a plant by any one of the methods described above, and regenerating or otherwise recovering the transgenic plant under conditions requiring expression of said selectable marker gene for plant growth. The selectable marker gene can be a gene encoding a neomycin phosphotransferase protein, a phosphinothricin acetyltransferase protein, a glyphosate resistant 5-enol-pyruvylshikimate-3-phosphate synthase (EPSPS) protein, a hygromycin phosphotransferase protein, a dihydropteroate synthase protein, a sulfonylurea insensitive acetolactate synthase protein, an atrazine insensitive Q protein, a nitrilase protein capable of degrading bromoxynil, a dehalogenase protein capable of degrading dalapon, a 2,4-dichlorophenoxyacetate monooxygenase protein, a methotrexate insensitive dihydrofolate reductase protein, and an aminoethylcysteine insensitive octopine synthase protein. The corresponding selective agents used in conjunction with each gene can be: neomycin (for neomycin phosphotransferase protein selection), phosphinotricin (for phosphinothricin acetyltransferase protein selection), glyphosate (for glyphosate resistant 5-enol-pyruvylshikimate-3-phosphate synthase (EPSPS) protein selection), hygromycin (for hygromycin phosphotransferase protein selection), sulfadiazine (for a dihydropteroate synthase protein selection), chlorsulfuron (for a sulfonylurea insensitive acetolactate synthase protein selection), atrazine (for an atrazine insensitive Q protein selection), bromoxynil (for a nitrilase protein selection), dalapon (for a dehalogenase protein selection), 2,4-dichlorophenoxyacetic acid (for a 2,4-dichlorophenoxyacetate monooxygenase protein selection), methotrexate (for a methotrexate insensitive dihydrofolate reductase protein selection), or aminoethylcysteine (for an aminoethylcysteine insensitive octopine synthase protein selection).

Transgenic plants can also be obtained by linking a gene of interest (i.e., in this case an TIC807 expression cassette) to a scoreable marker gene, introducing the linked transgenes into a plant cell by any one of the methods described above, and regenerating the transgenic plants from transformed plant cells that test positive for expression of the scoreable marker gene. The scoreable marker gene can be a gene encoding a beta-glucuronidase protein, a green fluorescent protein, a yellow fluorescent protein, a red fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein or a chloramphenicol acetyl transferase protein.

When the expression vector is introduced into a plant cell or plant tissue, the transformed cells or tissues are typically regenerated into whole plants by culturing these cells or tissues under conditions that promote the formation of a whole plant (i.e., the process of regenerating leaves, stems, roots, and, in certain plants, reproductive tissues). The development or regeneration of transgenic plants from either single plant protoplasts or various explants is well known in the art (Horsch, R. B. et al. 1985). This regeneration and growth process typically includes the steps of selection of transformed cells and culturing selected cells under conditions that will yield rooted plantlets. The resulting transgenic rooted shoots are thereafter planted in an appropriate plant growth medium such as soil. Alternatively, transgenes can also be introduced into isolated plant shoot meristems and plants regenerated without going through callus stage tissue culture (U.S. Pat. No. 7,002,058). When the transgene is introduced directly into a plant, or more specifically into the meristematic tissue of a plant, seed can be harvested from the plant and selected or scored for presence of the transgene. In the case of transgenic plant species that reproduce sexually, seeds can be collected from plants that have been "selfed" (self-pollinated) or out-crossed (i.e., used as a pollen donor or recipient) to establish and maintain the transgenic plant line. Transgenic plants that do not sexually reproduce can be vegetatively propagated to establish and maintain the transgenic plant line. As used here, transgenic plant line refers to transgenic plants derived from a transformation event where the transgene has inserted into one or more locations in the plant genome. In a related aspect, the present invention also encompasses a seed produced by the transformed plant, a progeny from such seed, and a seed produced by the progeny of the original transgenic plant, produced in accordance with the above process. Such progeny and seeds will have an TIC807 protein-encoding transgene stably incorporated into their genome, and such progeny plants will inherit the traits afforded by the introduction of a stable transgene in Mendelian fashion. All such transgenic plants having incorporated into their genome transgenic DNA segments encoding one or more TIC807 proteins or polypeptides are aspects of this invention. It is further recognized that transgenic plants containing the DNA constructs described herein, and materials derived therefrom, may be identified through use of PCR or other methods that can specifically detect the sequences in the DNA constructs.

Once a transgenic plant is regenerated or recovered, a variety of methods can be used to identify or obtain a transgenic plant that expresses a insect inhibitory amount of TIC807. One general set of methods is to perform assays that measure the amount of TIC807 that is produced. For example, various antibody-based detection methods employing antibodies that recognize TIC807 can be used to quantitate the amount of TIC807 produced. Examples of such antibody based assays include, but are not limited to, ELISAs, RIAs, or other methods wherein an TIC807-recognizing antibody is detectably labelled with an enzyme, an isotope, a fluorophore, a lanthanide, and the like. By using purified or isolated TIC807 protein as a reference standard in such assays (i.e., providing known amounts of TIC807), the amount of TIC807 present in the plant tissue in a mole per gram of plant material or mass per gram of plant material can be determined. The TIC807 protein will typically be expressed in the transgenic plant at the level of "parts per million" or "ppm" where microgram levels of TIC807 protein are present in gram amounts of fresh weight plant tissue. In this case, 1 microgram of TIC807 protein per 1 gram of fresh weight plant tissue would represent a TIC807 concentration of 1 ppm. An insect inhibitory amount of TIC807 protein is at least 5 ppm (i.e., 5 μg TIC807 protein per gram fresh weight plant tissue). In preferred embodiments, a insect inhibitory amount of TIC807 protein is at least 50 ppm (i.e., 50 μg TIC807 protein per gram fresh weight plant tissue). In more preferred embodiments, the amount of TIC807 is at least 250 ppm (i.e. 50 μg TIC807 protein per gram fresh weight plant tissue).

Alternatively, the amount of TIC807 mRNA produced by the transgenic plant can be determined to identify plants that express insect inhibitory amounts of TIC807 protein. Techniques for relating the amount of protein produced to the amount of RNA produced are well known to those skilled in the art and include methods such as constructing a standard curve that relates specific RNA levels (i.e., TIC807 mRNA) to levels of the TIC807 protein (determined by immunologic or other methods). Methods of quantitating TIC807 mRNA typically involve specific hybridization of a polynucleotide to either the TIC807 mRNA or to a cDNA (complementary DNA) or PCR product derived from the TIC807 RNA. Such polynucleotide probes can be derived from either the sense and/or antisense strand nucleotide sequences of the TIC807 protein-encoding transgene. Hybridization of a polynucleotide probe to the TIC807 mRNA or cDNA can be detected by methods including, but not limited to, use of probes labelled with an isotope, a fluorophore, a lanthanide, or a hapten such as biotin or digoxigenin. Hybridization of the labelled probe may be detected when the TIC807 RNA is in solution or immobilized on a solid support such as a membrane. When quantitating TIC807 RNA by use of a quantitative reverse-transcriptase Polymerase Chain Reaction (qRT-PCR), the TIC807-derived PCR product can be detected by use of any of the aforementioned labelled polynucleotide probes, by use of an intercalating dye such as ethidium bromide or SYBR green, or use of a hybridization probe containing a fluorophore and a quencher such that emission from the fluorophore is only detected when the fluorophore is released by the 5' nuclease activity of the polymerase used in the PCR reaction (i.e., a TaqMan™ reaction; Applied Biosystems, Foster City, Calif.) or when the fluorophore and quencher are displaced by polymerase mediated synthesis of the complementary strand (i.e., Scorpion™ or Molecular Beacon℧ probes). Various methods for conducting qRT-PCR analysis to quantitate mRNA levels are well characterized (Bustin, S. A.; Journal of Molecular Endocrinology 29, 23, 2002). Fluorescent probes that are activated by the action of enzymes that recognize mismatched nucleic acid complexes (i.e., Invader™, Third Wave, Technologies, Madison, Wis.) can also be used to quantitate RNA. Those skilled in the art will also understand that RNA quantitation techniques such as Quantitative Nucleic Acid Sequence Based Amplification (Q-NASBA™) can be used to quantitate TIC807 protein-encoding mRNA and identify expressing plants.

Transgenic plants that express insect inhibitory amounts of TIC807 can also be identified by directly assaying such plants for insect inhibition. Since *Lygus* is a phytophagous, piercing-sucking insect, in planta expression and testing of toxin proteins must be presented in a manner that will permit feeding by the insect from the plant and its associated tissues. Several factors are critical in selecting a plant species for transformation that will allow for testing of the toxin proteins. The plant must be easily transformable and the tissue derived from the plant must be of the type that is preferred by the insect pest. For this purpose, it is preferable to use a plant that has leaves or other organs that have a large enough surface area to attach a barrier that inhibits the mobility of the insect pest and forces the organism to feed from the plant organ. In addition, the vascular tissue of the plant organ must be close enough to the surface of the organ to allow for the insect pest to probe, penetrate and subsequently feed. It is also preferable that the plant used in transformation be of the type that can easily be induced to develop from undifferentiated callus.

Insect pests such as *Lygus*, when feeding on a cotton plant, typically feed primarily at the flower buds or bolls. Cotton transformation is well known in the art; however the time it takes to go from transformation of plant cells to a fully developed cotton plant is too long to be practical for screening purposes. Therefore, undifferentiated cotton callus tissue would be the preferred initial transgenic plant testing material when studying *Lygus* feeding on cotton cells transformed with TIC807 proteins. Cotton cells are transformed with constructs containing the TIC807 protein encoding gene. Callus tissue is allowed to develop in tissue culture after transformation in a Petri dish. The *Lygus* nymphs are then placed into the Petri dish containing the callus. The secured lid of the Petri dish prevents the escape of the *Lygus* nymphs. Any material that will prevent *Lygus* escape but allow gas exchange in the Petri dish, for example, Parafilm® can be used to secure the Petri dish lid. A percentage of *Lygus* nymphs will find the callus tissue and feed. Scores for mortality and stunting are then calculated taking into account the background death that will occur from those insects which fail to feed on the callus tissue. *Lygus* nymphs would also be presented with control callus tissue that is not transformed with a TIC807 encoding gene as a control for normal nymph growth on callus tissue.

An alternate tissue for TIC807 protein mediated inhibition is leaf tissue. Any plant that possesses leaf tissue with a surface area sufficient to place a barrier preventing *Lygus* escape could be used. For example, alfalfa, corn, soybean or lettuce cells can be transformed with constructs containing the toxin protein encoding gene or genes of interest that have been optimized for monocot or dicot expression. The transformed cells are allowed to develop into callus tissue and then subsequently regenerated into plants. Insect pests such as *Lygus* nymphs are then allowed to feed when the plant has reached a sufficient level of maturity, such as when the leaves have grown to a size permitting the use of a physical barrier to prevent *Lygus* escape. The barrier to prevent escape of the *Lygus* nymphs can be any commercially available or home made device that permits contact of the *Lygus* nymphs with the leaf tissue and allows the insect to probe and feed from the vascular tissue of the leaf. Clip cages similar to those described by Mowry (1993) (J. Agric. Entomol. 10:181-184) would be sufficient to contain the *Lygus* nymphs for feeding. Mortality and stunting scores are then determined with respect to the background death that will occur from those insects which fail to feed on the leaf tissue. *Lygus* nymphs would also be presented with control leaf that is not transformed with a TIC807 encoding gene as a control for normal nymph growth on callus tissue.

The in planta insect inhibition assays can be used to identify transgenic plants that inhibit any of the large variety of insect pests that pierce and/or suck the fluids from the cells and tissues of plants that must be restricted to the assay tissue. In particular, such insect inhibition assays can be used to test plants expressing TIC807 and/or other insect inhibitory agents. Other insect inhibitory agents include, but are not limited to, i) ribonucleotide sequences that functions upon ingestion by said insect pest to inhibit a biological function within said insect and ii) non-TIC807 proteins that are insect inhibitory. These insect pests include those insect pests that pierce and then suck the phloem sap or cell contents as well as those that macerate the cells in the vicinity of the feeding zone and then take up the fluid that is released from the macerated cells through there proboscis. Insects targeted by the TIC807 proteins and other insect inhibitory agents described herein include various hemipteran, homopteran and heteropteran insects. Inhibition of insects such as *Lygus*, whiteflies, hoppers and aphids is specifically contemplated by use of TIC807 and other insect inhibitory agents as described herein.

VIII. Transgenic Plant Insect Control Methods

Transgenic plants of the present invention comprising polynucleotides encoding TIC807 or insecticidal fragments thereof can be used in methods of controlling insect infestations. Transgenic barley, corn, oat, rice, rye, sorghum, turf grass, sugarcane, wheat, alfalfa, banana, broccoli, bean, cabbage, canola, carrot, cassava, cauliflower, celery, citrus, cotton, a cucurbit, eucalyptus, flax, garlic, grape, onion, lettuce, pea, peanut, pepper, potato, poplar, pine, sunflower, safflower, soybean, strawberry, sugar beet, sweet potato, tobacco, tomato, ornamental, shrub, nut, chickpea, pigeonpea, millets, hops, and pasture grass plants can be used in these methods. Transgenic plants such as alfalfa, canola, cotton, lettuce and strawberry plants that are attacked by hemipteran insect pests inhibited by TIC807 proteins are specifically contemplated by this invention. Even more specifically contemplated by the present invention are transgenic cotton plants comprising polynucleotides encoding TIC807 or insecticidal fragments thereof that are protected from *Lygus* species insect infestation. Transgenic plants of the present invention are particularly effective for controlling species of insects that pierce and/or suck the fluids from the cells and tissues of plants, including but not limited to, plant bugs in the Miridae family such as western tarnished plant bugs (*Lygus hesperus* species), tarnished plant bugs (*Lygus lineolaris* species), and pale legume bugs (*Lygus elisus*) and stinkbugs (Pentatomidae family species).

Specific types of transgenic plants expressing TIC807 proteins that inhibit specific insect pests are contemplated by this invention. Transgenic cotton plants expressing TIC807 proteins that inhibit Hemipteran insects including *Lygus*, hoppers and aphids are specifically contemplated. Transgenic cotton plants that express the TIC807 protein of SEQ ID NO:5 are anticipated to inhibit *Lygus hesperus* or *Lygus lineolaris*. Transgenic alfalfa, canola, lettuce and strawberry plants that express the TIC807 protein of SEQ ID NO:5 and that inhibit *Lygus* are also specifically contemplated.

The transgenic plants expressing insect inhibitory amounts of the TIC807 proteins are first identified by any one of the methods described herein. Initial insect inhibition can be conducted in controlled environmental conditions (i.e., in enclosed growth chambers or green houses). Transgenic plants can also be subjected to insect infestation in field tests and compared against non-transgenic control plants. Typically, the non-transgenic control plants will include both plants treated with insecticides and untreated plants. Transgenic plant lines (i.e., transgenic plants derived from distinct transformation events comprising transgene insertions into different genomic locations) that display the best insect inhibitory activity are selected for potential development for use in a variety of different genetic backgrounds (i.e., genetically distinct cultivars, varieties, and/or hybrid germplasms). Methods of introgressing transgenes into distinct germplasms and producing seed lots that primarily comprise transgenic seed are known to those skilled in the art. For example, the transgene can be fixed in a homozygous state in a desired genetic background. Once the transgene fixed in that background, the homozygous transgenic plant can be used to produce transgenic seed of non-hybrid crops. Alternatively, the homozygous transgenic plant can be used as a pollen donor or recipient to produce transgenic seed of hybrid crops.

Specific types of transgenic plants expressing TIC807 proteins that inhibit specific insect pests are contemplated by this invention. Transgenic cotton plants expressing TIC807 proteins that inhibit hemipteran insects including *Lygus*, hoppers and aphids are specifically contemplated. Transgenic cotton plants that express the TIC807 protein of SEQ ID NO:5 are anticipated to inhibit *Lygus hesperus* or *Lygus lineolaris*. Transgenic alfalfa, canola, and strawberry plants that express the TIC807 protein of SEQ ID NO:5 and that inhibit *Lygus* are also specifically contemplated.

IX. Non-Transgenic Control Methods and Compositions

The TIC807 protein compositions disclosed herein will find particular utility as insect inhibitory agents for topical and/or systemic application to field crops, grasses, fruits and vegetables, and ornamental plants. More specifically, TIC807 can be used in compositions comprising an insect inhibitory amount of a TIC807 protein composition. In this regard, TIC807 protein compositions made up of TIC807 crystal protein preparations for *Bacillus thuringiensis* spores are particularly useful. The TIC807 protein composition can comprise the amino acid sequence of SEQ ID NO:5 or to an insect inhibitory protein of at least 250 amino acids that displays at least 70% sequence identity to a corresponding polypeptide sequence contained within SEQ ID NO:5.

The insect inhibitory composition can also comprise a *Bacillus thuringiensis* cell, or a culture of these cells, or a mixture of one or more *B. thuringiensis* cells which express one or more of the TIC807crystal proteins of the invention. In certain aspects it may be desirable to prepare compositions which contain a plurality of crystal proteins, either native or modified, for treatment of one or more types of susceptible insects.

The inventors contemplate that any formulation methods known to those of skill in the art may be employed using the proteins disclosed herein to prepare such insect inhibitory compositions. It may be desirable to formulate whole cell preparations, cell extracts, cell suspensions, cell homogenates, cell lysates, cell supernatants, cell filtrates, or cell pellets of a cell culture (preferably a bacterial cell culture such as a *Bacillus thuringiensis* culture) that expresses one or more TIC807 DNA segments to produce the encoded TIC807 protein(s) or peptide(s). The methods for preparing such formulations are known to those of skill in the art, and may include, e.g., desiccation, lyophilization, homogenization, extraction, filtration, centrifugation, sedimentation, or concentration of one or more cultures of bacterial cells, such as *Bacillus* SIC8091, SIC8092, SIC8093, and SIC8094 cells, which express the TIC807 peptide(s) of interest.

In one embodiment, the insect inhibitory composition comprises an oil flowable suspension comprising lysed or unlysed bacterial cells, spores, or crystals which contain one or more of the novel crystal proteins disclosed herein. Preferably the cells are *B. thuringiensis* cells, however, any such bacterial host cell expressing the novel nucleic acid segments disclosed herein and producing a crystal protein is contemplated to be useful, such as *Bacillus* spp., including *B. megaterium, B. subtilis; B. cereus, Escherichia* spp., including *E. coli*, and/or *Pseudomonas* spp., including *P. cepacia, P. aeruginosa*, and *P. fluorescens*. Alternatively, the oil flowable suspension may consist of a combination of one or more of the following compositions: lysed or unlysed bacterial cells, spores, crystals, and/or purified crystal proteins.

In a second embodiment, the insect inhibitory composition comprises a water dispersible granule or powder. This granule or powder may comprise lysed or unlysed bacterial cells, spores, or crystals which contain one or more of the novel crystal proteins disclosed herein. Preferred sources for these compositions include bacterial cells such as *B. thuringiensis* cells, however, bacteria of the genera *Bacillus, Escherichia*, and *Pseudomonas* which have been transformed with a DNA segment disclosed herein and expressing the crystal protein are also contemplated to be useful. Alternatively, the granule or powder may consist of a combination of one or more of the following compositions: lysed or unlysed bacterial cells, spores, crystals, and/or purified crystal proteins.

In a third important embodiment, the insect inhibitory composition comprises a wettable powder, spray, emulsion, colloid, aqueous or organic solution, dust, pellet, or collodial concentrate. Such a composition may contain either unlysed or lysed bacterial cells, spores, crystals, or cell extracts as described above, which contain one or more of the novel crystal proteins disclosed herein. Preferred bacterial cells are *B. thuringiensis* cells, however, bacteria such as *B. megaterium, B. subtilis, B. cereus, E. coli*, or *Pseudomonas* spp. cells transformed with a DNA segment disclosed herein and expressing the crystal protein are also contemplated to be useful. Such dry forms of the insecticidal compositions may be formulated to dissolve immediately upon wetting, or alternatively, dissolve in a controlled-release, sustained-release, or other time-dependent manner. Alternatively, such a composition may consist of a combination of one or more of the following compositions: lysed or unlysed bacterial cells, spores, crystals, and/or purified crystal proteins.

In a fourth embodiment, the insect inhibitory composition comprises an aqueous solution or suspension or cell culture of lysed or unlysed bacterial cells, spores, crystals, or a mixture of lysed or unlysed bacterial cells, spores, and/or crystals, such as those described above which contain one or more of the novel crystal proteins disclosed herein. Such aqueous solutions or suspensions may be provided as a concentrated stock solution which is diluted prior to application, or alternatively, as a diluted solution ready-to-apply.

For these methods involving application of bacterial cells, the cellular host containing the TIC807 protein gene(s) may be grown in any convenient nutrient medium, where the DNA construct provides a selective advantage, providing for a selective medium so that substantially all or all of the cells retain the B. thuringiensis gene. These cells may then be harvested in accordance with conventional ways. Alternatively, the cells can be treated prior to harvesting.

When the insecticidal compositions comprise B. thuringiensis cells, spores, and/or crystals containing the modified crystal protein(s) of interest, such compositions may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

Alternatively, the TIC807 proteins can be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the crystal protein and apply solutions, suspensions, or colloidal preparations of such crystals and/or spores as the active bioinsecticidal composition.

Regardless of the method of application, the amount of the active component(s) are applied at an insect inhibitory amount, which will vary depending on such factors as, for example, the specific hemipteran, homopteran, or heteropteran insects to be controlled, the specific plant or crop to be treated, the environmental conditions, and the method, rate, and quantity of application of the insect inhibitory composition.

The insect inhibitory compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, dessicated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

The insect inhibitory compositions of this invention are applied to the environment of the target hemipteran, homopteran, or heteropteran insect, typically onto the foliage of the plant or crop to be protected, by conventional methods, preferably by spraying. The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art.

The insect inhibitory composition of the invention may be employed in the method of the invention singly or in combination with other compounds, including and not limited to other pesticides. The method of the invention may also be used in conjunction with other treatments such as surfactants, detergents, polymers or time-release formulations. The insecticidal compositions of the present invention may be formulated for either systemic or topical use.

The concentration of insect inhibitory agent in the insect inhibitory composition which is used for environmental, systemic, or foliar application will vary widely depending upon the nature of the particular formulation, means of application, environmental conditions, and degree of insect inhibitory activity. Typically, the insect inhibitory agent in the composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the active ingredient by weight. Formulations which comprise intact bacterial cells will generally contain from about $10^4$ to about $10^{12}$ cells/mg of the composition.

The insect inhibitory formulation may be administered to a particular plant or target area in one or more applications as needed, with a typical field application rate per hectare ranging on the order of from about 1 g to about 1 kg, 2 kg, 5, kg, or more of active ingredient.

XI. Commodity Products

It is also contemplated that various commodity products may be obtained with the compositions and methods of this invention. Moreover, it is specifically contemplated that one or more advantages can be associated with the commodity products derived from this invention. It is anticipated that the use of the TIC807 insect inhibitory protein and associated methods can provide for commodity products with lowered pesticide residue levels. In certain instances, growers will be prompted to use fewer pesticides such as organophosphates, carbamates, neonicotinoid, and pyrethroid insecticides. Exposure of individuals who grow, harvest, process or otherwise come into contact with the commodity products of this invention to these pesticides is thus anticipated to be reduced. Reduced use of pesticides is also anticipated to provide for reduced costs of commodity product production, reduced levels of environmental contamination and reduced undesirable side effects on beneficial (non-target) insects and fauna. It is further contemplated that the use of this invention will provide for commodity products with lower costs of production due to factors including, but not limited to, increased yield and/or decreased insecticide usage.

XII. Methods of Using TIC807 Insect Inhibitory Proteins in Combination with Other Insect Inhibitory Agents Several methods by which increased resistance to a specific insect pest or broader resistance to several classes of insect pests are contemplated by this invention. Both methods entail contacting the insect pest(s) with a TIC807 protein in combination with a distinct insect inhibitory agent. This distinct insect inhibitory agent can inhibit the same hemipteran insect pests inhibited by the TIC807 to provide for a decreased incidence of hemipteran insect resistance to the TIC807 protein or other hemipteran insect inhibitory agent. Alternatively, the distinct insect inhibitory agent can inhibit an insect that is not inhibited by TIC807 to expand the spectrum of insect inhibition obtained.

The potential for insects to develop resistance to certain insecticides is well documented. Most insect resistance management strategies using genetically modified crops expressing insect inhibitory agents rely on the use of refuge areas that are comprised of crop plants that lack the insect inhibitory gene. In theory, the refuge provides a region in which non-resistant insect populations harboring non-resistant genetic alleles are maintained, lowering the potential for resistance to develop within the insect population. However, the refuge strategy suffers from several short-comings. First, the growers must accept reduced yields on the acreage planted with the insect inhibitory gene. Second, it is not clear that refuges will effectively control dominant resistance alleles that can arise in the insect population.

An alternative insect resistance management strategy can employ transgenic crops that express two distinct insect inhibitory agents that operate through different modes of action. In this case, any insects with resistance to either one of the insect inhibitory agents will be controlled by the other insect inhibitory agent, thus reducing the chances of resistance developing in the insect population.

In addition, a single crop may be subject to destruction by several different classes of insect pests operating at the same time in the field. For example, a cotton plant can be attacked by both Hemipteran pests, such as *Lygus*, and Lepidopteran pests such as *Spodoptera exigua* (beet armyworm), *Heliothis zea* (cotton bollworm) and/or *Helicoverpa armigera* (armyworm) in the course of a growing season. Expression of distinct inhibitory agents which are active to each of these pests would provide greater protection to the cotton plant and would increase the yield per acre due to a reduction of loss caused by the insect pests.

A first group of insect inhibitory agents that can be used in combination with a TIC807 protein for insect resistance management or expanded insect inhibitory spectrum comprise ribonucleotide sequences that function upon ingestion by said insect pest to inhibit a biological function within said insect pest. Specific nucleotide sequences selected from the sequences native to the cells of a particular pest that are involved in an essential biological pathway can be expressed in a cell in such a way as to result in the formation of a double stranded RNA, or even a stabilized double stranded RNA. By inhibiting the essential gene product of the target insect pest with the ribonucleotide, the organism fails to develop and eventually dies. The use of such ribonucleotide sequences to control insect pests such as *Lygus* is described in United States Patent Application Publication No. 20060021087. Essential insect genes that provide essential biological function that include, but are not limited to, muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis are targeted for inhibition. Insect genes that can be inhibited include, but are not limited to, genes encoding a V-ATPase protein, a ubiquitin protein, a polyglacturonase protein, a pectinase protein, a GABA neurotransmitter transporter protein, a EFI alpha protein, a cytochrome P-450 mono-oxygenase protein, a cuticle protein precursor protein, a CHD3 protein, and a 20S proteasome protein. The ribonucleotide based insect control agent may also comprise sequences directed against multiple insect target genes. For control of *Lygus*, inhibitory ribonucleotides directed against SEQ ID NO:24 through SEQ ID NO:39 or combinations of inhibitory ribonucleotides directed against SEQ ID NO:24 through SEQ ID NO:39 are specifically contemplated. The use of SEQ ID NO:24 through SEQ ID NO:39 in the control of insects is disclosed in United States Patent Application Publication No. 20060021087. When multiple insect genes are targeted for suppression, a polycistronic DNA element can be fabricated as illustrated and disclosed in Fillatti, U.S. Application Publication No. 2004-0029283 A1.

A variety of methods can be used to produce inhibitory ribonucleotides directed against a target pest in a transgenic plant. In general, the inhibitory dsRNA and the portion of the insect target gene share at least from about 80% sequence identity, or from about 90% sequence identity, or from about 95% sequence identity, or from about 99% sequence identity, or even about 100% sequence identity. Alternatively, the duplex region of the RNA may be defined functionally as a nucleotide sequence that is capable of hybridizing with a portion of the target gene transcript. A less than full length sequence exhibiting a greater homology compensates for a longer less homologous sequence. The length of the identical nucleotide sequences may be at least 25, 50, 100, 200, 300, 400, 500 or 1000 bases. Normally, a sequence of greater than 20-100 nucleotides should be used, though a sequence of greater than about 200-300 nucleotides would be preferred, and a sequence of greater than 500-1000 nucleotides would be especially preferred depending on the size of the target gene.

In another embodiment, the insect inhibitory ribonucleotide can be produced by an inverted repeat separated by a "spacer sequence". The spacer sequence may be a region comprising any sequence of nucleotides that facilitates secondary structure formation between each repeat, where this is required. In one embodiment of the present invention, the spacer sequence is part of the sense or antisense coding sequence for mRNA. The spacer sequence may alternatively comprise any combination of nucleotides or homologues thereof that are capable of being linked covalently to a nucleic acid molecule. The spacer sequence may comprise a sequence of nucleotides of at least about 10-100 nucleotides in length, or alternatively at least about 100-200 nucleotides in length, at least about 200-400 nucleotides in length, or at least about 400-500 nucleotides in length.

A transgene sequence for producing a dsRNA may comprise a promoter that is operatively linked to an intron encoding sequence and a hairpin RNA derived from a sequence in the target gene (Miki and Shimamoto, Plant Cell Physiol. April 2004; 45(4):490-495). Alternatively, a transgene sequence for producing an siRNA may comprise an RNA pol III promoter operably linked to a hairpin RNA (Lu et al., Nucleic Acids Res. Dec. 2, 2004; 32(21):e171). The hairpin RNA may comprise a 5' sequence of roughly 19-24 nucleotides of sense strand target gene sequence followed by a spacer nucleotide of about 8-10 nucleotides followed by a sequence of roughly 19-24 nucleotides of antisense sequence that is capable of base pairing with the preceding sense strand sequence. However, hairpin RNA-expressing plant transgenes containing sense/anti-sense arms ranging from 98 to 853 nucleotides can also be used (Wesley et al., Plant J. 2001, 27(6):581-90). Vectors and methods for transgene-mediated expression of hairpin RNAs are disclosed in U.S. Patent Application Nos. 20050164394, 20050160490, and 20040231016.

A first group of insect inhibitory agents that can be used in combination with a TIC807 protein for insect resistance management or expanded insect inhibitory spectrum comprise insect inhibitory proteins other than TIC807. A wide variety of insect inhibitory proteins derived from *B. thuringiensis*, *Photorhabdus* sp., and/or *Xenorhabdus* sp. can be used.

For the control of sucking piercing insects such as *Lygus*, several non-TIC807 insect inhibitory proteins can be combined with TIC807 expression in planta for greater control and/or resistance management. Such molecules expressed inplanta along with TIC807 may include ET29, ET37, TIC809, TIC810, TIC812, TIC127, TIC128 (PCT US 2006/033867), AXMI-027, AXMI-036, and AXMI-038 (WO 06/107761), AXMI-018, AXMI-020, and AXMI-021 (WO 06/083891), AXMI-010 (WO 05/038032), AXMI-003 (WO 05/021585), AXMI-008 (US 2004/0250311), AXMI-006 (US 2004/0216186), AXMI-007 (US 2004/0210965), AXMI-009 (US 2004/0210964), AXMI-014 (US 2004/0197917), AXMI-004 (US 2004/0197916), AXMI-028 and AXMI-029 (WO 06/119457) and AXMI-007, AXMI-008, AXMI-0080rf2, AXMI-009, AXMI-014 and AXMI-004 (WO 04/074462). Presenting the combination of the inhibitory protein molecules, TIC809 (presented as SEQ ID NO: 10) and TIC810 (presented as SEQ ID NO: 12) has been previously shown to be inhibitory to the Western Tarnished Plant Bug (WTPB), *Lygus hesperus* Knight in bioassay (PCT US 2006/033867). The fusion proteins of TIC809 and TIC810, TIC 127 (presented as SEQ ID NO:14) and TIC 128 (presented as SEQ ID NO:16) may also be active against *Lygus*. The polynucleotide encoding TIC127 is comprised of the nucleic acid molecule encoding TIC809 linked to the nucleic acid molecule encoding TIC810 by a polylinker nucleotide sequence (presented as SEQ ID NO:17) encoding the amino acid linker presented as SEQ ID NO:18. The polynucleotide encoding TIC128 is comprised of the nucleic acid molecule encoding TIC810 linked to the nucleic acid molecule encoding TIC809 by a polylinker nucleotide sequence (presented as SEQ ID NO:17) encoding the amino acid linker presented as SEQ ID NO:18. Expression of TIC807 in combination with TIC127 or TIC128 may provide enhanced control of *Lygus*. Dicot plants such as cotton could be transformed with plant expression constructs containing dicot-optimized nucleotide sequences encoding TIC807 (presented as SEQ ID NO:6) along with TIC809 (presented as SEQ ID NO:9) and TIC810 (presented as SEQ ID NO:11), or TIC127 (presented as SEQ ID NO:13), or TIC128 (presented as SEQ ID NO:15) to provide enhanced resistance to *Lygus* or inhibition of additional species contained within the genus, *Lygus*.

For control of Lepidopteran pests, combinations of TIC807 proteins with Lepidopteran-active proteins such as Cry1A proteins (U.S. Pat. No. 5,880,275), Cry1B (U.S. patent application Ser. No. 10/525,318), Cry1C (U.S. Pat. No. 6,033,874), Cry1F, Cry1A/F chimeras (U.S. Pat. Nos. 7,070,982; 6,962,705; and 6,713,063), and a Cry2Ab protein (U.S. Pat. No. 7,064,249) are specifically contemplated.

DNA sequences encoding TIC807 protein molecules and other insect inhibitory agents such as double stranded RNA molecules and/or non-TIC807 proteins can be combined in a single plant either through direct transformation, by breeding, or a combination thereof. Multiple transcription units comprising a promoter and an insect inhibitory agent encoding region can be introduced on the same plant transformation vector or on different plant transformation vectors. When the two insect inhibitory agents are proteins, the coding regions for each may be separated by a protease sensitive linker or even a self-processing protease cleavage site (see U.S. Pat. No. 5,846,767). When the insect inhibitory agents are each introduced into distinct transgenic plants, those plants may be crossed to obtain a plant containing all of the insect inhibitory agent encoding transgenes.

It is further anticipated that the combination of TIC807 protein molecules and other insect inhibitory agents such as double stranded RNA molecules and/or non-TIC807 proteins can result in unexpected synergistic insect inhibitory effects that are not observed with either the TIC807 insecticidal protein alone, the insect inhibitory ribonucleotide alone, or the non-TIC807 insect inhibitory protein alone. Synergistic effects include but are not limited to: i) quantitative changes in $LC_{50}$ $EC_{50}$, $IC_{50}$, percent mortality, or percent stunting values and ii) qualitative changes in the spectrum of insect inhibition (i.e., Hemipteran, Homopteran, and Lepidopteran insects inhibition) that does not reflect the simple combination of the spectrum exhibited by each insect inhibitory agent alone (i.e., the combination of Hemipteran insect inhibition provided by one agent and Lepidopteran insect inhibition provided by another agent). A non-limiting example of a quantitative synergistic effect is a decrease in any $LC_{50}$, $EC_{50}$, and/or $IC_{50}$, value or an increase in percent mortality, or percent stunting values observed in a combination that is more than additive. A non-limiting example of a qualitative synergistic effect is control of an insect pest with the combination of insect agents that is not observed with either member alone. In this instance, the new insect pest controlled by the combination may be an insect pest within an order of insects (i.e., Hemipterans) where the insect inhibitory agents only inhibit other insect pests within that order of insects when used alone.

XIII. Isolated TIC807 Proteins and Biological Equivalents

Isolated TIC807 proteins are also provided herein. In one embodiment, the TIC807 proteins comprise proteins of at least 250 amino acids that have at least 70% sequence identity to SEQ ID NO:5 and display insect inhibitory activity. The biologically functional equivalent peptides, polypeptides, and proteins contemplated herein should possess about 70% or greater sequence identity, preferably about 85% or greater sequence identity, and most preferably about 90% to 95% or greater sequence identity, to the sequence of, or corresponding moiety within, the TIC807 polypeptide sequence. In certain embodiments of the invention, biologically functional equivalent peptides, polypeptides, and proteins possessing about 80% or greater sequence identity, preferably about 85%, 86%, 87%, 88%, 89% or greater sequence identity, and most preferably about 90%, 91%, 92%, 93%, 94%, 95%, 96%, 97%, 98%, 99% or greater sequence identity, to the sequence of TIC807 (SEQ ID NO:5)

Peptides, polypeptides, and proteins biologically functionally equivalent to TIC807 include, but are not limited to, amino acid sequences containing conservative amino acid substitutions in the TIC807 protein sequences. An example of TIC807 proteins that can be substituted to obtain biological equivalents include, but are not limited to, the TIC807 protein sequence (SEQ ID NO:5). In such amino acid sequences, one or more amino acids in the sequence is (are) substituted with another amino acid(s), the charge and polarity of which is similar to that of the native amino acid, i.e., a conservative amino acid substitution, resulting in a silent change.

Substitutes for an amino acid within the TIC807 polypeptide sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; (4) neutral non-polar (hydrophobic) amino acids such as alanine, leucine, isoleucine, valine, proline, phenylalanine, tryptophan, and methionine.

Conservative amino acid changes within the TIC807 polypeptide sequence can be made by substituting one amino acid within one of these groups with another amino acid within the same group. Biologically functional equivalents of TIC807 can have 10 or fewer conservative amino acid changes, more preferably seven or fewer conservative amino acid changes, and most preferably five or fewer conservative amino acid changes. The encoding nucleotide sequence (gene, plasmid DNA, cDNA, or synthetic DNA) will thus have corresponding base substitutions, permitting it to encode biologically functional equivalent forms of TIC807.

As indicated, modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated TIC807 proteins are contemplated to be useful for increasing the insect inhibitory activity of the protein, and consequently increasing the insect inhibitory activity and/or expression of the recombinant transgene in a plant cell. The amino acid changes may be achieved by changing the codons of the DNA sequence, according to the codons given in Table 1.

TABLE 1

| Amino Acids | Amino Acid Codes | Codons |
|---|---|---|
| Alanine | Ala (A) | GCA GCC GCG GCU |
| Cysteine | Cys (C) | UGC UGU |
| Aspartic acid | Asp (D) | GAC GAU |
| Glutamic acid | Glu (E) | GAA GAG |

TABLE 1-continued

| Amino Acids | Amino Acid Codes | Codons |
|---|---|---|
| Phenylalanine | Phe (F) | UUC UUU |
| Glycine | Gly (G) | GGA GGC GGG GGU |
| Histidine | His (H) | CAC CAU |
| Isoleucine | Ile (I) | AUA AUC AUU |
| Lysine | Lys (K) | AAA AAG |
| Leucine | Leu (L) | UUA UUG CUA CUC CUG CUU |
| Methionine | Met (M) | AUG |
| Asparagine | Asn (N) | AAC AAU |
| Proline | Pro (P) | CCA CCC CCG CCU |
| Glutamine | Gln (Q) | CAA CAG |
| Arginine | Arg (R) | AGA AGG CGA CGC CGG CGU |
| Serine | Ser (S) | AGC AGU UCA UCC UCG UCU |
| Threonine | Thr (T) | ACA ACC ACG ACU |
| Valine | Val (V) | GUA GUC GUG GUU |
| Tryptophan | Trp (W) | UGG |
| Tyrosine | Tyr (Y) | UAC UAU |

For example, certain amino acids may be substituted for other amino acids in a protein structure without appreciable loss of biochemical or biological activity. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, J Mol Biol. 157(1): 105-32, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, Ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within .+2 is preferred, those which are within +1 are particularly preferred, and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Non-Conservative Substitutions in the TIC807 Polypeptides

It is further recognized that non-conservative substitutions in TIC807 polypeptide sequences can be made to obtain TIC807 polypeptides that are the functional biological equivalents of the TIC807 polypeptides disclosed herein. In these instances, the non-conservative substitutions can simply be tested for inhibition of fungal growth to identify non-conservative substitutions that provide for functional biological equivalents of a given TIC807 polypeptide.

Fragments and Variants of TIC807

While the insect inhibitory polypeptide of the present invention preferably comprise a TIC807 protein sequence, fragments and variants of this sequence possessing the same or similar insect inhibitory activity as that of this insect inhibitory protein are also encompassed by the present invention. Thus contiguous sequences of at least 250 or more amino acids in an TIC807 protein with insect inhibitory activity are anticipated by this invention. Fragments or variants of TIC807 with insect inhibitory activity that are anticipated by this invention can also comprise amino acid substitutions, deletions, insertions or additions in an TIC807 protein sequence.

The insect inhibitory polypeptide of the present invention preferably comprises the TIC807 protein sequence (SEQ ID NO:5), fragments and variants of this sequence possessing the same or similar insect inhibitory activity as that of this particular TIC807 protein are also encompassed by the present invention are anticipated by this invention. Thus contiguous sequences of at least 250 or more amino acids in SEQ ID NO:5 with insect inhibitory activity are anticipated by this invention. The insect inhibitory TIC807 fragments can also comprise fragments with at least 260, at least 270, at least 280, at least 290, or at least 300 amino acid residues of the 309 amino acid TIC807 sequence of SEQ ID NO:5. The fragments or variants with insect inhibitory activity that are anticipated by this invention can also comprise amino acid substitutions, deletions, insertions or additions of the sequence shown in SEQ ID NO:5.

Fragments of the mature TIC807 protein can be truncated forms wherein one or more amino acids are deleted from the N-terminal end, C-terminal end, the middle of the protein, or combinations thereof with insect inhibitory activity are also anticipated by this invention. These fragments can be naturally occurring or synthetic mutants of TIC807, and retain the insect inhibitory activity of TIC807. A preferred TIC807 protein that can be used to obtain truncated derivatives with insect inhibitory activity is the TIC807 protein of SEQ ID NO:5.

Variants of TIC807 include forms wherein one or more amino acids has (have) been inserted into the natural sequence. These variants can also be naturally occurring or synthetic mutants of TIC807, and retain the insect inhibitory activity of TIC807.

Combinations of the foregoing, i.e., forms of the insect inhibitory polypeptide containing both amino acid deletions and additions, are also encompassed by the present invention. Amino acid substitutions can also be present therein as well.

The fragments and variants of TIC807 encompassed by the present invention should preferably possess about 70-75% or greater sequence identity, more preferably about 80%, 85%, 88% or greater sequence identity, and most preferably about 90% to 95% or greater amino acid sequence identity, to the corresponding regions of the mature TIC807 protein having the corresponding amino acid sequences shown in SEQ ID NO:5.

Use of Structure Function Relationships to Design Insect Inhibitory TIC807 Variants This invention also contemplates the use of structure function relationships to design additional insect inhibitory TIC807 protein variants. It is first contemplated that a structure could be obtained by crystallographic analysis of TIC807 crystals. Such structures are anticipated to reveal domains of the TIC807 protein involved in insect receptor binding, pore formation in the insect gut, multimerization with TIC807, protease sensitivity and/or protease resistance that contribute to the insect inhibitory activity of TIC807.

It is further anticipated that comparisons between TIC807 and other related proteins may permit extrapolation of protein domains that contribute to the insecticidal activity of TIC807 proteins. In this regard, it is noted that TIC807 has some similarity to a family of MTX-like proteins. This Mtx-like family of proteins is named after the *Bacillus* sphericus proteins Mtx2 (Thanabalu and Porter, Gene. 170(1):85, 1996; NCBI Accession No. 2211294A) and Mtx3 (Liu et al., Appl Environ Microbiol. 62(6):2174, 1996; NCBI Accession No. AAB36661) and includes Cry15Aa (SEQ ID NO:41), Cry33Aa (NCBI Accession No. AAL26871), Cry23Aa (NCBI Accession No. AAF76375), Cry38Aa (NCBI Accession No. AAK64559), CryC35 (NCBI Accession No. CAA63374), the 40KD protein (NCBI Accession No. AAA22332), and CryNT32 (NCBI Accession No. AAL26870). It is also believed that TIC807 is distantly related to the aerolysin family of proteins that include cryET33 (WO 97/17600), and TIC901 (U.S. Patent Application No. 20060191034). Aerolysins are a group of proteins that multimerize and form pores in membranes and are known toxins (Parker et al., Mol. Microbiol. 19(2):205, 1996). In particular, crystallographic structure determinations indicate that beta-sheet domains of aerolysins are involved in forming membrane pores (Rossjohn et al., J Struct Biol. 121(2):92, 1998). Domains of TIC807 proteins could be swapped with similar domains from other MTX-like or Aerolysin family proteins to identify domains involved in insect receptor binding, pore formation in the insect gut, multimerization with TIC807, protease sensitivity and/or protease resistance that contribute to the insect inhibitory activity of TIC807. Data from the domain swapping experiments can be compared and otherwise extrapolated to structural data for Mtx-like protein family members to elucidate domains that provide for different insecticidal activities, improved insecticidal activities, improved binding characteristics, improved pore forming capabilities.

Having identified certain protein domains of the TIC807 proteins that provide for insect inhibitory properties of the TIC807 protein (i.e., insect receptor binding, pore formation in the insect gut, multimerization with TIC807, protease sensitivity and/or protease resistance), it is further anticipated that these regions can be more extensively mutagenized. Once mutagenized, variant TIC807 proteins can be subjected to either biochemical (i.e., insect receptor binding, pore formation in the insect gut, multimerization with TIC807, protease sensitivity and/or protease resistance) or biological assays (i.e., insect inhibition assays) to identify those variants that confer improved biochemical and/or insect inhibitory activities. Additional iterative rounds of mutagenesis and assay of those identified variants is also contemplated. Various procedures for the molecular evolution of isolated proteins that are either known to those skilled in the art (Stemmer, W., Proc. Natl. Acad. Sci. USA 91: 10747, 1994; Yuan et al., Microbiol. Mol. Biol. Rev. 69(3):373, 2005) or are provided by other entirely distinct methods can be employed to generate the TIC807 protein variants.

Isolated TIC807 Proteins of at Least 9 Amino Acids

In other embodiments of this invention, isolated proteins that comprise a polypeptide sequence of at least 9 amino acids in length that is contained within SEQ ID NO:5 are provided. At least two distinct uses for TIC807 peptide sequences of at least 9 amino acids are contemplated.

First, it is contemplated that TIC807 peptide sequences of at least 9 amino acids can be substituted into distinct protein sequences to confer all or a subset of the insect inhibitory activities of a TIC807 protein on the resultant TIC807-peptide substituted protein. Insect inhibitory activities conferred by the TIC807 peptide sequences can comprise inhibition of a hemipteran pest including, but not limited to, *Lygus*. Without being limited by theory, it is believed that TIC807 peptide sequences of at least 9 amino acids can provide: 1) improved crystal formation, 2) improved protein stability or reduced protease degradation, 3) improved insect membrane receptor recognition and binding, 4) improved oligomerization or channel formation in the insect midgut endothelium, and 5) improved insecticidal activity or insecticidal specificity due to any or all of the reasons stated above when inserted into another protein. Larger TIC807 peptide sequences of at least 12, at least 16, at least 32, at least 50 or at least 100 amino acid residues from SEQ ID NO:5 can also be substituted into distinct protein sequences to obtain insect inhibitory TIC807-peptide substituted proteins.

TIC807-peptide substituted protein can be synthesized by techniques including, but not limited to, site-specific mutagenesis (Kunkel, T. A. et al. Meth. Enzymol. 154: 367, 1987), DNA shuffling (Stemmer, W., Proc. Natl. Acad. Sci. USA 91: 10747, 1994), PCR.™. overlap extension (Horton et al., Gene 77: 61, 1989), any of the protein molecular evolution methods (Yuan et al., Microbiol. Mol. Biol. Rev. 69(3):373, 2005), direct synthesis, combinations of these methods, or by other entirely distinct methods that provide for TIC807-peptide substituted proteins. In particular, TIC807-substituted proteins derived by insertion or substitution of TIC807 peptide sequences of at least 9 amino acids into insect inhibitory proteins derived from *Bacillus thuringiensis* are contemplated. Exemplary *Bacillus thuringiensis* proteins that can be substituted with TIC807 polypeptides to obtain TIC807-substituted proteins with insect inhibitory activity include, but are not limited to, Cry15Aa1 (Brown & Whiteley, 1992, J Bacteriol 174 549-557; SEQ ID NO:41), CryET29 (U.S. Pat. No. 6,093,695), Cyt1Ba1 (U.S. Pat. No. 5,723,440), *Bacillus thuringiensis* israelensis Cyt toxins (U.S. Pat. No. 5,885,963), and distinct *Lygus* active *Bacillus thuringiensis* crystal proteins AXMI-027, AXMI-036 and AXMI-038 disclosed in U.S. Patent Application Publication No. 20060242732. Other proteins that can be substituted with TIC807 polypeptides to obtain TIC807-substituted proteins with insect inhibitory activity include, but are not limited to, the Mtx2 (Thanabalu and Porter, Gene. 170(1):85, 1996; NCBI Accession No. 2211294A), Mtx3 (Liu et al., Appl Environ Microbiol. 62(6): 2174, 1996; NCBI Accession No. AAB36661), Cry15Aa (SEQ ID NO:41), Cry33Aa (NCBI Accession No. AAL26871), Cry23Aa (NCBI Accession No. AAF76375), Cry38Aa (NCBI Accession No. AAK64559), CryC35 (NCBI Accession No. CAA63374), the 40KD protein (NCBI Accession No. AAA22332), CryNT32 (NCBI Accession No. AAL26870), cryET33 (WO 97/17600), and TIC901 (U.S. Patent Application Publication No. 20060191034).

It is also contemplated that isolated TIC807 proteins of between about 250 and about 309 amino acids can also be used for antibody production or insect inhibition. These isolated TIC807 polypeptide sequences of the invention have at least about 70%, at least about 90%, at least about 95% or 100% sequence identity to a corresponding polypeptide sequence contained within SEQ ID NO:5. These TIC807 proteins can further comprise a covalently linked indicator reagent, an amino acid spacer, an amino acid linker, a signal sequence, a chloroplast transit peptide sequence, a vacuolar targeting sequence, or a stop transfer sequence.

It is also contemplated that isolated TIC807 peptide sequences of at least 9 contiguous amino acids of SEQ ID NO:5 can be used as immunogens or epitopes to prepare antibodies that recognize TIC807 proteins. Such antibodies are useful for detecting TIC807 proteins in transgenic plants, in commodity products derived from transgenic plants, in microorganisms or in recombinant DNA expression libraries that contain cloned TIC807 sequences. The TIC807 polypeptides can be at least 9, at least 12, at least 16, or at least 32 amino acids in length. When the TIC807 peptide sequence is at least 32 amino acids in length it has at least about 80%, 90%, or 95% sequence identity to a corresponding polypeptide sequence contained within SEQ ID NO:5. The peptides can be linked to a carrier protein such as KLH or albumin to facilitate antibody production.

The identification of TIC807 protein immunodominant epitopes, and/or their functional equivalents, suitable for use in vaccines is a relatively straightforward matter. For example, one may employ the methods of Hopp, as taught in U.S. Pat. No. 4,554,101, which teaches the identification and preparation of epitopes from amino acid sequences on the basis of hydrophilicity. The methods described in several other papers, and software programs based thereon, can also be used to identify epitopic core sequences (see, for example, U.S. Pat. No. 4,554,101). The amino acid sequence of these "epitopic core sequences" may then be readily incorporated into peptides, either through the application of peptide synthesis or recombinant DNA technology.

Preferred TIC807 peptides for use in accordance with the present invention will generally be on the order of about 9 to about 20 amino acids in length, and more preferably about 9 to about 15 amino acids in length. It is proposed that shorter antigenic TIC807 protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to TIC807 proteins, and in particular to TIC807-related sequences. These epitope core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the TIC807 protein-directed antibodies disclosed herein. Additionally or alternatively, an epitopic core sequence is one that will elicit antibodies that are cross-reactive with antibodies directed against the peptide compositions of the present invention. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 9 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

XIV. TIC807 Antibody Compositions and Methods of Making Antibodies

In particular embodiments, the inventors contemplate the use of antibodies, either monoclonal or polyclonal which bind to the TIC807 proteins disclosed herein. Means for preparing and characterizing antibodies are well known in the art (see, e.g., Using Antibodies: A Laboratory Manual, Cold Spring Harbor Laboratory, 1999). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or protein immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a peptide, polypeptide, or protein to a carrier protein are well known in the art and include using glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

Monoclonal antibodies (mAbs) may be readily prepared through use of well-known techniques, such as those exemplified in U.S. Pat. No. 4,196,265. Typically, this technique involves immunizing a suitable animal with a selected immunogen composition, e.g., a purified or partially purified antifungal protein, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages but mice are preferred, with the BALB/c mouse being most preferred as this is most routinely used and generally gives a higher percentage of stable fusions.

Also contemplated are methods of genetic immunization to obtain either monoclonal or polyclonal antibodies which bind to the TIC807 proteins disclosed herein. In these methods, the gene encoding the TIC807 protein is operably linked to a promoter that is active in mammalian cells. Isolated plasmid DNA comprising the mammalian cell expression cassette comprising the TIC807 encoding protein is then directly injected into the animal to elicit an immune response to the encoded TIC807 protein. Animals that can be used as injection hosts for genetic immunization include, but are not limited to, mice, rats, rabbits, goats, cows, or horses. Although a variety of injection regimens can be used, one exemplary regimen would comprise injection of plasmid DNA dissolved in phosphate-buffered saline or other suitable buffer at a concentration of approximately 1-2 mg plasmid DNA/ml and at a dose of about 100 ug/injection/animal (i.e., for a mouse, rat or rabbit). About 3-4 injections can be made in each animal in two week intervals. Genetic immunization is described in Chambers and Johnston, Nature Biotechnol. (21): 1088, 2003). Contract research organizations also conduct genetic immunization experiments to obtain antibodies (QED Bioscience Inc., San Diego, Calif., USA).

Examples of useful mammalian expression cassettes that can be used for genetic immunization include, but are not limited to, the pcDNA3.1 vector (Invitrogen, Carlsbad, Calif., USA) that provides a CMV promoter for expression of operably linked genes or the pRc/RSV vector (Invitrogen, Carlsbad, Calif., USA). In cases where high levels of antigen expression is cytotoxic, a weaker promoter, such as the SV40 promoter, can be used to express the antigen. It is anticipated that either the native TIC807 gene (SEQ ID NO:4) or the synthetic TIC807 gene (SEQ ID NO:6) can be operably linked to promoters and polyadenylation elements that are active in mammalian cells to obtain plasmids suitable for genetic immunization. However, the design and synthesis of other TIC807 encoding sequences for expression in mammalian hosts by backtranslation of the TIC807 amino acid sequence (SEQ ID NO:5) is also contemplated. Mammalian expression vectors that further comprise signal peptide sequences that provide for extracellular secretion and/or transmembrane insertion of operably linked sequences encoding TIC807 proteins are also contemplated.

XV. TIC807 Protein Screening and Detection Kits

The present invention contemplates methods and kits for screening samples suspected of containing TIC807 proteins or TIC807 protein-related polypeptides, or cells producing such polypeptides. In the particular embodiments contemplated herein, the methods and kits detect the TIC807 protein. A kit may contain one or more antibodies of the present invention, and may also contain reagent(s) for detecting an interaction between a sample and an antibody of the present invention. The provided reagent(s) can be radio-, spectrophotometrically-, fluorescently- or enzymatically-labeled. The provided reagents may include a substrate that is converted to a product that can be detected by spectrophotometry, luminometry, or fluorescence. The kit can contain a known radiolabeled or hapten-labeled agent capable of binding or interacting with an antibody of the present invention.

The reagent(s) of the kit may be provided as a liquid solution, attached to a solid support or as a dried powder. Preferably, when the reagent(s) are provided in a liquid solution, the liquid solution is an aqueous solution. Preferably, when the reagent(s) provided are attached to a solid support, the solid support can be chromatograph media, a test plate having a plurality of wells, or a microscope slide. When the reagent(s) provided are a dry powder, the powder can be reconstituted by the addition of a suitable solvent, that may be provided.

In still further embodiments, the present invention concerns immunodetection methods and associated kits. It is proposed that the TIC807 proteins or peptides of the present invention may be employed to detect antibodies having reactivity therewith, or, alternatively, antibodies prepared in accordance with the present invention, may be employed to detect TIC807 proteins or TIC807 protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a TIC807 protein or peptide or a TIC807 protein-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of TIC807 proteins or related peptides and/or antibodies in a sample. Samples may include cells, cell supernatants, cell suspensions, cell extracts, enzyme fractions, protein extracts, or other cell-free compositions suspected of containing TIC807 proteins or peptides. Generally speaking, kits in accordance with the present invention will include a suitable TIC807 protein, peptide or an antibody directed against such a protein or peptide, together with an immunodetection reagent for detecting antibody/antigen complexes, instructions for the use of these materials, and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

EXAMPLES

The following disclosed embodiments are merely representative of the invention, which may be embodied in various forms. Thus, specific structural and functional details disclosed herein are not to be interpreted as limiting.

Example 1

Identification of *Bacillus thuringiensis* Strain EG2934

This example describes *Bacillus thuringiensis* strain EG2934 and crystal proteins derived from this strain

*Bacillus thuringiensis* strains are well known for their ability to produce parasporal crystals that contain proteins with diverse insecticidal activities against Lepidopteran, Coleopteran, and Dipteran insect species. These parasporal crystals exhibit a variety of geometric shapes when viewed by phase-contrast microscopy and have been described as irregular, cuboidal, rod-shaped, rhomboidal, bipyramidal, et cetera. *B. thuringiensis* strains exhibiting Lepidopteran toxic activity appear to be more common than *B. thuringiensis* strains exhibiting toxicity to other insect species. Parasporal crystals exhibiting a bipyramidal shape are frequently associated with Lepidopteran toxic *B. thuringiensis* isolates. This bipyramidal crystal structure-function relationship with Lepidopteran activity provides an advantage when screening uncharacterized *B. thuringiensis* strains, allowing a rapid selection of strains that may exhibit insecticidal activity directed to insects other than Lepidopteran species. Strain EG2934 was selected on this basis as it appeared when viewed by phase-contrast microscopy to contain well defined crystals lacking a bipyramidal structure. In order to establish which crystal proteins produced by this strain possessed insecticidal activity, the genes encoding these proteins were cloned and expressed in a well-characterized toxin-free and acrystalliferous *B. thuringiensis* host strain. Four crystal proteins, ranging in size from approximately 35 kilodaltons (kDa) to approximately 120 kDa were identified in crystal preparations produced by *B. thuringiensis* strain EG2934. As a matter of routine screening these proteins were submitted for testing against known plant insect pests for toxicity. One protein from *B. thuringiensis* strain EG2934, designated as TIC807, was found to be toxic to the piercing-sucking insects, *Lygus hesperus* and *Lygus lineolaris*.

Example 2

Characterization of Crystal Proteins Produced by the *B. thuringiensis* Strain EG2934

This example illustrates the characterization of crystal proteins isolated from the *B. thuringiensis* strain EG2934 and the subsequent initial characterization of the *Lygus* active toxin protein, TIC807.

*B. thuringiensis* strain EG2934 was grown at 25 to 28 degrees Celsius in C2 sporulation medium (Donovan et al., Mol. Gen. Gent. 214: 365-372, 1988) for 3 to 4 days or until fully sporulated and lysed. Spores and crystals were collected by centrifugation and resuspended in wash buffer (10 mM Tris-HCl, 0.1 mMr EDTA, 0.005 percent Triton X-100, pH 6.8) and collected again by centrifugation. The spore-crystal pellets were resuspended in wash buffer at one tenth the original culture volume. Crystal proteins in the 10× concentrates were analyzed by SDS polyacrylamide gel electrophoresis (SDS-PAGE). Protein concentrations were determined by densitometry using bovine serum albumin (BSA) as a standard.

*B. thuringiensis* strain EG2934 produces crystal proteins of approximately 120, 110, 65 and 35 kilodaltons (kDA) upon sporulation. Proteins from EG2934 were resolved by SDS-PAGE. After electrophoresis, the proteins were transferred to a PVDF membrane (BioRad, Hercules, Calif.) following standard western blotting procedures. After transfer, the proteins bound to each membrane were subjected to N-terminal sequencing, using standard automated Edman degradation procedures. The N-terminal amino acid sequence of TIC807 is presented as SEQ ID NO:1. Queries of available public databases failed to identify a significant match to this sequence, suggesting the TIC807 protein may be novel. Two degenerate oligonucleotides primers, designated djc-pr12 (SEQ ID NO:2) and djc-pr113 (SEQ ID NO:3) were designed based upon the amino acid sequence, SEQ ID NO:1 to serve as hybridization probes for the isolation of a *B. thuringiensis* genes encoding the TIC807 protein and TIC807 homologs.

Example 3

Isolation and Characterization of TIC807 Isolated from *B. thuringiensis* Strain EG2934

This example illustrates the screening for phage clones containing DNA encoding the TIC807 protein. The cloning and sequencing of the DNA encoding the TIC807 protein is also described. The method described below can also be applied to recovery of DNA sequences encoding TIC807 homologs and related genes in plasmid, cosmid or phage libraries derived from other *B. thuringiensis* strains.

The oligonucleotide primers described in example 2, djc-pr12 and djc-pr13 (SEQ ID NO:2 and SEQ ID NO:3, respectively), were used as hybridization probes to probe a library constructed using size selected DNA isolated from *B. thuringiensis* strain EG2934. In the degenerate oligonucleotides of SEQ ID NO:2 (AAYGCDATHA AYTAYTGGGG DCCDAARAAY) and SEQ ID NO:3 (TGGGGDCCDA ARAAYAAYAA YGARATWCAR), Y residues represent a mixture of C or T residues, D residues represent a mixture of A, G, or T residues, H residues represent a mixture of A, C, or T residues, R residues represent a mixture of A or G residues, and W residues represent a mixture of A or T residues. Total DNA from *B. thuringiensis* strain EG2934 was prepared using a protocol that employs a CTAB extraction step (Current Protocols in Molecular Biology (1997) John Wiley and Sons, Inc.). This DNA failed to cut with the restriction enzyme Sau3AI, a 4-base cutter typically used to prepare genomic libraries. Surprisingly, an isoschizimer of Sau3AI that is sensitive to DNA methylation, MboI, digested the genomic DNA efficiently. The digested DNA was size fractionated on a 1% agarose 1×TBE gel. MboI fragments of 7-12 kb were extracted from gel slices using standard protocols and ligated into a BamHI-digested λ-Zap Express vector and packaged into phage particles using a GigaPack III Gold kit (Stratagene, La Jolla, Calif.). After phage amplification, transfections were plated and plaque lifts performed with Duralon UV nylon membranes (Stratagene, La Jolla, Calif.). The membranes were incubated at 50 degrees Celsius in a standard prehybridization/hybridization buffer containing 5×SSC, 0.1% N-lauroyl sarcosine, 0.02% SDS, 1% Blocking Reagent (Roche, Indianapolis, Ind., Cat. No. 1585762), 0.1 mg/mL poly-A, and 4 ug/mL poly-dA for several hours. The oligonucleotides were labelled on the 3' end with digoxigenin (DIG) using terminal transferase, DIG-11-dUTP (DIG oligonuceotide tailing kit; Roche, Indianapolis, Ind., Cat. No. 1 417 231) and protocols recommended by the manufacturer. A 1:1 mixture of the DIG-labeled oligos djc-pr12 and djc-pr13 was added and the membranes incubated overnight at 50 degrees Celsius. Filters were washed twice for 15 minutes at room temperature in 3×SSC, 0.1% SDS and twice for 15 minutes at 50 degrees Celsius in 1×SSC, 0.1% SDS. Hybridizing plaques were visualized by chemiluminescence using the Roche (Indianapolis, Ind.) Wash and Block buffer set and protocols (Roche, Indianapolis, Ind., Cat. No. 11585762001), anti-DIG-alkaline phosphatase Fab fragments (Roche, Indianapolis, Ind., Cat. No. 11093274910) and the substrate CSPD (Disodium 3-(4-methoxyspiro {1,2-dioxetane-3,2-(5-chloro) tricyclo [3.3.1.13.7]decan}-4-yl)phenyl phosphate) (Roche, Indianapolis, Ind.). Twelve recombinant clones were picked from the primary plates, diluted, plated, and re-probed with the DIG-labeled oligos. Only two rounds of plating/probing were required to obtain pure clones. All twelve phage clones were subjected to excision reactions yielding 12 individual phagemid clones. These were digested with SalI and NotI to release the cloned inserts. The digests were resolved on a 1% agarose 1×TBE gel and blotted to a Nytran® membrane for Southern analysis. The insert sizes were much smaller than expected, ranging in size from 2-5 kb. Nevertheless, the Southern analysis demonstrates the presence of hybridizing DNAs in 9 of 12 clones.

Thermal amplification reactions using combinations of the degenerate oligos, djc-pr12 and djc-pr13 with primers specific for vector sequences flanking the inserts were run to map the location of the TIC807 coding region on the phagemid clones. Based upon these results, it was determined that the entire gene was present on four different phagemid clones designated pIC17039 through pIC17042. The insert size and strain identification corresponding to each of these phagemid clones is shown in Table 2.

TABLE 2

Escherichia coli strains containing TIC807 phagemids and the associated insert size.

| Strain | Phagemid | Estimated Insert size (kilobases) |
|---|---|---|
| SIC8087 | pIC17039 | 2.3 |
| SIC8088 | pIC17040 | 3.5 |
| SIC8089 | pIC17041 | 5.5 |
| SIC8090 | pIC17042 | 1.5 |

The TIC807 gene insert on plasmid pIC17042 was sequenced. The deduced coding region (presented as SEQ ID NO:4) encodes a protein of 309 amino acids and is presented as SEQ ID NO:5. A BlastP (version 2.2.9) search of the non-redundant protein database revealed the closest match to the TIC807 protein sequence was to the *B. thuringiensis* crystal protein Cry15Aa1 (SEQ ID NO:41). A Needleman-Wunsch global alignment of the two proteins demonstrated a 25.5% sequence identity between the TIC807 protein sequence and the protein sequence of Cry15Aa1. The alignment of TIC807 (SEQ ID NO:5) and Cry15Aa (SEQ ID NO:41) is illustrated in FIG. 1. Although the TIC807 and Cry15Aa1 proteins are not highly conserved, localized regions of the proteins display complete sequence conservation over short stretches of contiguous amino acid sequences of up to seven residues in length.

*Escherichia coli* strain SIC8088 harboring vector pIC17040 was deposited on Mar. 16, 2007 with the Agricultural Research Culture Collection, Northern Regional Research Laboratory (NRRL) in Peoria, Ill. and given Accession No. NRRLB-50030.

Example 4

Expression of TIC807 in a Toxin-Free *B. thuringiensis* Host Strain

This example illustrates the cloning of the TIC807 coding region into a plasmid for expression in a toxin-free *B. thuringiensis* host strain. This example also illustrates a process by which a protein toxin such as TIC807 can be produced in purity for bioassay against insect pests.

The TIC807 plasmids pIC17040 and pIC17041 (Table 1) were digested with the restriction endonucleases NotI and XmaI and electrophoresed on a 1% agarose gel in 1×TBE. The resulting single DNA fragments were purified following agarose gel electrophoresis using a Qiagen (Valencia, Calif.) DNA purification kit following the manufacturer's protocol. Likewise, the *E. coli-B. thuringiensis* shuttle vector pEG854 (Baum et al. 1990) was digested with the restriction endonucleases NotI and XmaI and an approximate 4.3 kilobase DNA fragment containing the Bt plasmid replication origin ori43 and the chloramphenicol acetyltransferase (cat) gene was purified following agarose gel electrophoresis. Ligation of the TIC807 gene fragments with the ori43-cat gene fragment yielded plasmids capable of replicating in *B. thuringiensis*. The ligation products were used to transform the acrystalliferous (Cry-) *B. thuringiensis* host strain EG10650 to chloramphenicol resistance by electroporation, yielding the recombinant *B. thuringiensis* isolates SIC8091, SIC8092, SIC8093, and SIC8094 depicted in Table 3.

TABLE 3

*B. thuringiensis* strain containing plasmids for the expression of TIC807

| Strain | Plasmid | Estimated Insert size (kilobases) |
|---|---|---|
| SIC8091 | pIC17043 | 3.5 |
| SIC8092 | pIC17044 | 3.5 |
| SIC8093 | pIC17045 | 5.5 |
| SIC8094 | pIC17046 | 5.5 |

The recombinant strains were grown at 25 to 28 degrees Celsius in C2 medium for 3-4 days or until fully sporulated and lysed. Spores and crystals were collected by centrifugation (e.g., 4000×g for 30 minutes), resuspended in wash buffer (10 mM Tris-HCl, 0.1 mM EDTA, 0.005% Triton X-100, pH 6.8), and collected again by centrifugation. The spore-crystal pellets were resuspended in wash buffer at $\frac{1}{10}$ th the original culture volume. Crystal proteins present in these 10× C2 concentrates were analyzed by SDS polyacrylamide gel electrophoresis (SDS-PAGE). All four recombinant strains produced a crystal protein of the expected apparent molecular mass of approximately 35 kDa. Protein concentrations were determined by densitometry using bovine serum albumin (BSA) as a standard.

Example 5

TIC807 is Toxic to *Lygus hesperus* and *Lygus lineolaris*

This example illustrates the feeding assay used to identify the TIC807 protein molecule as being toxic to the western tarnished plant bug (WTPB), *Lygus hesperus* and the tarnished plant bug (TPB), *Lygus lineolaris*. The WTPB and TPB are phytophagous, piercing-sucking insects that attack numerous weeds and crops. The WTPB and TPB damage agricultural crops, including cotton, by direct feeding damage. Because the WTPB and TPB feed by piercing-sucking, the assay used to test protein toxins for this class of insects must allow for the insect's natural feeding behavior. The feeding assay employed was based on a 96 well format and a sachet system as described by Habibi et al., (Archives of Insect Biochem. and Phys. 50: 62-74 (2002)). The artificial diet was supplied by Bio-Serv® (Bio-Serv® Diet F9644B, Frenchtown, N.J.), the components of which are presented in Table 4.

TABLE 4

The Bio-Serv ® F9644B WTPB artificial diet.

| Diet Ingredients | Grams/Liter |
|---|---|
| Wheat Germ, Stabilized | 44.60 |
| Cholesterol | 0.50 |
| RNA | 5.00 |
| Vitamin mix, Vanderzant | 8.90 |
| Para-Aminobenzoic acid | 0.18 |
| Niacin | 0.18 |
| Vitamin E Acetate | 0.10 |
| Aureomycin | 0.10 |
| Streptomycin Sulfate | 0.135 |
| Carageenan (Irish Moss) | 3.00 |
| Lima Beans, ground | 45.00 |
| Casein Hydrolaysate | 17.90 |
| Salt Mix, Hesperus | 2.90 |
| Sucrose | 27.10 |
| Lecithin, Liquid, Soy | 0.50 |

TABLE 4-continued

The Bio-Serv® F9644B WTPB artificial diet.

| Diet Ingredients | Grams/Liter |
| --- | --- |
| Safflower Oil | 0.20 |
| Chicken eggs (4) | Not added |

Five hundred and eighteen milliliters of autoclaved, boiling water were combined with 156.3 grams of Bio-Serv® Diet F9644B in a surface sterilized blender. Four surface sterilized chicken eggs were broken and the contents were added to the blender containing the diet mix. The mixture was blended until smooth and adjusted to one liter of volume and allowed to cool. Toxin samples were prepared by mixing the TIC807 toxin protein preparation in the desired concentration with an equivalent volume of the blended diet.

A sheet of Parafilm® (Pechiney Plastic Packing, Chicago, Ill.) was placed over a 96-well format vacuum manifold (Analytical Research Systems, Gainesville, Fla.) with a vacuum of approximately −20 millimeters mercury, which is sufficient to cause extrusion of the Parafilm® into the wells. Forty microliters of test sample were added to the Parafilm® wells. A sheet of Mylar film (Clear Lam Packaging, Inc., Elk Grove Village, Ill.) was then placed over the Parafilm® and sealed gently with a tacking iron (Bienfang Sealector II, Hunt Corporation, Philadelphia, Pa.). The Parafilm® sachets were then placed over a flat-bottom 96-well plate containing the Lygus eggs suspended in agarose. Upon hatching, Lygus nymphs will feed by piercing the sachet that is presented above them. Without being limited by theory, it is believed that extraoral digestion in the sachet may lead to proteolysis and degradation prior to ingestion by the insect. To assure intact protein was being presented to the insect in its diet, the diet sachets were replaced every two days. This enhancement in theory allows for longer presentation of the intact toxin proteins in the insect diet over the course of the feeding assay. In addition, lower concentrations of putative toxin protein can be tested since greater amounts of protein will not be required to compensate for potential extraoral digestive effects. Insect diet sachets were replaced on days two and four. Stunting and mortality scores were determined on day 5 and compared to the untreated check (UTC).

Tables 5 through 8 illustrate the toxicity of TIC807 to western tarnished plant bug (WTPB), Lygus hesperus and the tarnished plant bug (TPB), Lygus lineolaris. The diet was less than optimal for the TPB, reducing the rate of growth of the nymphs in the UTC (untreated check) sample relative to the UTC for WTPB. However, significant mortality and stunting was demonstrated against TPB.

TABLE 5

TIC807 stunting scores for western tarnished plant bug (WTPB), Lygus hesperus

| Treatment | concentration (mg/ml) | N | Mean stunting | Standard Deviation | P > |t| |
| --- | --- | --- | --- | --- | --- |
| UTC | 0.00 | 12 | 0.00 | 0.00 | |
| TIC807 | 1.00 | 5 | 1.60 | 0.55 | <0.0001 |

TABLE 6

TIC807 per cent mortality scores for western tarnished plant bug (WTPB), Lygus hesperus

| Treatment | concentration (mg/ml) | N | Mean % mortality | Standard Deviation | P > |t| |
| --- | --- | --- | --- | --- | --- |
| UTC | 0.00 | 12 | 0.00 | 0.00 | |
| TIC807 | 1.00 | 5 | 56.79 | 15.89 | <0.0001 |

TABLE 7

TIC807 stunting scores for the tarnished plant bug (TPB), Lygus lineolaris

| Treatment | concentration (mg/ml) | N | Mean stunting | Standard Deviation | P > |t| |
| --- | --- | --- | --- | --- | --- |
| UTC | 0.00 | 6 | 0.00 | 0.00 | |
| TIC807 | 1.00 | 5 | 1.20 | 0.20 | <0.05 |

TABLE 8

TIC807 per cent mortality scores for the tarnished plant bug (TPB), Lygus lineolaris

| Treatment | concentration (mg/ml) | N | Mean % mortality | Standard Deviation | P > |t| |
| --- | --- | --- | --- | --- | --- |
| UTC | 0.00 | 6 | 0.00 | 0.00 | |
| TIC807 | 1.00 | 5 | 45.33 | 7.65 | <0.05 |

Example 6

Synthesis of a Gene Encoding a TIC807 Protein that is Designed for Expression in Plants A nucleotide sequence encoding a TIC807 protein is designed and synthesized. This non-native coding region designed for plant expression is provided here as SEQ ID NO:6. The coding sequence is characterized by a lower A+T content than the native TIC807 coding region that was derived from Bacillus thuringiensis, eliminating regions of the native TIC807 gene that are A+T rich and replacing those with sequences that have fewer A+T residues.

Example 7

Expression Cassettes for Expression of a TIC807 Protein in Transgenic Plant Cells or Transgenic Plants A variety of plant expression cassettes were constructed with the non-native TIC807 coding region (SEQ ID NO:6). Such expression cassettes are useful for transient expression in plant protoplasts or plant callus.

A first TIC807 plant expression cassette comprises an enhanced CaMV35S promoter that is operably linked to a coding region comprising a non-native TIC807 encoding sequence with an in-frame C-terminal fusion to a myc-protein epitope tag (SEQ ID NO:19). This coding region is operably linked to a 3' terminal nopaline synthase (NOS) polyadenylation site. The sequence of this non-targeted and tagged 5'-e35S-TIC807-myc-NOS-3' expression cassette is provided as (SEQ ID NO:20) and was cloned in pMON59221. The entire 5'-e35S-TIC807-myc-NOS-3' expression cassette is contained on a NotI restriction fragment in the pMON59221 shuttle vector.

A second TIC807 plant expression cassette comprises an enhanced CaMV35S promoter that is operably linked to a coding region comprising an N-terminal *Arabidopsis* shkG chloroplast peptide encoding sequence (i.e., CTP2) fused in frame to a non-native TIC807 encoding sequence with an in-frame C-terminal fusion to a myc-protein epitope tag (SEQ ID NO:21). This coding region is operably linked to a 3' terminal nopaline synthase (NOS) polyadenylation site. The sequence of this targeted and tagged e35S-CTP2-TIC807-myc-NOS expression cassette is provided as (SEQ ID NO:22) and was cloned in pMON59223. The entire 5'-e35S-CTP2-TIC807-myc-NOS-3' expression cassette is contained on a NotI restriction fragment in the pMON59223 shuttle vector.

A third TIC807 plant expression cassette comprises an enhanced CaMV35S promoter that is operably linked to a coding region comprising a non-native TIC807 encoding sequence (SEQ ID NO:6). This coding region is operably linked to a 3' terminal nopaline synthase (NOS) polyadenylation site. The sequence of this non-targeted TIC807 expression cassette is provided as (SEQ ID NO:40) and was cloned in pMON59224. The entire 5'-e35S-TIC807-NOS-3' expression cassette is contained on a NotI restriction fragment in the pMON59224 shuttle vector.

A fourth TIC807 plant expression cassette comprises an enhanced CaMV35S promoter that is operably linked to a coding region comprising an N-terminal *Arabidopsis* shkG chloroplast peptide encoding sequence (i.e., CTP2) fused in frame to a non-native TIC807 encoding sequence (SEQ ID NO:7). The peptide sequence of the CTP2-TIC807 fusion protein encoded by this construct is provided as SEQ ID NO:8. This coding region is operably linked to a 3' terminal nopaline synthase (NOS) polyadenylation site. The sequence of this targeted 5'-e35S-CTP2-TIC807-NOS-3' expression cassette is provided as (SEQ ID NO:23) and was cloned in pMON59222. The entire 5'-e35S-CTP2-TIC807-NOS-3' expression cassette is contained on a NotI restriction fragment in the pMON59222 shuttle vector.

A fifth plastid-targeted expression cassette comprises an enhanced CaMV35S promoter that is operably linked to a 5' untranslated leader sequence derived from the *Glycine max* Hsp17.9 gene which is operably linked to a coding region comprising an N-terminal *Arabidopsis* shkG chloroplast peptide encoding sequence (i.e., CTP2) fused in frame to a non-native TIC807 encoding sequence (SEQ ID NO:6). The peptide sequence of the CTP2-TIC807 fusion protein encoded by this construct is provided as SEQ ID NO:8. This coding region is operably linked to a 3' terminal nopaline synthase (NOS) polyadenylation site. The sequence of this targeted 5'-e35S-Hsp17.9-CTP2-TIC807-NOS-3' expression cassette is provided as (SEQ ID NO:42).

A sixth expression cassette comprises an enhanced CaMV35S promoter that is operably linked to a 5' untranslated leader sequence derived from the *Glycine max* Hsp17.9 gene which is operably linked to a coding region comprising a non-native TIC807 encoding sequence (SEQ ID NO:6). The peptide sequence of the TIC807 protein encoded by this construct is provided as SEQ ID NO:5. This coding region is operably linked to a 3' terminal nopaline synthase (NOS) polyadenylation site. The sequence of this 5'-e35S-Hsp17.9-TIC807-NOS-3' expression cassette is provided as (SEQ ID NO:43).

Example 8

Construction of *Agrobacterium*-Mediated Transformation Vectors Containing TIC807 Expression Cassettes and Transfer to *Agrobacterium*

To construct *Agrobacterium* mediated transformation vectors, TIC807 expression cassettes are cloned into suitable vectors between the *Agrobacterium* border sequences such that they would be transferred to the genome of a host plant cell by *Agrobacterium* hosts containing the constructed vectors along with a selectable marker gene. More specifically, the restriction fragment containing the entire 5'-e35S-Hsp17.9-CTP2-TIC807-NOS-3' expression cassette (SEQ ID NO:42) is cloned into an *Agrobacterium* plant transformation vector. Similarly, the restriction fragment containing the entire 5'-e35S-Hsp17.9-TIC807-NOS-3' expression cassette (SEQ ID NO:43) is cloned into an *Agrobacterium* plant transformation vector. The vectors containing the TIC807 expression cassettes (i.e., non-targeted cassette of SEQ ID NO:43 and targeted cassette of SEQ ID NO:42) are introduced into *Agrobacterium* by electroporation or by tri-parental mating.

Example 9

Transformation of Cotton with TIC807 *Agrobacterium* Transformation Vectors

Cotton can be transformed with the TIC807 *Agrobacterium* transformation vectors pMON105863 and pMON105864 or their equivalents using a procedure substantially similar to the procedure described in U.S. Pat. No. 5,159,135.

To initiate the transformation and regeneration process for cotton plants, it is necessary to first surface sterilize cotton seeds to prevent inadvertent contamination of the resulting culture. The seeds are then allowed to germinate on an appropriate germinating medium containing a fungicide.

Four to six days after germination the hypocotyl portion of the immature plant is removed and sectioned into small segments averaging approximately 0.5 centimeters apiece. The hypocotyl explants are allowed to stabilize and remain viable in a liquid or agar plant tissue culture medium.

Once the hypocotyl segments have stabilized, they can promptly be inoculated with a suspension culture of transformation competent non-oncogenic *Agrobacterium*. *Agrobacterium* strains such as LBA4404 can be used. The inoculation process is allowed to proceed for three to five days at room temperatures, i.e., 24.degree. C.

At the end of the inoculation time period, it is necessary first to rinse off the excess *Agrobacterium*. Then the remaining treated tissues can be transferred to a second agar medium, which also contains one or more antibiotics toxic to *Agrobacterium*, but not to hypocotyl tissues, at a concentration sufficient to kill any *Agrobacterium* remaining in the culture. Suitable antibiotics for use in such a medium include carbenicillin and cefotaxime. The tissues are then given a period of from one to ten days to recover from the transformation process and are then continued in culture.

The tissues are now cultivated on a tissue culture medium which, in addition to its normal components, contains a selection agent, the selection agent being one toxic to non-transformed cotton cells but not to transformed cotton cells which have incorporated genetic resistance to the selection agent and are expressing that resistance.) A suitable tissue culture medium is the MS medium to which is added the phytohormones 2,4 dichlorophenoxy-acetic acid (2-4,D), 6-furfurylaminopurine and a gelling agent. Suitable selection agents include both antibiotics and herbicides. Suitable antibiotic traits which may serve as dominant selectable markers include the aminoglycoside phosphotransferase-3'-II (APH-(3')-II) gene, also referred to as the neomycin phosphotransferase II gene (NPTII), which code for resistance to the antibiotic kanamycin, and the APH-(3')-IV gene which codes for resistance to Hygromycin B. Kanamycin, G418 and Hygromycin B are aminoglycosides that will stop the growth of non-transformed cotton cells, but these antibiotics are phosphorylated by the appropriate enzyme if it is expressed in the transformed cells. Another suitable selection agent is the herbicide glyphosate which can be used to select for transformed cotton cells containing glyphosate resistant EPSPS genes. When using pMON105863 and pMON105864, the transformed plant cells are selected for resistance to kanamycin or another antibiotic that is closely related to kanamycin and inactivated by the neomycin phosphotransferase II gene (NP-TII) encoded by these vectors. Antibiotic or herbicide dosed media allows only transformed cells to continue to grow and thrive. Thus the transformed cells, or calli, are allowed to grow on the selective medium. The surviving transformed tissues are transferred to a secondary medium to induce somatic embryogenesis. The surviving transformed tissue will thus continue to form into somatic embryos, which can then be regenerated through the regeneration technique of the present invention or through any other alternative plant regeneration protocols which use cotton somatic embryos as their starting point.

The selection process should continue for an extended time, i.e., 3-4 months, because of the slow growth of even transformed tissues on the antibiotic medium. Subcultures are made every 4-6 weeks to replenish nutrients and antibiotics. As the transformed cells are selected and amplified, individually derived cell lines are identifiable and can be removed and separately amplified.

The regeneration technique in accordance with the present invention begins with the tissues resulting from the transformation process. These tissues are putatively transformed calli which can generate somatic embryos when cultivated on appropriate embryo induction media. One technique for regenerating these somatic embryos to whole plants is disclosed here, but it is to be understood that other techniques are also possible, once transformed embryogenic tissues are produced.

The regeneration technique used by the applicants here thus begins with the tissues resulting from the transformation process. The cotton tissue calli, generated from the hypocotyl segments of the cotton plants, and putatively transformed, are placed onto somatic embryo induction media directly. At this point, the antibiotic selection agent should be removed from the culture medium, but otherwise the medium may remain constant. These calli, cultured on the somatic embryo induction medium, will form small embryoidal structures, which have been termed somatic embryos. It may take as long as two to three months for the somatic embryos to emerge and mature. Approximately 5 to as many as 20 somatic embryos will emerge from a single callus in an agar formulation of a somatic embryo induction medium. Many of the somatic embryos thus produced will be regenerable into whole plants in accordance with the technique described here.

When the developing somatic embryos are large enough, i.e., to a size of 4 mm or more in length, and if they appeared to have good embryonic development, i.e., usually having a cotyledon and a radicle, they may be transferred to large test tubes and hosted on fine vermiculite. The vermiculite is saturated with Stewart and Hsu (SH) medium (Planta 137:113 (1977)) plus the phytohormones indole acetic acid, 6-furfurylaminpurine and gibberellic acid. Small plantlets, having two to three leaves, eventually develop.

Once plantlet growth is established, i.e., the 2-3 leaf stage, the plants can now move into plant pots with vermiculite soil. They may be watered and fertilized as needed. They may also need to be hardened off, before greenhouse exposure. The plantlets may be repotted when they have 4-6 leaves after which they will continue to grow until mature. Samples from the plantlets can be assayed for expression of TIC807 to identify transgenic plants with insect inhibitory activity.

Example 11

In-Planta Testing of TIC807 in Callus Tissue

This example illustrates a non-limiting example of in planta expression of TIC807 for bioassay against *Lygus* and other insect pests that pierce and/or suck the fluids from the cells and tissues of plants.

Cotton cells are transformed with constructs containing the TIC807 protein encoding genes of interest. In this case, non-native A+T rich nucleic acid sequences encoding a TIC807 protein are expressed in cotton cells using the TIC807 expression cassettes in the TIC807 transformation vectors described in the preceding examples. These expression cassettes provide for either targeting of TIC807 to the chloroplast (i.e., with the 5'-e35S-Hsp17.9-CTP2-TIC807-NOS-3' or 5'-e35S-CTP2-TIC807-NOS-3' expression cassette) or non-targeted (cytoplasmic) expression of TIC807 (i.e., with the 5'-e35S-Hsp17.9-TIC807-NOS-3' or the 5'-e35S-TIC807-NOS-3' expression cassettes). The transformation vectors provide a selectable marker, in this case for selection of kanamycin resistance in transformed plant tissue. Either the pMON105863 vector or other equivalent TIC807 plant expression vectors that contain TIC807 plant expression cassettes and a selectable marker can be used. Callus tissue is allowed to develop in tissue culture after transformation and selection in a Petri dish. The *Lygus* nymphs are then placed into a Petri dish or microtiter plate well containing callus that is transformed with a TIC807 plant expression cassette. *Lygus* nymphs are also placed into a Petri dish or microtiter plate well containing control callus that is not transformed with a TIC807 plant expression cassette. The secured lid of the Petri dish or microtiter plate well prevents the escape of the *Lygus* nymphs. Any material that will prevent *Lygus* escape but allow gas exchange in the Petri dish, for example, Parafilm® can be used to secure the Petri dish lid or microtiter plate well. A percentage of *Lygus* nymphs will find the callus tissue and feed. Scores for mortality and stunting are then calculated taking into account the background death that will occur from those insects which fail to feed on the callus tissue to obtain an adjusted score. The adjusted scores for the *Lygus* nymphs presented with the TIC807 transformed tissue are compared with the adjusted scores for the *Lygus* nymphs presented with control tissue. Scores for mortality and/or stunting for the *Lygus* nymphs presented with the TIC807 transformed tissue are significantly increased relative to the scores for the *Lygus* nymphs presented with control tissue.

Example 12

In-Planta Testing of TIC807 in Leaf Tissue

Alfalfa, cotton, canola, soybean, or lettuce cells are transformed using the TIC807 expression cassettes in the TIC807 transformation vectors described in the preceding examples. These expression cassettes provide for either targeting of TIC807 to the chloroplast (i.e., with the 5'-e35S-CTP2-TIC807-myc-NOS-3' or 5'-e35S-CTP2-TIC807-NOS-3' expression cassettes) or non-targeted (cytoplasmic) expression of TIC807 (i.e., with the 5'-e35S-TIC807-myc-NOS-3' or 5'-e35S-TIC807-NOS-3' expression cassettes). The transformation vectors provide a selectable marker, in this case for selection of kanamycin resistance in transformed plant tissue. The transformed cells are selected for resistance to kanamycin and regenerated into transgenic plants. Insect pests such as *Lygus* nymphs are then allowed to feed when the plant has reached a sufficient level of maturity, such as when the leaves have grown to a size permitting the use of a physical barrier to prevent *Lygus* escape. The barrier to prevent escape of the *Lygus* nymphs can be any commercially available or home made device that permits contact of the *Lygus* nymphs with the leaf tissue and allows the insect to probe and feed from the vascular tissue of the leaf. Clip cages similar to those described by Mowry (1993) (J. Agric. Entomol. 10:181-184) would be sufficient to contain the *Lygus* nymphs for feeding. *Lygus* nymphs are thus presented with leaf tissue from either transgenic plants that express the TIC807 protein or with control leaf tissue that does not express TIC807 protein. The control leaf tissue is ideally provided by a transgenic plant that was selected and regenerated in parallel but does not contain a TIC-encoding transgene. However, leaf tissue from other plants of similar origin and age can also be used so long as the tissue does not contain significant amounts of TIC807 protein. Mortality and stunting scores are then determined with respect to the background death that will occur from those insects which fail to feed on the leaf tissue to obtain an adjusted score. The adjusted scores for the *Lygus* nymphs presented with the TIC807 transformed leaf tissue are compared with the adjusted scores for the *Lygus* nymphs presented with control leaf tissue. Scores for mortality and/or stunting for the *Lygus* nymphs presented with the TIC807 transformed leaf tissue are significantly increased relative to the scores for the *Lygus* nymphs presented with control leaf tissue.

Example 13

Insect Control Using TIC807 in Combination with Other Insect Control Agents

Having obtained transgenic cotton plants that express either cytoplasmic or targeted TIC807 protein, it is also desirable to obtain cotton plants that express other insect inhibitory proteins in combination with TIC807. This example illustrates several methods by which increased resistance to a specific insect pest or broader resistance to several classes of insect pests can be achieved to provide greater insect protection for a crop plant. All of the strategies described below can also be used to enhance an insect resistance management program.

I) Combination of TIC807 with Insect Inhibitory dsRNAi Molecules in Plants

Double stranded RNA mediated gene suppression of biological function within target insect pests can be combined with genes encoding a TIC807 protein. Insect genes that perform key biological functions that can be targeted by dsRNAi are described in U.S. Patent Application Publication No. US 2006/0021087.

Such dsRNAi molecules can be directed to inhibiting *Lygus*, which is the same target insect that is inhibited by TIC807. By simultaneously inhibiting *Lygus* with a dsRNAi molecule and TIC807, inhibition is achieved through two distinct modes of action. Inhibition by distinct modes of action is expected to result in improved insect resistance management. For control of *Lygus*, dsRNAi molecules are derived from any one of SEQ ID NO:4 through SEQ ID NO:39 that corresponds to genes expressed in *Lygus*. The use of SEQ ID NO:24 through SEQ ID NO:39 in the control of insects is disclosed in U.S. Patent Application Publication No. 20060021087. The dsRNAi molecules directed against any one of SEQ ID NO:24 through SEQ ID NO:39 are expressed in transgenic cotton plants with *Agrobacterium*-mediated transformation vectors designed for expression of ds RNAi molecules. Expression of dsRNAi molecules is achieved by recovery of transgenic plants comprising a promoter active in those plants that is operably linked to fragments of the *Lygus* sequences (i.e., SEQ ID NO:24 through SEQ ID NO:39) of at least 19-24 nucleotides in length and the reverse complements of those sequences.

Such dsRNAi molecules also can be directed to other piercing sucking insects such as aphids, hoppers, or whiteflies. For control of aphids, dsRNAi molecules derived from or homologous to sequences from *Toxoptera citricida* or *Acyrthosiphon pisum* from U.S. Patent Application Publication No. 2006/0021087 are expressed in transgenic plants with *Agrobacterium*-mediated transformation vectors designed for expression of ds RNAi molecules. For control of hoppers, dsRNAi molecules derived from or homologous to sequences from Homalodisca coagulate from Patent Application Publication No. U.S. 2006/0021087 are expressed in transgenic plants with *Agrobacterium*-mediated transformation vectors designed for expression of ds RNAi molecules. For control of whiteflies, suitable dsRNAi molecules can be expressed in transgenic plants with *Agrobacterium*-mediated transformation vectors designed for expression of ds RNAi molecules. Expression of dsRNAi molecules is achieved by recovery of transgenic plants comprising a promoter active in those plants that is operably linked to fragments of the respective aphid, hopper, or whitefly sequences of at least 19-24 nucleotides in length and the reverse complements of those sequences.

Such dsRNAi molecules also can be directed to coleopteran pests. In this case, expression of the dsRNAi molecule in conjunction with TIC807 provides for control of both a coleopteran pest and a dipteran pest in a transgenic plant. For control of the boll weevil, *Anthonomus grandis* Boheman, dsRNAi molecules derived from a V-ATPase A ortholog sequence described in U.S. Patent Application Publication No. 2006/0021087 are expressed in transgenic cotton plants with *Agrobacterium*-mediated transformation vectors designed for expression of ds RNAi molecules. Expression of dsRNAi molecules is achieved by recovery of transgenic cotton plants comprising a promoter active in those plants that is operably linked to fragments of the boll weevil V-ATPase A of at least 19-24 nucleotides in length and the reverse complements of those sequences.

Such dsRNAi molecules also can be directed to Lepidopteran pests. In this case, expression of the dsRNAi molecule in conjunction with TIC807 provides for control of both a Lepidopteran pest and a Dipteran pest in a transgenic plant. For control of the army worm, dsRNAi molecules derived from a midgut-expressed Army worm sequence (i.e., *Helicoverpa armigera* sequences from U.S. Patent Application No. 2006/0021087) are expressed in transgenic cotton plants with *Agrobacterium*-mediated transformation vectors designed for expression of ds RNAi molecules. Expression of dsRNAi molecules is achieved by recovery of transgenic cotton plants comprising a promoter active in those plants that is operably linked to fragments of the Armyworm sequence of at least 19-24 nucleotides in length and the reverse complements of those sequences.

I) Combination of TIC807 with Insect Inhibitory Proteins Other Than TIC807 in Plants For the control of piercing sucking insects such as aphids, hoppers, *Lygus*, or whiteflies, several toxin molecules can be combined with TIC807 expression in planta for greater control. Such molecules expressed inplanta along with TIC807 may include: i) ET29, ET37 or TIC809 and TIC810, TIC812, TIC127 or TIC128 (PCT US 2006/033867; U.S. Pat. No. 6,093,695); ii) AXMI-027, AXMI-036, and/or AXMI-038 (WO 06/107761); iii) AXMI-018, AXMI-020, and/or AXMI-021 (WO 06/083891); iv) AXMI-010 (WO 05/038032); v) AXMI-003 (WO 05/021585) vi) AXMI-008 (US 2004/0250311); vii) AXMI-006 (US 2004/0216186) viii) AXMI-007 (US 2004/0210965); ix) AXMI-009 (US 2004/0210964); x) AXMI-014 (US 2004/0197917); xi) AXMI-004 (US 2004/0197916); xii) AXMI-028 and/or AXMI-029 (WO 06/119457) and xiii) AXMI-007, AXMI-008, AXMI-0080rf2, AXMI-009, AXMI-014 and AXMI-004 (WO 04/074462). The combination of the toxin protein molecules TIC809 (presented as SEQ ID NO:10) and TIC810 (presented as SEQ ID NO:12) has been previously shown to be inhibitory to the Western Tarnished Plant Bug (WTPB), Lygus hesperus Knight in bioassay (PCT US 2006/033867). The fusion proteins of TIC809 and TIC810, TIC127 (presented as SEQ ID NO:14) and TIC128 (presented as SEQ ID NO:16) may also be active against Lygus. The polynucleotide encoding TIC127 is comprised of the nucleic acid molecule encoding TIC809 linked to the nucleic acid molecule encoding TIC810 by a polylinker nucleotide sequence (presented as SEQ ID NO:17) encoding the amino acid linker presented as SEQ ID NO:18. The polynucleotide encoding TIC128 is comprised of the nucleic acid molecule encoding TIC810 linked to the nucleic acid molecule encoding TIC809 by a polylinker nucleotide sequence (presented as SEQ ID NO:17) encoding the amino acid linker presented as SEQ ID NO:18. Expression of TIC807 in combination with TIC127 or TIC128 may provide enhanced control of Lygus. Dicot plants such as cotton could be transformed with plant expression constructs containing dicot-optimized nucleotide sequences encoding TIC807 (presented as SEQ ID NO:6) along with TIC809 (presented as SEQ ID NO:9) and TIC810 (presented as SEQ ID NO:11), or TIC127 (presented as SEQ ID NO:13), or TIC128 (presented as SEQ ID NO:15) to provide enhanced resistance to Lygus or broader specificity to species contained within the genus, Lygus. Optimal expression of the toxin molecules may require targeted expression such as to the chloroplast of the cells. This can be achieved by the addition of a transit peptide-encoding nucleic acid molecule, well known in the art to direct the translated protein to the chloroplast of the cell, to the 5' end of the nucleic acid molecule encoding the toxins.

DNA sequences encoding the TIC807 expression cassettes can be combined with either one or both of DNA sequences that encode insect inhibitory double stranded RNA and/or insect inhibitory protein molecules other than TIC807. These DNA molecules can be combined either through direct transformation or breeding, or a combination thereof, to produce elite or hybrid plant lines demonstrating enhanced resistance to Lygus.

The combination of an insecticidal protein or proteins with one or more double stranded RNA, all independently active against a Hemipteran pest such as Lygus, is preferred as it provides two different modes of action (resistance management), and results in unexpected synergistic effects that are not observed with either the insecticidal protein alone, the double stranded RNA alone, or combinations of two different insecticidal proteins, both active against a Hemipteran pests, or combinations of two different dsRNA's, both active against a Hemipteran pests. In addition, the spectrum of resistance of the crop plant could be broadened to contain resistance to additional classes of insect pests such as Coleopteran, Lepidopteran or Dipteran pests in addition to a Hemipteran pest such as Lygus using both the expression of insect toxin proteins and double stranded RNA molecules within the plant.

For control of Lepidopteran pests and Hemipteran pests in a transgenic plant, plants expressing both a TIC807 protein and one or more proteins active against Lepidopteran pests can be obtained. Methods of obtaining transgenic plants that are express Lepidopteran-active proteins such as Cry1A proteins (U.S. Pat. No. 5,880,275), Cry1B (U.S. patent application Ser. No. 10/525,318), Cry1C (U.S. Pat. No. 6,033,874), Cry1F, Cry1A/F chimeras (U.S. Pat. Nos. 7,070,982, 6,962,705, and 6,713,063), and a Cry2Ab protein (U.S. Pat. No. 7,064,249) are well characterized. Plants expressing both a TIC807 protein and a Lepidopteran active protein can be obtained by making crosses of individual transgenic plants that express TIC807 or the Lepidopteran protein(s). Alternatively, plant transformation vectors that provide for expression of both TIC807 or one or more Lepidopteran active protein(s) can be used to transform plants.

Example 14

Toxicity of Purified Crystal Spore Preps of TIC807 to Lygus hesperus

Toxicity of TIC807 to Lygus hesperus was also tested using a purified crystal spore prep. Parasporal crystals containing the TIC807 protein were partially purified by sucrose gradient centrifugation. A 10×-concentrated spore-crystal preparation of the TIC807 protein was treated with Benzonase™ (Novagen; 10 U/ml sample) to reduce sample viscosity. The treated sample was allowed to sit overnight at 4 C. Sucrose gradients in Ultraclear™ or Polyclear™ tubes suitable for a SW28 rotor were prepared: 10 mL steps of 79%, 70%, and 55% sucrose in 10 mM Tris-HCl, 0.1 mM EDTA, 0.005% Triton X-100 (pH 7). Approximately 6-7 mL sample were loaded per gradient (tubes filled to ¼ inch from the top). The gradients were run at 18K overnight (16-18 hr) in a SW28 rotor at 4 C. Crystals were pulled from either the 55-70% interface or the 70-79% interface. Crystals were diluted at least 5-fold in gradient buffer and pelleted by centrifugation (e.g. 8K for 20 min at 4° C.). The crystal pellets were resuspended in buffer and examined under a phase-contrast microscope to assess spore contamination. Purified crystals were subsequently treated with 50 mM CAPS-NaOH (pH 11) and incubated at 37 C until the suspension cleared. The solubilized protein was dialyzed against 25 mM sodium carbonate, 10 mM NaCl (pH 8.0), loaded onto a Q-Sepharose column equilibrated with the same buffer, and eluted using a linear 10 mM-500 mM NaCl gradient. The eluted protein was dialyzed against 25 mM sodium carbonate (pH 8.5). The protein was judged to be highly purified by SDS-PAGE analysis. This TIC807 protein preparation was observed to cause significant mortality and stunting (mass reduction) of Lygus hesperus nymphs in the feeding assay when compared to the untreated check and are presented in Tables 9 and Table 10 below.

TABLE 9

TIC807 stunting scores for western tarnished plant bug (WTPB), Lygus hesperus

| Treatment | concentration (mg/ml) | N | Mean stunting | Standard Deviation | P > \|t\| |
|---|---|---|---|---|---|
| UTC | 0 | 8 | 0 | 0 | |
| TIC807 | 0.05 | 5 | 2.0 | 0 | <0.0001 |

TABLE 10

| TIC807 per cent mortality scores for western tarnished plant bug (WTPB), *Lygus Hesperus* | | | | | |
|---|---|---|---|---|---|
| Treatment | Concentration (mg/ml) | N | Mean % mortality | Standard Deviation | P > \|t\| |
| UTC | 0 | 8 | 0 | 0 | |
| TIC807 | 0.05 | 5 | 39.0 | 16.7 | 0.0003 |

Similar results were obtained in feeding assays with *Lygus lineolaris.*

Example 15

Figure 5:
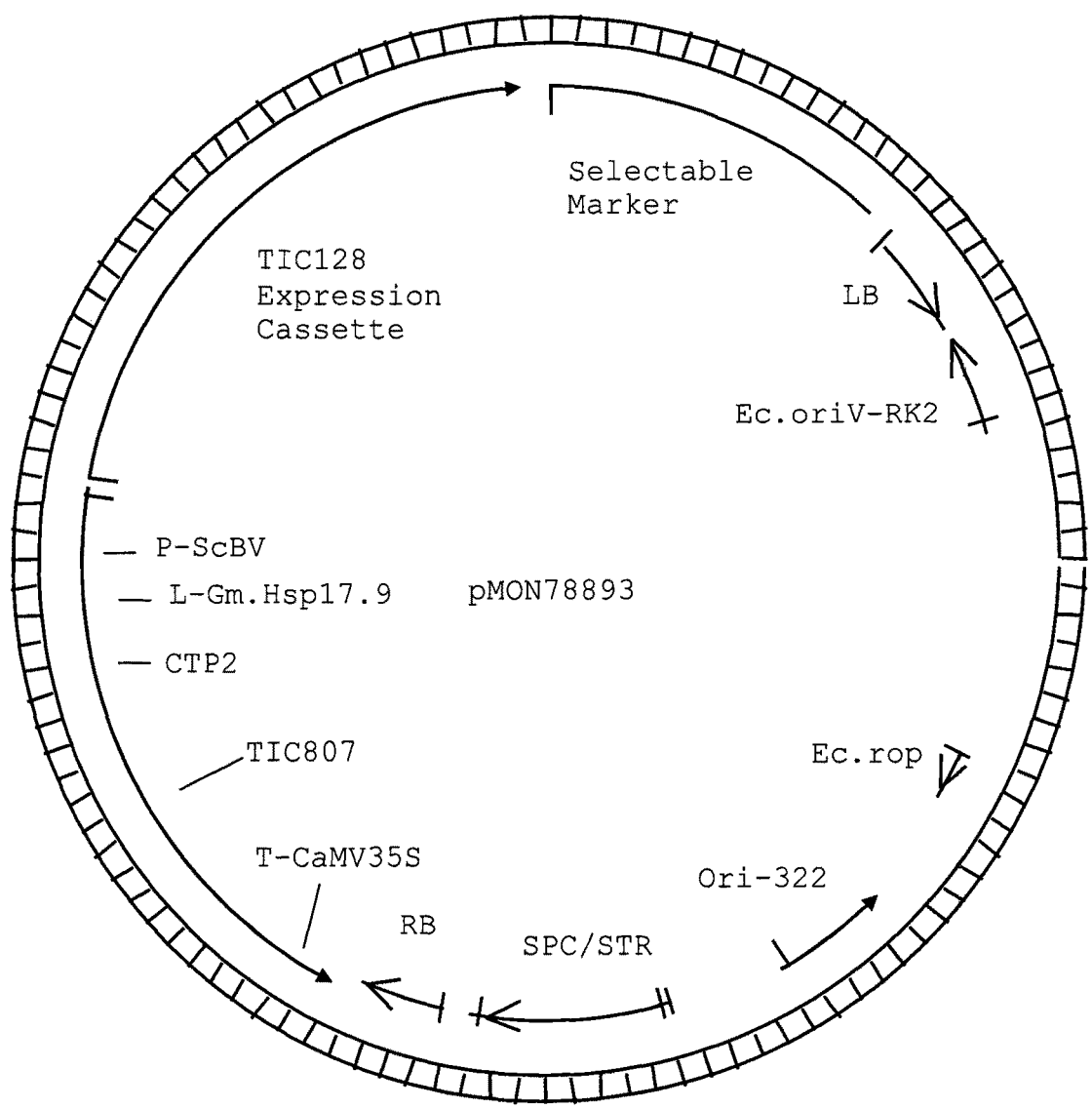
FIG. 5 illustrates the *Agrobacterium*-mediated plant transformation vector pMON78893 that contains a TIC807 plant expression cassette, a neomycin selection cassette, and a TIC128 expression cassette within the *Agrobacterium* border sequences.

Synthesis of Additional Genes Encoding a TIC807 Protein that are Designed for Expression in Plants Additional nucleotide sequences encoding a TIC807 protein were designed and synthesized. These non-native coding region designed for plant expression are provided here as SEQ ID NO: 44 through SEQ ID NO: 53. The coding sequences presented as SEQ ID NO: 44 through SEQ ID NO: 53 are characterized by a lower A+T content than the native TIC807 coding region that was derived from *Bacillus thuringiensis*, eliminating regions of the native TIC807 gene that are A+T rich and replacing those with sequences that have fewer A+T residues. SEQ ID NO: 44 is the native TIC807 coding region with the initiating Methionine start codon changed from the bacterial start codon of "TTG" to the plant start codon, "ATG'.

Example 16

Additional Expression Cassettes for Expression of a TIC807 Protein in Transgenic Plant Cells or Transgenic Plants A seventh plastid-targeted expression cassette comprises an enhanced CaMV35S promoter that is operably linked to a 5' untranslated leader sequence derived from the *Glycine max* Hsp17.9 gene which is operably linked to a coding region comprising an N-terminal *Arabidopsis* shkG chloroplast peptide encoding sequence (i.e. CTP2) fused in frame to a non-native TIC807 encoding sequence (SEQ ID NO:6). The peptide sequence of the CTP2-TIC807 fusion protein encoded by this construct is provided as SEQ ID NO:8. This coding region is operably linked to a 3' terminal CaMV35S polyadenylation site (T-35S). The sequence of this targeted 5'-e35S-Hsp17.9-CTP2-TIC807-T-35S-3' expression cassette is provided as SEQ ID NO:54.

An eighth expression cassette comprises an enhanced CaMV35S promoter that is operably linked to a 5' untranslated leader sequence derived from the *Glycine max* Hsp17.9 gene which is operably linked to a coding region comprising a non-native TIC807 encoding sequence (SEQ ID NO:6). The peptide sequence of the TIC807 protein encoded by this construct is provided as SEQ ID NO:5. This coding region is operably linked to a 3' terminal CaMV35S polyadenylation site. The sequence of this 5'-e35S-Hsp17.9-TIC807-T-35S-3' expression cassette is provided as SEQ ID NO:55.

A ninth plastid-targeted expression cassette comprises a Sugarcane Badnavirus (ScBV) promoter (U.S. Pat. No. 5,994,123) that is operably linked to a 5' untranslated leader sequence derived from the *Glycine max* Hsp17.9 gene which is operably linked to a coding region comprising an N-terminal *Arabidopsis* shkG chloroplast peptide encoding sequence (i.e. CTP2) fused in frame to a non-native TIC807 encoding sequence (SEQ ID NO:6). The peptide sequence of the CTP2-TIC807 fusion protein encoded by this construct is provided as SEQ ID NO:8. This coding region is operably linked to a 3' terminal CaMV35S polyadenylation site. The sequence of this targeted 5'-P-ScBV-Hsp 17.9-CTP2-TIC807-T-35S-3' expression cassette is provided as SEQ ID NO:56.

A tenth expression cassette comprises a Sugarcane Badnavirus promoter (ScBV) that is operably linked to a 5' untranslated leader sequence derived from the *Glycine max* Hsp17.9 gene which is operably linked to a coding region comprising a non-native TIC807 encoding sequence (SEQ ID NO:6). The peptide sequence of the TIC807 protein encoded by this construct is provided as SEQ ID NO:5. This coding region is operably linked to a 3' terminal CaMV35S polyadenylation site. The sequence of this 5'-P-ScBV-Hsp17.9-TIC807-T-35S-3' expression cassette is provided as SEQ ID NO:57.

Example 17

Construction of Additional *Agrobacterium*-Mediated Transformation Vectors Containing TIC807 Expression Cassettes and Transfer to *Agrobacterium*

To construct *Agrobacterium* mediated transformation vectors, TIC807 expression cassettes are cloned into suitable vectors between the *Agrobacterium* border sequences such that they would be transferred to the genome of a host plant cell by *Agrobacterium* hosts containing the constructed vectors along with a selectable marker gene. More specifically, the restriction fragment containing the entire 5'-e35S-Hsp17.9-CTP2-TIC807-T-35S-3' expression cassette (SEQ ID NO:54) is cloned into an *Agrobacterium* plant transformation vector to obtain pMON105863 (FIG. 2). Similarly, the restriction fragment containing the entire 5'-e35S-Hsp17.9-TIC807-T-35S-3' expression cassette (SEQ ID NO:55) is cloned into an *Agrobacterium* plant transformation vector to obtain pMON105864 (FIG. 3). For expression using a different promoter, the restriction fragment containing the entire 5'-P-ScBV-Hsp17.9-CTP2-TIC807-T-35S-3' expression cassette (SEQ ID NO:56) is cloned into an *Agrobacterium* plant transformation vector to obtain pMON78892 (FIG. 4). Similarly, the restriction fragment containing the entire 5'-P-ScBV-Hsp17.9-TIC807-T-35S-3' expression cassette (SEQ ID NO:57) is cloned into an *Agrobacterium* plant expression vector to obtain pMON78893 (FIG. 5). The vectors containing the TIC807 expression cassettes (i.e. non-targeted cassette of SEQ ID NO:55 and SEQ ID NO:57 and targeted cassette of SEQ ID NO:54 and SEQ ID NO:56) are introduced into *Agrobacterium* by electroporation or by tri-parental mating.

The binary plant transformation vectors contain a selectable marker (indicated as "Selectable Marker" in FIGS. 2 through 5) for selection of transformed plant cells using the antibiotic Kanamycin. Antibiotic selection using Spectinomycin is used for bacterial selection. This is indicated as "SPC/STR" in FIGS. 2 through 5 which is comprised of a promoter for Tn7 adenyltransferase, the coding region for a gene encoding 3" (9) —O-aminoglycoside adenyltransferase (AAD) derived from *Staphylococcus aureus* and the transcription terminator region from Tn7 adenyltransferase conferring spectinomycin and streptomycin resistance. Two origins for bacterial replication are included in each plasmid, an origin of replication for *Agrobacterium tumefaciens* replication (indicated as "Ec.oriV-RK2" in FIGS. 2 through 5) and an origin for replication in *Escherichia coli* (indicated as "Ori-322" in FIGS. 2 through 5). An *Escherichia coli* coding region encoding a repressor primer used in conjunction with the *E. coli* replication origin is indicated as "Ec.rop" in FIGS. 2 through 5. The left and right borders used for stable integration of the T-DNA into the plant genome are indicated as "LB" and "RB", respectively in FIGS. 2 through 5. FIG. 5 also shows an additional expression cassette used in which the TIC128 toxin protein (PCT US 2006/033867) is expressed and is labeled, "TIC128 Expression Cassette" in FIG. 5.

Example 18

Additional In-Planta Testing of TIC807 in Callus Tissue

This example illustrates additional non-limiting examples of in planta expression of TIC807 for bioassay against *Lygus* and other insect pests that pierce and/or suck the fluids from the cells and tissues of plants.

Alfalfa, cotton, canola, soybean, or corn cells are transformed using the TIC807 expression cassettes in the TIC807 transformation vectors described in the preceding examples. These expression cassettes provide for either targeting of TIC807 to the chloroplast (i.e., with the 5'-e35S-Hsp17.9-CTP2-TIC807-T-35S-3' or 5'-P-ScBV-Hsp17.9-CTP2-TIC807-T-35S-3' expression cassette) or non-targeted (cytoplasmic) expression of TIC807 (i.e., with the 5'-e35S-Hsp17.9-TIC807-T-35S-3' or the 5'-P-ScBV-Hsp17.9-TIC807-T-35S-3' expression cassettes). The transformation vectors provide a selectable marker, in this case for selection for kanamycin resistance in transformed plant tissue. The transformed cells are selected for resistance to kanamycin and regenerated into transgenic plants. Insect pests such as *Lygus* nymphs are then allowed to feed when the plant has reached a sufficient level of maturity, such as when the leaves have grown to a size permitting the use of a physical barrier to prevent *Lygus* escape. The barrier to prevent escape of the *Lygus* nymphs can be any commercially available or home made device that permits contact of the *Lygus* nymphs with the leaf tissue and allows the insect to probe and feed from the vascular tissue of the leaf. Clip cages similar to those described by Mowry (1993) (J. Agric. Entomol. 10: 181-184) would be sufficient to contain the *Lygus* nymphs for feeding. *Lygus* nymphs are thus presented with leaf tissue from either transgenic plants that express the TIC807 protein or with control leaf tissue that does not express TIC807 protein. The control leaf tissue is ideally provided by a transgenic plant that was selected and regenerated in parallel but does not contain a TIC-encoding transgene. However, leaf tissue from other plants of similar origin and age can also be used so long as the tissue does not contain significant amounts of TIC807 protein. Mortality and stunting scores are then determined with respect to the background death that will occur from those insects which fail to feed on the leaf tissue to obtain an adjusted score. The adjusted scores for the *Lygus* nymphs presented with the TIC807 transformed leaf tissue are compared with the adjusted scores for the *Lygus* nymphs presented with control leaf tissue. Scores for mortality and/or stunting for the *Lygus* nymphs presented with the TIC807 transformed leaf tissue are significantly increased relative to the scores for the *Lygus* nymphs presented with control leaf tissue.

Example 19

In-Planta Testing of TIC807 in Lettuce Leaf Tissue

Lettuce cells are transformed using the TIC807 expression cassettes in the TIC807 transformation vectors described in the preceding examples. These expression cassettes provide for either targeting of TIC807 to the chloroplast (i.e. with the 5'-e35S-Hsp17.9-CTP2-TIC807-T-35S-3' or 5'-P-ScBV-Hsp17.9-CTP2-TIC807-T-35S-3' expression cassettes) or non-targeted (cytoplasmic) expression of TIC807 (i.e. with the 5'-e35S-Hsp17.9-TIC807-T-35S-3' or the 5'-P-ScBV-Hsp17.9-TIC807-T-35S-3' expression cassettes). The transformation vectors provide a selectable marker, in this case for selection of kanamycin resistance in transformed plant tissue. The transformed cells are selected for resistance to kanamycin and regenerated into transgenic plants.

Lettuce seeds are surface sterilized for 20 minutes in 1.2% sodium hypochlorite solution followed by 3 washes in sterilized deionized water. The seeds are allowed to dry overnight in a Petri dish in a laminar flow hood. The seeds are then plated on 100 ml 0.5× Hoagland's salts (see Table 11 below) in phytatrays (Sigma, St. Louis, Mo., Catalog no: P1552) at a density of 60 seeds/tray. The seeds are grown under the light at 22 to 23 degrees Celsius for 4 to 5 days with a 16 hour photoperiod. *Agrobacterium* transformed with the plant transformation vector of interest are prepared by inoculating 10 mls of liquid Mannitol-Glutamate/Luria medium with 100 microliters of bacterial suspension. The medium is comprised of the following ingredients:

| | |
|---|---|
| LB broth, Miller (Difco #044-017-3) | 12.5 g |
| Mannitol | 5.0 g |
| Monosodium glutamate(glutamic acid) | 1.16 g |
| KH2PO4 | 0.25 g |
| MgSO47H2O | 0.10 g |
| Biotin | 0.001 g |
| Total volume | 1000 ml |
| pH to 7.00 and autoclave | |

The liquid culture is incubated on a gyratory shaker at 28 degrees Celsius for 24 hours. Five milliliters of the first overnight cultures are diluted with 15 milliliters of Tryptone Yeast Extract media supplemented with 40 mg/L Acetosyringone (5 grams of Tryptone, 3 grams of Yeast Extract and 20 ml of 2 mg/mL Acetosyringone in total volume of 1000 ml, pH 5.5 and autoclaved). This is then allowed to incubate on a gyratory shaker at 28 degrees Celsius for 24 hours in the dark with 50 mg/L kanamycin and 100 mg/L spectinomycin. One ml of overnight culture is added to 19 milliliters of Tryptone Yeast Extract media and the 600 nm wavelength optical density of the culture is adjusted to 0.08 to 0.09.

Lettuce seedling cotyledons are cut at both the base and the tip and soaked in the diluted *Agrobacterium* medium for 15 minutes. The cotyledons are then plated on MSO-C medium without blotting and kept at 22 to 23 degrees Celsius with a 16 hour photoperiod. Plates are sealed with micropore tape. After 48 hours, cotyledons are transferred to MSO-I medium in 100 mm×25 mm Petri dishes. Explants are subsequently subcultured at 7 and 14 days to MSO-I medium. As shoots develop they are excised and transferred to MSO-SE medium. Shoots are transferred after elongation to phytatrays containing 100 ml of MSO-SE medium. After 6 to 8 weeks, developing shoots are transferred to Magenta boxes containing 100 ml of MSO-R medium. In 7 to 14 days of incubation at 23 degrees Celsius, roots will begin to develop. The shoots are then transferred to 3 inch pots containing soil and allowed to grow. The composition of the MSO mediums is shown in table 11.

TABLE 11

MSO medium components.

| Ingredients | 0.5 X Hoagland's salt | MSO-C | MSO-I | MSO-SE | MSO-R |
|---|---|---|---|---|---|
| MSO salts (minimal salts) | | 34.6 g | 34.6 g | 34.6 g | 34.6 g |
| Hoagland's salt | 0.8 g | | | | |
| Naphthaleneacetic acid (1 mg/ml) | | 0.1 ml | 0.1 ml | 0.05 ml | |
| Benzyl adenine (1 mg/ml) | | 0.1 ml | 0.1 ml | 0.01 ml | |
| Acetosyringone (2 mg/ml) | | 20 ml | | | |
| Kanamycin (50 mg/ml) | | | 2 ml | 2 ml | 2 ml |
| Carbenicillin (250 mg/ml) | | | 2 ml | 2 ml | 2 ml |
| Tissue culture grade agar | 7.5 g | 7.5 g | 7.5 g | 8 g | 8 g |
| Total volume | 1000 ml | 1000 ml | 1000 ml | 1000 ml | 1000 ml |
| pH | | 5.7 | 5.7 | 5.7 | 5.7 |

The transgenic plants are self-fertilized and allowed to set seed or are used directly for testing. The leaves of the transformed lettuce plants are used in a culture system to test against *Lygus*. Ten milliliters of sterile plant growth media (Murashige & Skoog, Gamborg B5 vitamins, 3% sucrose and 1.5% agar) is added while in liquid state to sterile 50 milliliter polypropylene conical tubes. The media is allowed to cool and set under sterile conditions. Once set, a sterile circular foam divider, approximately the diameter of the tube containing a small hole in the middle is placed over the plant growth media. Young lettuce leaves are excised with a sterile razor blade and rinsed in sterile deionized water, leaving a portion of the petiole attached to the leaf. The petiole of the excised lettuce leaf is inserted through the hole and allowed to make contact with the media. Ten newly hatched (<12 hours post-hatch) *Lygus* nymphs are added to the tube and a foam stopper is used to close the tube to allow gas exchange. The tube is kept in an incubator set to 25 degrees Celsius with a 14:10 day:night photoperiod. Mortality and stunting scores are then determined with respect to the background death that will occur from those insects which fail to feed on the leaf tissue to obtain an adjusted score. The adjusted scores for the *Lygus* nymphs presented with the TIC807 transformed leaf tissue are compared with the adjusted scores for the *Lygus* nymphs presented with control leaf tissue. Scores for mortality and/or stunting for the *Lygus* nymphs presented with the TIC807 transformed leaf tissue are significantly increased relative to the scores for the *Lygus* nymphs presented with control leaf tissue.

Example 20

Expression of TIC807 in Transgenic Lettuce and Demonstration of in Planta Toxicity This example demonstrates *Lygus hesperus* toxicity of the TIC807 protein when expressed in Lettuce plants. Lettuce plants were transformed with the plant transformation vector, pMON105863 which contains the TIC807 expression cassette, 5'-e35S-Hsp17.9-CTP2-TIC807-T-35S-3' (SEQ ID NO:54) by the method described in Example 18. A control line of lettuce was transformed using a vector control in which only the selection cassette for transformation was contained. F1 seed was produced from the transformed plants. Plants were grown from F1 seed and sampled for expression of the TIC807 protein. Protein expression levels were determined for the F1 progeny using standard ELISA methods and TIC807 polyclonal antibody. Plants were selected for *Lygus hesperus* testing based upon TIC807 protein expression levels. Leaves were sampled from selected F1 progeny and tested for *Lygus hesperus* toxicity using the assay method described in Example 18. Data from selected transgenic lettuce lines are presented in Table 12. Line events A028 and A055 performed significantly better than the control (i.e. the untransformed lettuce line SVR3606). Overall analysis of the lines expressing the TIC807 protein demonstrated significant mortality relative to the control transformed plants.

TABLE 12

Mean ± standard error of percentage *Lygus hesperus* mortality on TIC807 transformed lettuce leaves 15 infested teneral nymphs (n = 16) six days after infestation.

| Event | TIC807 Concentration (ppm) | Percentage Mortality |
|---|---|---|
| A028 | 43.22 | 67.71 ± 5.55 P ≥ 0.05 |
| A055 | 41.62 | 62.08 ± 5.83 P ≥ 0.05 |
| A035 | 30.77 | 51.04 ± 2.73 |
| A002 | 33.02 | 50.00 ± 5.51 |
| A059 | 42.90 | 48.96 ± 2.83 |
| Control | 0.00 | 28.33 ± 2.15 |

Example 21

TIC807 Ts toxic to Colorado Potato Beetle

This example illustrates the toxicity of the insect toxin molecules TIC807 to the coleopteran, Colorado potato beetle (CPB), *Leptinotarsa decemlineata*. Bioassays with CPB were conducted using an artificial diet consisting of 13.2 g/L agar (Serva 11393), 140.3 g/L Bio-Serve pre-mix (Bio-Serve, Frenchtown, N.J. Catalog #F9380B), 5 ml/L Potassium hydroxide (18.3% w/w) and 1.25 ml/L formalin (37%). The diet was dispensed in 200 microliter aliquots into wells of a 96-well plate and dried briefly prior to sample application. Twenty microliters of test sample were applied per well, with sterile water serving as the untreated check (UTC). Plates were allowed to dry before adding insect larvae. One neonate CPB larva was added per well with a fine paintbrush. Plates were sealed with mylar and ventilated using an insect pin. Forty larvae were tested per treatment. The bioassay plates were incubated at 27 degrees Celsius with 60% relative humidity in complete darkness for 10 to 12 days. The plates were scored for larval mortality. Data were analyzed using JMP® 4 statistical software (SAS Institute, Cary, N.C.). TIC807 demonstrated mortality when fed to CPB. The mean percent mortality scores for TIC807 is presented in Table 13.

It is thus contemplated that TIC807 proteins of the invention can be used to control Coleopteran insects. Coleopteran insects controlled by TIC807 proteins of the invention include, but are not limited to, Colorado potato beetle, wire worm and boll weevil.

TABLE 13

TIC807 percent mortality scores for the Colorado potato beetle (CPB), *Leptinotarsa decemlineata*.

| Treatment | concentration (mg/ml) | N | Mean % mortality | Standard Deviation | P > \|t\| |
|---|---|---|---|---|---|
| UTC | 0 | 3 | 13.10 | 1.03 | |
| TIC807 | 0.5 | 3 | 68.45 | 23.03 | 0.0142 |

Example 22

Transformation of Cotton with TIC807 and Toxin Testing Using Whole Cotton Plants Cotton cells are transformed with constructs containing a TIC807 protein encoding gene of interest. In this case, codon redesigned nucleic acid sequences encoding for TIC807 protein are expressed in cotton cells using the TIC807 expression cassettes in the TIC807 transformation vectors described in the preceding examples. These expression cassettes provide for either targeting of TIC807 protein to the chloroplast (i.e. with the expression cassettes, 5'-e35S-Hsp17.9-CTP2-TIC807-T-35S-3' found in pMON105863 or 5'-P-ScBV-Hsp17.9-CTP2-TIC807-T-35S-3' found in pMON78892) or non-targeted (cytoplasmic) expression of TIC807 protein (i.e. with the expression cassettes, 5'-e35S-Hsp17.9-TIC807-T-35S-3' found in pMON105864 or the 5'-P-ScBV-Hsp17.9-TIC807-T-35S-3' found in pMON78893). The transformation vectors provide a selectable marker, in this case for selection of kanamycin resistance in transformed plant tissue. Either the pMON105863 vector (FIG. 2), the pMON105864 vector (FIG. 3) or the pMON78892 vector (FIG. 4) or the pMON78893 vector (FIG. 5) or other equivalent TIC807 plant expression vectors that contain TIC807 plant expression cassettes and a selectable marker can be used.

Bioassay on plants expressing the TIC807 toxin molecule can be performed using an enclosed cotton branch assay. Cotton plants are grown to an early bloom stage where several fruiting branches containing squares (i.e. immature cotton flowers) are available. Sleeves are prepared using breathable plastic sheets (Vilutis and Co. Inc., Frankfort, Ill.). Sleeves are made using a standard photography or arts and craft tacking iron to create a seam producing a bag with an approximate dimension of 5 inches×5 inches×12 inches long. Terminal branches including at least one pre-bloom square and unfolded terminal leaf are inserted into the open end of the sleeve. Alternatively, bags can be set up to enclose bolls or other tissues if desired. The bag is closed around the branch using a twist tie. Leaves and squares below the desired enclosed tissue can be removed to facilitate secure closer with the twist tie. The other end of the sleeve is left open to allow insect infestation. *Lygus* nymphs are collected with an aspirator and 4 nymphs are put into a 2 dram shell vial. Initial mass of the nymphs is recorded for each vial containing the nymphs. The tube is tapped gently to assure the nymphs are at the bottom of the tube and the cap of the tube is removed. The tube is placed inside the sleeve exposing the nymphs to the cotton plant tissue. The open end of the sleeve is then closed using a twist tie. The insects are allowed to remain in the sleeves and feed upon the enclosed cotton plant material for a specified number of days, After the specified time, the cotton branches are removed. The sleeves are carefully opened to count the surviving nymphs. All nymphs are collected and weighed. Mortality and stunting scores are then determined with respect to non-transformed control plants. The adjusted scores for the *Lygus* nymphs presented with the TIC807 transformed cotton tissue are compared with the adjusted scores for the *Lygus* nymphs presented with control cotton tissue that lacks the TIC807 protein. Scores for mortality and/or stunting for the *Lygus* nymphs presented with the TIC807 transformed cotton tissue are significantly increased relative to the scores for the *Lygus* nymphs presented with control cotton tissue.

Example 23

Combining TIC807 Toxin with Nectariless Cotton

This example illustrates using the nectariless phenotype of cotton in combination with TIC807 protein expression to provide greater control of an insect pest. Lack of nectaries has been identified as arising from homozygosity for recessive mutations at two duplicate loci in *Gossypium tomentosum* (Meyer and Meyer, 1961, Crop Science, 1: 167-169). Crosses with *Gossypium hirsutum* with *Gossypium tomentosum* demonstrated a significant reduction in populations of cabbage loopers and cotton leafworms in caged experiments relative to ordinary varieties of cotton in which floral nectarines are present (Lukefahr and Rhyne, 1960, Econ. Entomol. 53: 242-244). This is presumably the direct result of nectariless cotton lines being less palatable to the insect pest as well as the lack of sustenance provided by the nectars. Multiple mechanisms of resistance may be particularly crucial in Gossypieae species because extrafloral nectaries can directly attract some herbivore species. Extrafloral nectaries in cultivated cotton can enhance the abundance of or damage by several crop pests including lepidopterans and plant bugs (Trelease, 1879, Nectar; what it is, and some of its uses. In J. H. Comstock [ed.], Report upon cotton insects, 319-343. U.S. Department of Agriculture Publication, U.S. Government Publication Office, Washington, D.C., USA. Lukefahr and Rhyne, 1960; Lukefahr et al., 1960, Journal of Econ Entom 53: 516-518; Benschoter and Leal, 1974, Journal of Econ Entom 67: 217-218; Schuster et al., 1976, Journal of Econ Entom 69: 400-402; Wilson and Wilson, 1976, Journal of Econ Entom 69: 623-624; Henneberry et al., 1977, Journal of Econ Entom 70: 797-799; Adjei-Maafo et al., 1983, Environ Entom 12: 353-358; Beach et al., 1985, Journal of Entomological Science 20: 233-236; Smith, 1992, Advances in Agronomy 48: 251-296; Summy and King, 1992, Crop Protection 11: 307-319), mainly because adults of these taxa consume extrafloral nectar.

Lines produced by crosses of *G. hirsutum* with *G. tomentosum* are selected for the presence of the nectariless phenotype and favorable agronomic traits. In other embodiments, lines obtained from the commercial germplasm Stoneville 825 can be used as a source of germplasm comprising the nectariless phenotype. In one embodiment of the method, the selected nectariless lines are then transformed with the an expression cassette encoding either a TIC807 protein, the TIC809/TIC810 proteins, the TIC128 protein or combinations thereof, or any other toxin molecule directed to a pest of cotton in which the presence of nectaries act as an attractant to the insect pest. In another embodiment of the method, transgene inserts comprising an expression cassette encoding either a TIC807 protein, the TIC809/TIC810 proteins, the TIC128 protein or combinations thereof, or any other toxin molecule directed to a pest of cotton in which the presence of nectaries act as an attractant to the insect pest are obtained in any suitable cotton germplasm and then introgressed into lines produced by crosses of G. hirsutum with G. tomentosum that have been selected for the presence of the nectariless phenotype and favorable agronomic traits. Through breeding methods known to one of ordinary skill in the art, the transformant lines expressing the nectariless phenotypes are selected and maintained in subsequent generations to contain both the nectariless phenotype and the insect toxin molecule.

Example 24

Comparison of the TIC807 and Cry51Aa Proteins

To identify conserved and non-conserved regions of the TIC807 (SEQ ID NO:5) and Cry51 Aa (SEQ ID NO: 59) proteins, an alignment of the two proteins was created using ClustalW. The Cry51Aa protein was isolated from Bt strain F14-1, has a reported identity of 22% to cry15Aa, and is reported to have activity against Bombyx mori, a lepidopteran insect (Huang et al., J. Invertebr. Pathol. 95 (3), 175-180, 2007). A sequence for the cry51Aa1 gene (SEQ ID NO: 58) and the encoded Cry51Aa1 protein (SEQ ID NO: 59) was reported as the NCBI GenBank Accession number DQ836184. The ClustalW comparison of TIC807 (SEQ ID NO:5) and Cry51Aa1 demonstrate that the two proteins have an overall sequence identity of about 97.4% over a length of 301 amino acids (see FIG. 6 and Table 14). The GenBank accession number DQ836184 reports a deduced N-terminus for Cry51Aa1 that corresponds to use of a putative ATG start codon that would result in a 309 amino acid primary translation product. In contrast, the TIC807 protein has a distinct amino terminus based on an N-terminal peptide sequence of isolated TIC807 protein that was determined by Edman degradation (see Example 2 and SEQ ID NO:1). A TTG initiator methionine codon of SEQ ID NO:4 is apparently used to generate the TIC807 protein of SEQ ID NO:5. Consequently, the reported Cry51Aa1 protein comprises an additional three amino acids at its' N-terminus that do not occur in TIC807 (SEQ ID NO:5). In Cry51Aa1, the amino acid residue corresponding to phenylalanine 46 of TIC807 is substituted for a serine residue, the amino acid residue corresponding to tyrosine 54 of TIC807 is substituted for a histidine residue, the amino acid residue corresponding to serine 167 of TIC807 is substituted for an arginine residue, the three (3) amino acid residues corresponding to histidine 199 to Serine 201 of TIC807 are deleted, and the amino acid residue corresponding to serine 217 of TIC807 is substituted for an asparagine residue. This comparison of the TIC807 and Cry51Aa1 proteins is shown in FIG. 6.

TABLE 14

| # | Sequence | 1 | 2 |
|---|---|---|---|
| 1 | TIC807 (SEQ ID NO: 5) | — | 97.4 (301) |
| 2 | Cry51Aa1 (SEQ ID NO: 59) | 97.4 (301) | — |

Although the TIC807 protein shares significant sequence identity to the Cry51Aa1 protein, the TIC807 protein surprisingly displayed no significant level of activity when fed to certain lepidopteran insects. Purified TIC807 protein was tested against European Corn Borer (ECB; Ostrinia nubilalis) and tobacco budworm (TBW: Heliothis virescens) and had no activity against either of those lepidopteran insects. The same sample of TIC807 protein displayed activity against Colorado Potato Beetle CPB but not Corn Rootworm (CRW; Diabroticus). Thus the absence of activity of the purified TIC807 against ECB and TBW is not due to inactivity of the purified TIC807 protein.

The present invention thus contemplates TIC807 proteins that are active against hemipteran and coleopteran insects but are inactive against lepidopteran insects. In certain embodiments, the TIC807 proteins of the invention can comprise TIC807 proteins wherein the corresponding residue 54 of the TIC807 protein is not a histidine, wherein the corresponding residue 167 of the TIC807 protein is not an arginine, wherein the three (3) amino acid residues corresponding to histidine 199 to Serine 201 of TIC807 are present, and/or wherein the corresponding residue 217 of the TIC807 is not an asparagine residue. In still other embodiments, the TIC807 protein of the invention can comprise a protein that has at least 98% or at least 99% identity over a length of 301 amino acids corresponding to amino acid residues 2 to 309 of SEQ ID NO:5.

Various patent and non-patent publications are cited herein, the disclosures of each of which are, to the extent necessary, incorporated herein by reference in their entireties. Documents cited herein as being available from the World Wide Web at certain internet addresses are also incorporated herein by reference in their entireties. Certain biological sequences referenced herein by their "NCBI Accession Number" can be accessed through the National Center of Biotechnology Information on the world wide web at ncbi.nlm.nih-.gov.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A recombinant DNA comprising a promoter that functions in a plant cell, a polynucleotide which encodes an insect inhibitory protein, wherein said insect inhibitory protein comprises a polypeptide sequence that has at least 99% sequence identity to SEQ ID NO:5, and a 3' non-translated region containing a polyadenylation signal, wherein said promoter, said polynucleotide, and said 3' non-translated region are operably linked.

2. The recombinant DNA of claim 1, wherein said polypeptide sequence has 100% identity to SEQ ID NO:5.

3. The recombinant DNA of claim 1, wherein said insect inhibitory protein inhibits a Hemipteran insect, a Heteropteran insect, a *Leptinotarsa* sp. insect or a Homopteran insect.

4. The recombinant DNA of claim 3, wherein said Hemipteran insect is *Lygus*.

5. The recombinant DNA of claim 3, wherein said Homopteran insect is an aphid, a hopper, or a whitefly.

6. The recombinant DNA of claim 4, wherein said insect inhibitory protein inhibits *Lygus* at a *Lygus* diet concentration of at least 5 ppm of said protein in said diet.

7. The recombinant DNA of claim 6, wherein said insect inhibitory protein inhibits *Lygus* at a *Lygus* diet concentration of at least 50 ppm of said protein in said diet.

8. The recombinant DNA of claim 7, wherein said insect inhibitory protein inhibits *Lygus* at a *Lygus* diet concentration of at least 250 ppm of said protein in said diet.

9. The recombinant DNA of claim 8, wherein said insect inhibitory protein inhibits *Lygus* at a *Lygus* diet concentration of at least 500 ppm of said protein in said diet.

10. The recombinant DNA of claim 1, wherein said polynucleotide comprises a sequence selected from the group consisting of SEQ ID NO:4, SEQ ID NO:6, SEQ ID NO:7, SEQ ID NO:44, SEQ ID NO: 45, SEQ ID NO:46, SEQ ID NO:47, SEQ ID NO:48, SEQ ID NO:49, SEQ ID NO:50, SEQ ID NO:51, SEQ ID NO:52, and SEQ ID NO:53.

11. The recombinant DNA of claim 1, designed for expression in plants.

12. A transgenic plant or plant part derived therefrom comprising an insect inhibitory protein, wherein said insect inhibitory protein comprises a polypeptide sequence that has at least 99% sequence identity to SEQ ID NO:5.

13. A transformed host cell comprising a polynucleotide which encodes an insect inhibitory protein, wherein said insect inhibitory protein comprises a polypeptide sequence that has at least 99% sequence identity to SEQ ID NO:5.

14. The transformed host cell of claim 13, wherein said host cell is a bacterial cell or a plant cell.

15. A plant derived from the transformed host cell of claim 14, said plant comprising said polynucleotide.

16. A seed produced from the plant of claim 15, said seed comprising said polynucleotide.

17. A progeny plant from the seed of claim 16, said progeny plant comprising said polynucleotide.

* * * * *

SEQUENCE LISTING

<160> NUMBER OF SEQ ID NOS: 59

<210> SEQ ID NO 1
<211> LENGTH: 25
<212> TYPE: PRT
<213> ORGANISM: Bacillus thuringiensis -continued

```
<400> SEQUENCE: 1

Ala Ile Leu Asp Leu Lys Ser Leu Val Leu Asn Ala Ile Asn Tyr Trp
1               5                   10                  15

Gly Pro Lys Asn Asn Asn Glu Ile Gln
            20                  25

<210> SEQ ID NO 2
<211> LENGTH: 30
<212> TYPE: DNA
<213> ORGANISM: Artificial
<220> FEATURE:
<223> OTHER INFORMATION: Synthetic

<400> SEQUENCE: 2
aaygcdatha aytaytgggg dccdaaraay                                    30

<210> SEQ ID NO 3
<211> LENGTH: 30
<212> TYPE: DNA
<213> ORGANISM: Artificial
<220> FEATURE:
<223> OTHER INFORMATION: Synthetic

<400> SEQUENCE: 3
tggggdccda araayaayaa ygaratwcar                                    30

<210> SEQ ID NO 4
<211> LENGTH: 930
<212> TYPE: DNA
<213> ORGANISM: Bacillus thuringiensis

<400> SEQUENCE: 4
ttggcaattt tagatttaaa atctttagta ctcaatgcaa taaattattg gggtcctaaa    60
aataataatg gcatacaggg tggtgatttt ggttacccta tatcagaaaa acaaatagat   120
acgtctatta taacttttac tcatcctcgt ttaattccat atgatttaac aattcctcaa   180
aatttagaaa ctattttttac tacaactcaa gtattaacaa ataatacaga tttacaacaa   240
agtcaaactg tttcttttgc taaaaaaaca acgacaacaa cttcaacttc aactacaaat   300
ggttggacag aaggtgggaa aatttcagat acattagaag aaaaagtaag tgtatctatt   360 cctttttattg gagagggagg aggaaaaaac agtacaacta gaagctaa ttttgcacat    420 aactctagta ctactacttt tcaacaggct tcaactgata tagagtggaa tatttcacaa   480
ccagtattgg ttccccaag taaacaagtt gtagcaacat tagttattat gggaggtaat   540
tttactattc ctatggattt gatgactact atagattcta cagaacatta tagccattat   600
agtggttatc caatattaac atggatatcg agcccgata tagttatag tggtccatt   660 atgagttggt attttgcaaa ttggcccaat ttaccatcgg ggtttggtcc tttaaattca   720
gataatacgg tcacttatac aggttctgtt gtaagtcaag tatcagctgg tgtatatgcc   780
actgtacgat tgatcaata tgatatacac aatttaagga caattgaaaa aacttggtat   840
gcacgacatg caactcttca taatggaaag aaaatatcta taaataatgt tactgaaatg   900
gcaccaacaa gtccaataaa aacaaattaa                                    930

<210> SEQ ID NO 5
<211> LENGTH: 309
<212> TYPE: PRT
<213> ORGANISM: Bacillus thuringiensis

<400> SEQUENCE: 5
```

```
Met Ala Ile Leu Asp Leu Lys Ser Leu Val Leu Asn Ala Ile Asn Tyr
1               5                   10                  15

Trp Gly Pro Lys Asn Asn Asn Gly Ile Gln Gly Gly Asp Phe Gly Tyr
            20                  25                  30

Pro Ile Ser Glu Lys Gln Ile Asp Thr Ser Ile Ile Thr Phe Thr His
        35                  40                  45

Pro Arg Leu Ile Pro Tyr Asp Leu Thr Ile Pro Gln Asn Leu Glu Thr
    50                  55                  60

Ile Phe Thr Thr Thr Gln Val Leu Thr Asn Asn Thr Asp Leu Gln Gln
65              70                  75                  80

Ser Gln Thr Val Ser Phe Ala Lys Lys Thr Thr Thr Thr Thr Ser Thr
                85                  90                  95

Ser Thr Thr Asn Gly Trp Thr Glu Gly Gly Lys Ile Ser Asp Thr Leu
            100                 105                 110

Glu Glu Lys Val Ser Val Ser Ile Pro Phe Ile Gly Glu Gly Gly Gly
            115                 120                 125

Lys Asn Ser Thr Thr Ile Glu Ala Asn Phe Ala His Asn Ser Ser Thr
        130                 135                 140

Thr Thr Phe Gln Gln Ala Ser Thr Asp Ile Glu Trp Asn Ile Ser Gln
145                 150                 155                 160

Pro Val Leu Val Pro Pro Ser Lys Gln Val Val Ala Thr Leu Val Ile
                165                 170                 175

Met Gly Gly Asn Phe Thr Ile Pro Met Asp Leu Met Thr Thr Ile Asp
            180                 185                 190

Ser Thr Glu His Tyr Ser His Tyr Ser Gly Tyr Pro Ile Leu Thr Trp
            195                 200                 205

Ile Ser Ser Pro Asp Asn Ser Tyr Ser Gly Pro Phe Met Ser Trp Tyr
210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
                245                 250                 255

Gly Val Tyr Ala Thr Val Arg Phe Asp Gln Tyr Asp Ile His Asn Leu
            260                 265                 270

Arg Thr Ile Glu Lys Thr Trp Tyr Ala Arg His Ala Thr Leu His Asn
        275                 280                 285

Gly Lys Lys Ile Ser Ile Asn Asn Val Thr Glu Met Ala Pro Thr Ser
    290                 295                 300

Pro Ile Lys Thr Asn
305
```

<210> SEQ ID NO 6
<211> LENGTH: 930
<212> TYPE: DNA
<213> ORGANISM: Artificial
<220> FEATURE:
<223> OTHER INFORMATION: Synthetic

<400> SEQUENCE: 6

```
atggctatcc tagaccttaa gtccctcgtg ctgaacgcca ttaactactg gggccctaag     60
aacaacaacg gcatccaggg cggtgacttc ggctaccccc tctctgagaa gcagatcgac    120
actagcatca ttaccttcac ccaccctcgc ttgatcccct acgatcttac tatcccgcag    180
aaccttgaga ccatcttcac cacaacgcag gtgctcacca ataacactga cctccagcaa    240
tcccagaccg tgagctttgc gaagaagacc actaccacga cctcaactag cacgaccaac    300
```

```
ggttggacag aaggaggcaa gatcagcgac acgctggagg agaaagtttc ggttagcatt      360
ccgttcatcg gtgagggtgg cgggaagaac tcgactacca tagaggccaa cttcgcacac      420
aactctagca ccactacctt ccagcaagca agcactgaca ttgagtggaa cattagccaa      480
ccggtgctgg ttcctccctc taaacaagtt gtcgcgaccc ttgtgatcat gggaggcaac      540
tttaccatcc ctatggactt gatgaccacg attgatagta cagagcacta ctcccactac      600
tccggttacc ctatcctcac ctggatctcg tccccagata actcttactc cggtcccttt      660
atgtcatggt actttgcaaa ctggcctaac cttccgagtg gattcggccc actgaatagt      720
gataacacgg tcacatacac tggctctgtc gtgtcccaag tttcggccgg tgtctacgct      780
accgtccggt tcgatcagta tgacattcac aatctccgta ctatcgagaa gacttggtat      840
gctcgccatg cgacgctgca taatggcaag aagatttcta tcaacaatgt cacggaaatg      900
gctccaacat cccctatcaa gacaaattga                                      930

<210> SEQ ID NO 7
<211> LENGTH: 1158
<212> TYPE: DNA
<213> ORGANISM: Artificial
<220> FEATURE:
<223> OTHER INFORMATION: Synthetic

<400> SEQUENCE: 7
atggcgcaag ttagcagaat ctgcaatggt gtgcagaacc catctcttat ctccaatctc       60
tcgaaatcca gtcaacgcaa atctccctta tcggtttctc tgaagacgca gcagcatcca      120
cgagcttatc cgatttcgtc gtcgtgggga ttgaagaaga gtgggatgac gttaattggc      180
tctgagcttc gtcctcttaa ggtcatgtct tctgtttcca cggcgtgcat ggctatccta      240
gaccttaagt ccctcgtgct gaacgccatt aactactggg gccctaagaa caacaacggc      300
atccagggcg gtgacttcgg ctaccccatc tctgagaagc agatcgacac tagcatcatt      360
accttcaccc ccctcgctt gatcccctac gatcttacta tcccgcagaa ccttgagacc      420
atcttcacca caacgcaggt gctcaccaat aacactgacc tccagcaatc ccagaccgtg      480
agctttgcga agaagaccac taccacgacc tcaactagca cgaccaacgg ttggacagaa      540
ggaggcaaga tcagcgacac gctggaggag aaagtttcgg ttagcattcc gttcatcggt      600
gagggtggcg gaagaactc gactaccata gaggccaact cgcacacaa ctctagcacc      660 actaccttcc agcaagcaag cactgacatt gagtggaaca ttagccaacc ggtgctggtt      720
cctccctcta aacaagttgt cgctacccctt gtgatcatgg gaggcaactt taccatccct      780
atggacttga tgaccacgat tgatagtaca gagcactact cccactactc cggttaccct      840
atcctcacct ggatctcgtc cccagataac tcttactccg gtcccttat gtcatggtac      900 tttgcaaact ggcctaacct tccgagtgga ttcggcccac tgaatagtga taacacggtc      960
acatacactg gctctgtcgt gtcccaagtt tcggccggtg tctacgctac cgtccggttc     1020
gatcagtatg acattcacaa tctccgtact atcgagaaga cttggtatgc tcgccatgcg     1080
acgctgcata atggcaagaa gatttctatc aacaatgtca cggaaatggc tccaacatcc     1140
cctatcaaga caaattga                                                  1158

<210> SEQ ID NO 8
<211> LENGTH: 385
<212> TYPE: PRT
<213> ORGANISM: Artificial
<220> FEATURE:
<223> OTHER INFORMATION: Synthetic
```

<400> SEQUENCE: 8

```
Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
50                  55                  60

Pro Leu Lys Val Met Ser Ser Val Ser Thr Ala Cys Met Ala Ile Leu
65                  70                  75                  80

Asp Leu Lys Ser Leu Val Leu Asn Ala Ile Asn Tyr Trp Gly Pro Lys
                85                  90                  95

Asn Asn Asn Gly Ile Gln Gly Gly Asp Phe Gly Tyr Pro Ile Ser Glu
            100                 105                 110

Lys Gln Ile Asp Thr Ser Ile Ile Thr Phe Thr His Pro Arg Leu Ile
        115                 120                 125

Pro Tyr Asp Leu Thr Ile Pro Gln Asn Leu Glu Thr Ile Phe Thr Thr
130                 135                 140

Thr Gln Val Leu Thr Asn Asn Thr Asp Leu Gln Gln Ser Gln Thr Val
145                 150                 155                 160

Ser Phe Ala Lys Lys Thr Thr Thr Thr Ser Thr Ser Thr Thr Thr Asn
                165                 170                 175

Gly Trp Thr Glu Gly Gly Lys Ile Ser Asp Thr Leu Glu Gly Lys Val
            180                 185                 190

Ser Val Ser Ile Pro Phe Ile Gly Glu Gly Gly Lys Asn Ser Thr
        195                 200                 205

Thr Ile Glu Ala Asn Phe Ala His Asn Ser Ser Thr Thr Thr Phe Gln
210                 215                 220

Gln Ala Ser Thr Asp Ile Glu Trp Asn Ile Ser Gln Pro Val Leu Val
225                 230                 235                 240

Pro Pro Ser Lys Gln Val Val Ala Thr Leu Val Ile Met Gly Gly Asn
                245                 250                 255

Phe Thr Ile Pro Met Asp Leu Met Thr Thr Ile Asp Ser Thr Glu His
            260                 265                 270

Tyr Ser His Tyr Ser Gly Tyr Pro Ile Leu Thr Trp Ile Ser Ser Pro
        275                 280                 285

Asp Asn Ser Tyr Ser Gly Pro Phe Met Ser Trp Tyr Phe Ala Asn Trp
290                 295                 300

Pro Asn Leu Pro Ser Gly Phe Gly Pro Leu Asn Ser Asp Asn Thr Val
305                 310                 315                 320

Thr Tyr Thr Gly Ser Val Val Ser Gln Val Ser Ala Gly Val Tyr Ala
                325                 330                 335

Thr Val Arg Phe Asp Gln Tyr Asp Ile His Asn Leu Arg Thr Ile Glu
            340                 345                 350

Lys Thr Trp Tyr Ala Arg His Ala Thr Leu His Asn Gly Lys Lys Ile
        355                 360                 365

Ser Ile Asn Asn Val Thr Glu Met Ala Pro Thr Ser Pro Ile Lys Thr
370                 375                 380

Asn
385
```

<210> SEQ ID NO 9
<211> LENGTH: 702

<212> TYPE: DNA
<213> ORGANISM: Artificial
<220> FEATURE:
<223> OTHER INFORMATION: Synthetic

<400> SEQUENCE: 9

```
atggctttct tcaacagggt tatcaccctg accgtgccta gctctgacgt ggtgaactac    60
tctgaaatct accaagttgc ccctcagtac gtgaaccagg ccctgaccct agccaagtac   120
ttccagggtg ccattgacgg tagcaccctt agattcgact cgagaaggc cctccagatc    180
gccaacgaca tcccacaggc cgctgtggtc aacacccctca accagaccgt gcagcaaggc   240
accgtgcaag tgagcgtgat gatcgacaag atcgtggaca tcatgaagaa cgtgctctcc   300
atcgtgatcg acaacaagaa attctgggac caagtgaccg ccgctatcac caacaccttc   360
accaacctca actcccagga gtccgaggct tggatcttct actacaagga ggacgcccac   420
aagacctcct actattacaa catcctcttc gccatccagg acgaggaaac aggcggtgtg   480
atggctacac tcccccatcgc tttcgacatc tccgtggaca tcgagaagga gaaagtcctc   540
ttcgtcacca tcaaggacac cgagaactac gctgtcactg tcaaggctat caacgtcgtt   600
caggctctcc agtccagccg cgactccaaa gtcgttgacg cttcaagtc tcccaggcac    660
ctccctagga agaggcacaa gatttgcagc aacagctgat aa                      702
```

<210> SEQ ID NO 10
<211> LENGTH: 232
<212> TYPE: PRT
<213> ORGANISM: Artificial
<220> FEATURE:
<223> OTHER INFORMATION: Synthetic

<400> SEQUENCE: 10

```
Met Ala Phe Phe Asn Arg Val Ile Thr Leu Thr Val Pro Ser Ser Asp
1               5                   10                  15

Val Val Asn Tyr Ser Glu Ile Tyr Gln Val Ala Pro Gln Tyr Val Asn
            20                  25                  30

Gln Ala Leu Thr Leu Ala Lys Tyr Phe Gln Gly Ala Ile Asp Gly Ser
        35                  40                  45

Thr Leu Arg Phe Asp Phe Glu Lys Ala Leu Gln Ile Ala Asn Asp Ile
    50                  55                  60

Pro Gln Ala Ala Val Val Asn Thr Leu Asn Gln Thr Val Gln Gln Gly
65                  70                  75                  80

Thr Val Gln Val Ser Val Met Ile Asp Lys Ile Val Asp Ile Met Lys
                85                  90                  95

Asn Val Leu Ser Ile Val Ile Asp Asn Lys Lys Phe Trp Asp Gln Val
            100                 105                 110

Thr Ala Ala Ile Thr Asn Thr Phe Thr Asn Leu Asn Ser Gln Glu Ser
        115                 120                 125

Glu Ala Trp Ile Phe Tyr Tyr Lys Glu Asp Ala His Lys Thr Ser Tyr
    130                 135                 140

Tyr Tyr Asn Ile Leu Phe Ala Ile Gln Asp Glu Glu Thr Gly Gly Val
145                 150                 155                 160

Met Ala Thr Leu Pro Ile Ala Phe Asp Ile Ser Val Asp Ile Glu Lys
                165                 170                 175

Glu Lys Val Leu Phe Val Thr Ile Lys Asp Thr Glu Asn Tyr Ala Val
            180                 185                 190

Thr Val Lys Ala Ile Asn Val Val Gln Ala Leu Gln Ser Ser Arg Asp
        195                 200                 205
```

```
Ser Lys Val Val Asp Ala Phe Lys Ser Pro Arg His Leu Pro Arg Lys
    210                 215                 220

Arg His Lys Ile Cys Ser Asn Ser
225                 230
```

<210> SEQ ID NO 11
<211> LENGTH: 660
<212> TYPE: DNA
<213> ORGANISM: Artificial
<220> FEATURE:
<223> OTHER INFORMATION: Synthetic

<400> SEQUENCE: 11

```
atgagcaagg agatccgtct caacctctct cgggagtctg gcgcggacct ctacctgaag    60
atcctggcgt tcgtcaagcc cgagcatttc tttcaggcgt acctgctttg ccggagttc    120 gagtctatcg tcgatccgac tactagagag tcagatttcg ataagactct gactattgtc    180
aagtcggatt ctactctggt cactgtcggc actatgaaca ctaagctggt caactcgcaa    240
gagattctgg tctcggatct gattactcaa gttggtagtc agattgcgga tacgctgggc    300
attacggaca ttgatgcaaa cacacagcaa caactgacag agcttattgg gaatcttttc    360
gttaatctta atagtcaagt tcaagagtac atctacttct acgaagagaa ggagaagcaa    420
acgtcatatc gttacaacat tctctttgtt ttcgagaagg aatcattcat taccatactt    480
ccaatgggat tgatgttac ggtgaacaca ataaggaag cagttctaaa gttgacacca    540
aaggataaag ttacttatgg acacgtatca gtaaaggcac ttaatatcat tcaacttatc    600
acagaagata aattcaattt tctcgcaaca ctcaagaagg ctttgaagac cttgtgataa   660
```

<210> SEQ ID NO 12
<211> LENGTH: 218
<212> TYPE: PRT
<213> ORGANISM: Artificial
<220> FEATURE:
<223> OTHER INFORMATION: Synthetic

<400> SEQUENCE: 12

```
Met Ser Lys Glu Ile Arg Leu Asn Leu Ser Arg Glu Ser Gly Ala Asp
1               5                   10                  15

Leu Tyr Leu Lys Ile Leu Ala Phe Val Lys Pro Glu His Phe Phe Gln
                20                  25                  30

Ala Tyr Leu Leu Cys Arg Glu Phe Glu Ser Ile Val Asp Pro Thr Thr
            35                  40                  45

Arg Glu Ser Asp Phe Asp Lys Thr Leu Thr Ile Val Lys Ser Asp Ser
        50                  55                  60

Thr Leu Val Thr Val Gly Thr Met Asn Thr Lys Leu Val Asn Ser Gln
65                  70                  75                  80

Glu Ile Leu Val Ser Asp Leu Ile Thr Gln Val Gly Ser Gln Ile Ala
                85                  90                  95

Asp Thr Leu Gly Ile Thr Asp Ile Asp Ala Asn Thr Gln Gln Gln Leu
            100                 105                 110

Thr Glu Leu Ile Gly Asn Leu Phe Val Asn Leu Asn Ser Gln Val Gln
        115                 120                 125

Glu Tyr Ile Tyr Phe Tyr Glu Glu Lys Glu Lys Gln Thr Ser Tyr Arg
    130                 135                 140

Tyr Asn Ile Leu Phe Val Phe Glu Lys Glu Ser Phe Ile Thr Ile Leu
145                 150                 155                 160

Pro Met Gly Phe Asp Val Thr Val Asn Thr Asn Lys Glu Ala Val Leu
                165                 170                 175
```

```
Lys Leu Thr Pro Lys Asp Lys Val Thr Tyr Gly His Val Ser Val Lys
            180                 185                 190

Ala Leu Asn Ile Ile Gln Leu Ile Thr Glu Asp Lys Phe Asn Phe Leu
        195                 200                 205

Ala Thr Leu Lys Lys Ala Leu Lys Thr Leu
        210                 215
```

<210> SEQ ID NO 13
<211> LENGTH: 1413
<212> TYPE: DNA
<213> ORGANISM: Artificial
<220> FEATURE:
<223> OTHER INFORMATION: Synthetic

<400> SEQUENCE: 13

```
atggctttct tcaacagggt tatcaccctg accgtgccta gctctgacgt ggtgaactac      60
tctgaaatct accaagttgc ccctcagtac gtgaaccagg ccctgaccct agccaagtac     120
ttccagggtg ccattgacgg tagcacccct agattcgact cgagaaggc cctccagatc     180
gccaacgaca tcccacaggc cgctgtggtc aacaccctca accagaccgt gcagcaaggc     240
accgtgcaag tgagcgtgat gatcgacaag atcgtggaca tcatgaagaa cgtgctctcc     300
atcgtgatcg acaacaagaa attctgggac caagtgaccg ccgctatcac caacaccttc     360
accaacctca actcccagga gtccgaggct tggatcttct actacaagga ggacgcccac     420
aagacctcct actattacaa catcctcttc gccatccagg acgaggaaac aggcggtgtg     480
atggctacac tccccatcgc tttcgacatc tccgtggaca tcgagaagga gaaagtcctc     540
ttcgtcacca tcaaggacac cgagaactac gctgtcactg tcaaggctat caacgtcgtt     600
caggctctcc agtccagccg cgactccaaa gtcgttgacg ctttcaagtc tcccaggcac     660
ctccctagga gaggcacaa gatttgcagc aacagcaagc ctgctttgct taaggaagct     720
cctagggcag aagaggagtt gcctccacgt aagatgagca aggagatccg tctcaacctc     780
tctcgggagt ctggcgcgga cctctacctg aagatcctgg cgttcgtcaa gcccgagcat     840
ttctttcagg cgtacctgct tgccgggag ttcgagtcta tcgtcgatcc gactactaga     900
gagtcagatt tcgataagac tctgactatt gtcaagtcgg attctactct ggtcactgtc     960
ggcactatga acactaagct ggtcaactcg caagagattc tggtctcgga tctgattact    1020
caagttggta gtcagattgc ggatacgctg gcattacgg acattgatgc aaacacacag    1080
caacaactga cagagcttat tgggaatctt ttcgttaatc ttaatagtca agttcaagag    1140
tacatctact tctacgaaga aaggagaag caaacgtcat atcgttacaa cattctcttt    1200
gttttcgaga aggaatcatt cattaccata cttccaatgg gatttgatgt tacggtgaac    1260
acaaataagg aagcagttct aaagttgaca ccaaaggata aagttactta tggacacgta    1320
tcagtaaagg cacttaatat cattcaactt atcacagaag ataaattcaa ttttctcgca    1380
acactcaaga aggctttgaa gaccttgtga taa                                1413
```

<210> SEQ ID NO 14
<211> LENGTH: 469
<212> TYPE: PRT
<213> ORGANISM: Artificial
<220> FEATURE:
<223> OTHER INFORMATION: Synthetic

<400> SEQUENCE: 14

```
Met Ala Phe Phe Asn Arg Val Ile Thr Leu Thr Val Pro Ser Ser Asp
1               5                   10                  15
```

-continued

```
Val Val Asn Tyr Ser Glu Ile Tyr Gln Val Ala Pro Gln Tyr Val Asn
             20                  25                  30

Gln Ala Leu Thr Leu Ala Lys Tyr Phe Gln Gly Ala Ile Asp Gly Ser
         35                  40                  45

Thr Leu Arg Phe Asp Phe Glu Lys Ala Leu Gln Ile Ala Asn Asp Ile
     50                  55                  60

Pro Gln Ala Ala Val Val Asn Thr Leu Asn Gln Thr Val Gln Gln Gly
 65                  70                  75                  80

Thr Val Gln Val Ser Val Met Ile Asp Lys Ile Val Asp Ile Met Lys
                 85                  90                  95

Asn Val Leu Ser Ile Val Ile Asp Asn Lys Lys Phe Trp Asp Gln Val
            100                 105                 110

Thr Ala Ala Ile Thr Asn Thr Phe Thr Asn Leu Asn Ser Gln Glu Ser
            115                 120                 125

Glu Ala Trp Ile Phe Tyr Tyr Lys Glu Asp Ala His Lys Thr Ser Tyr
        130                 135                 140

Tyr Tyr Asn Ile Leu Phe Ala Ile Gln Asp Glu Glu Thr Gly Gly Val
145                 150                 155                 160

Met Ala Thr Leu Pro Ile Ala Phe Asp Ile Ser Val Asp Ile Glu Lys
                165                 170                 175

Glu Lys Val Leu Phe Val Thr Ile Lys Asp Thr Glu Asn Tyr Ala Val
            180                 185                 190

Thr Val Lys Ala Ile Asn Val Val Gln Ala Leu Gln Ser Ser Arg Asp
        195                 200                 205

Ser Lys Val Val Asp Ala Phe Lys Ser Pro Arg His Leu Pro Arg Lys
    210                 215                 220

Arg His Lys Ile Cys Ser Asn Ser Lys Pro Ala Leu Leu Lys Glu Ala
225                 230                 235                 240

Pro Arg Ala Glu Glu Glu Leu Pro Pro Arg Lys Met Ser Lys Glu Ile
                245                 250                 255

Arg Leu Asn Leu Ser Arg Glu Ser Gly Ala Asp Leu Tyr Leu Lys Ile
            260                 265                 270

Leu Ala Phe Val Lys Pro Glu His Phe Phe Gln Ala Tyr Leu Leu Cys
        275                 280                 285

Arg Glu Phe Glu Ser Ile Val Asp Pro Thr Thr Arg Glu Ser Asp Phe
    290                 295                 300

Asp Lys Thr Leu Thr Ile Val Lys Ser Asp Ser Thr Leu Val Thr Val
305                 310                 315                 320

Gly Thr Met Asn Thr Lys Leu Val Asn Ser Gln Glu Ile Leu Val Ser
                325                 330                 335

Asp Leu Ile Thr Gln Val Gly Ser Gln Ile Ala Asp Thr Leu Gly Ile
            340                 345                 350

Thr Asp Ile Asp Ala Asn Thr Gln Gln Gln Leu Thr Glu Leu Ile Gly
        355                 360                 365

Asn Leu Phe Val Asn Leu Asn Ser Gln Val Gln Glu Tyr Ile Tyr Phe
    370                 375                 380

Tyr Glu Glu Lys Glu Lys Gln Thr Ser Tyr Arg Tyr Asn Ile Leu Phe
385                 390                 395                 400

Val Phe Glu Lys Glu Ser Phe Ile Thr Ile Leu Pro Met Gly Phe Asp
                405                 410                 415

Val Thr Val Asn Thr Asn Lys Glu Ala Val Leu Lys Leu Thr Pro Lys
            420                 425                 430

Asp Lys Val Thr Tyr Gly His Val Ser Val Lys Ala Leu Asn Ile Ile
```

```
               435                 440                 445
Gln Leu Ile Thr Glu Asp Lys Phe Asn Phe Leu Ala Thr Leu Lys Lys
                450                 455                 460

Ala Leu Lys Thr Leu
465

<210> SEQ ID NO 15
<211> LENGTH: 1413
<212> TYPE: DNA
<213> ORGANISM: Artificial
<220> FEATURE:
<223> OTHER INFORMATION: Synthetic

<400> SEQUENCE: 15
atgagcaagg agatccgtct caacctctct cgggagtctg gcgcggacct ctacctgaag      60
atcctggcgt tcgtcaagcc cgagcatttc tttcaggcgt acctgctttg ccgggagttc     120
gagtctatcg tcgatccgac tactagagag tcagatttcg ataagactct gactattgtc     180
aagtcggatt ctactctggt cactgtcggc actatgaaca ctaagctggt caactcgcaa     240
gagattctgg tctcggatct gattactcaa gttggtagtc agattgcgga tacgctgggc     300
attacggaca ttgatgcaaa cacacagcaa caactgacag agcttattgg gaatcttttc     360
gttaatctta atagtcaagt tcaagagtac atctacttct acgaagagaa ggagaagcaa     420
acgtcatatc gttacaacat tctctttgtt ttcgagaagg aatcattcat taccatactt     480
ccaatgggat ttgatgttac ggtgaacaca aataaggaag cagttctaaa gttgacacca     540
aaggataaag ttacttatgg acacgtatca gtaaaggcac ttaatatcat tcaacttatc     600
acagaagata aattcaattt tctcgcaaca ctcaagaagg cttttgaagac cttgaagcct     660 gctttgctta aggaagctcc tagggcagaa gaggagttgc ctccacgtaa gatggctttc     720
ttcaacaggg ttatcaccct gaccgtgcct agctctgacg tggtgaacta ctctgaaatc     780
taccaagttg ccccctcagta cgtgaaccag gccctgaccc tagccaagta cttccagggt     840
gccattgacg gtagcaccct tagattcgac ttcgagaagg ccctccagat cgccaacgac     900
atcccacagg ccgctgtggt caacaccctc aaccagaccg tgcagcaagg caccgtgcaa     960
gtgagcgtga tgatcgacaa gatcgtggac atcatgaaga acgtgctctc catcgtgatc    1020
gacaacaaga aattctggga ccaagtgacc gccgctatca ccaacacctt caccaacctc    1080
aactcccagg agtccgaggc ttggatcttc tactacaagg aggacgccca agaccctcc     1140 tactattaca acatcctctt cgccatccag gacgaggaaa caggcggtgt gatggctaca    1200
ctccccatcg ctttcgacat ctccgtggac atcgagaagg agaaagtcct cttcgtcacc    1260
atcaaggaca ccgagaacta cgctgtcact gtcaaggcta tcaacgtcgt tcaggctctc    1320
cagtccagcc gcgactccaa agtcgttgac gctttcaagt ctcccaggca cctccctagg    1380
aagaggcaca gatttgcag caacagctga taa                                  1413

<210> SEQ ID NO 16
<211> LENGTH: 469
<212> TYPE: PRT
<213> ORGANISM: Artificial
<220> FEATURE:
<223> OTHER INFORMATION: Synthetic

<400> SEQUENCE: 16

Met Ser Lys Glu Ile Arg Leu Asn Leu Ser Arg Glu Ser Gly Ala Asp
1               5                   10                  15

Leu Tyr Leu Lys Ile Leu Ala Phe Val Lys Pro Glu His Phe Phe Gln
```

-continued

```
                20                  25                  30
Ala Tyr Leu Leu Cys Arg Glu Phe Glu Ser Ile Val Asp Pro Thr Thr
            35                  40                  45
Arg Glu Ser Asp Phe Asp Lys Thr Leu Thr Ile Val Lys Ser Asp Ser
50                  55                  60
Thr Leu Val Thr Val Gly Thr Met Asn Thr Lys Leu Val Asn Ser Gln
65                  70                  75                  80
Glu Ile Leu Val Ser Asp Leu Ile Thr Gln Val Gly Ser Gln Ile Ala
                85                  90                  95
Asp Thr Leu Gly Ile Thr Asp Ile Asp Ala Asn Thr Gln Gln Gln Leu
            100                 105                 110
Thr Glu Leu Ile Gly Asn Leu Phe Val Asn Leu Asn Ser Gln Val Gln
            115                 120                 125
Glu Tyr Ile Tyr Phe Tyr Glu Glu Lys Glu Lys Gln Thr Ser Tyr Arg
            130                 135                 140
Tyr Asn Ile Leu Phe Val Phe Glu Lys Glu Ser Phe Ile Thr Ile Leu
145                 150                 155                 160
Pro Met Gly Phe Asp Val Thr Val Asn Thr Asn Lys Glu Ala Val Leu
                165                 170                 175
Lys Leu Thr Pro Lys Asp Lys Val Thr Tyr Gly His Val Ser Val Lys
            180                 185                 190
Ala Leu Asn Ile Ile Gln Leu Ile Thr Glu Asp Lys Phe Asn Phe Leu
            195                 200                 205
Ala Thr Leu Lys Lys Ala Leu Lys Thr Leu Lys Pro Ala Leu Leu Lys
            210                 215                 220
Glu Ala Pro Arg Ala Glu Glu Leu Pro Pro Arg Lys Met Ala Phe
225                 230                 235                 240
Phe Asn Arg Val Ile Thr Leu Thr Val Pro Ser Ser Asp Val Val Asn
                245                 250                 255
Tyr Ser Glu Ile Tyr Gln Val Ala Pro Gln Tyr Val Asn Gln Ala Leu
            260                 265                 270
Thr Leu Ala Lys Tyr Phe Gln Gly Ala Ile Asp Gly Ser Thr Leu Arg
            275                 280                 285
Phe Asp Phe Glu Lys Ala Leu Gln Ile Ala Asn Asp Ile Pro Gln Ala
            290                 295                 300
Ala Val Val Asn Thr Leu Asn Gln Thr Val Gln Gln Gly Thr Val Gln
305                 310                 315                 320
Val Ser Val Met Ile Asp Lys Ile Val Asp Ile Met Lys Asn Val Leu
                325                 330                 335
Ser Ile Val Ile Asp Asn Lys Lys Phe Trp Asp Gln Val Thr Ala Ala
            340                 345                 350
Ile Thr Asn Thr Phe Thr Asn Leu Asn Ser Gln Glu Ser Glu Ala Trp
            355                 360                 365
Ile Phe Tyr Tyr Lys Glu Asp Ala His Lys Thr Ser Tyr Tyr Tyr Asn
            370                 375                 380
Ile Leu Phe Ala Ile Gln Asp Glu Glu Thr Gly Gly Val Met Ala Thr
385                 390                 395                 400
Leu Pro Ile Ala Phe Asp Ile Ser Val Asp Ile Glu Lys Glu Lys Val
                405                 410                 415
Leu Phe Val Thr Ile Lys Asp Thr Glu Asn Tyr Ala Val Thr Val Lys
            420                 425                 430
Ala Ile Asn Val Val Gln Ala Leu Gln Ser Ser Arg Asp Ser Lys Val
            435                 440                 445
```

Val Asp Ala Phe Lys Ser Pro Arg His Leu Pro Arg Lys Arg His Lys
        450                 455                 460

Ile Cys Ser Asn Ser
465

<210> SEQ ID NO 17
<211> LENGTH: 57
<212> TYPE: DNA
<213> ORGANISM: Artificial
<220> FEATURE:
<223> OTHER INFORMATION: Synthetic

<400> SEQUENCE: 17
aagcctgctt tgcttaagga agctcctagg gcagaagagg agttgcctcc acgtaag    57

<210> SEQ ID NO 18
<211> LENGTH: 19
<212> TYPE: PRT
<213> ORGANISM: Artificial
<220> FEATURE:
<223> OTHER INFORMATION: Synthetic

<400> SEQUENCE: 18

Lys Pro Ala Leu Leu Lys Glu Ala Pro Arg Ala Glu Glu Glu Leu Pro
1               5                   10                  15

Pro Arg Lys

<210> SEQ ID NO 19
<211> LENGTH: 980
<212> TYPE: DNA
<213> ORGANISM: Artificial
<220> FEATURE:
<223> OTHER INFORMATION: Synthetic

<400> SEQUENCE: 19
ccatggctat cctagacctt aagtccctcg tgctgaacgc cattaactac tggggcccta      60
agaacaacaa cggcatccag ggcggtgact tcggctaccc catctctgag aagcagatcg     120
acactagcat cattaccttc acccacccte gcttgatccc ctacgatctt actatcccgc     180
agaaccttga ccatcttcc accacaacgc aggtgctcac caataacact gacctccagc     240
aatcccagac cgtgagcttt gcgaagaaga ccactaccac gacctcaact agcacgacca     300
acggttggac agaaggaggc aagatcagcg acacgctgga ggagaaagtt tcggttagca     360
ttccgttcat cggtgagggt ggcgggaaga actcgactac catagaggcc aacttcgcac     420
acaactctag caccactacc ttccagcaag caagcactga cattgagtgg aacattagcc     480
aaccggtgct ggttcctccc tctaaacaag ttgtcgcgac ccttgtgatc atggaggca     540
actttaccat ccctatggac ttgatgacca cgattgatag tacagagcac tactcccact     600
actccggtta ccctatcctc acctggatct cgtccccaga taactcttac tccggtccct     660
ttatgtcatg gtactttgca aactggccta accttccgag tggattcggc ccactgaata     720
gtgataacac ggtcacatac actggctctg tcgtgtccca gtttcggcc ggtgtctacg     780
ctaccgtccg gttcgatcag tatgacattc acaatctccg tactatcgag aagacttggt     840
atgctcgcca tgcgacgctg cataatggca agaagatttc tatcaacaat gtcacggaaa     900
tggctccaac atcccctatc aagacaaatg agcaaaagtt gatttctgag gaggatttgt     960
gaggatccaa ttcccgatcg                                                 980

<210> SEQ ID NO 20
<211> LENGTH: 1924

```
<212> TYPE: DNA
<213> ORGANISM: Artificial
<220> FEATURE:
<223> OTHER INFORMATION: Synthetic

<400> SEQUENCE: 20
ggtccgattg agactttca acaaagggta atatccggaa acctcctcgg attccattgc      60
ccagctatct gtcactttat tgtgaagata gtggaaaagg aaggtggctc ctacaaatgc    120
catcattgcg ataaaggaaa ggccatcgtt gaagatgcct ctgccgacag tggtcccaaa    180
gatggaccc cacccacgag gagcatcgtg aaaaagaag acgttccaac cacgtcttca    240
aagcaagtgg attgatgtga tggtccgatt gagactttc aacaaagggt aatatccgga    300
aacctcctcg gattccattg cccagctatc tgtcacttta ttgtgaagat agtggaaaag    360
gaaggtggct cctacaaatg ccatcattgc gataaaggaa aggccatcgt tgaagatgcc    420
tctgccgaca gtggtcccaa agatggaccc cacccacga ggagcatcgt ggaaaagaa    480
gacgttccaa ccacgtcttc aaagcaagtg gattgatgtg atatctccac tgacgtaagg    540
gatgacgcac aatcccacta tccttcgcaa gacccttcct ctatataagg aagttcattt    600
catttggaga ggacacgctg acaagctgac tctagcagat atcaaacaag tttgtacaaa    660
aaagcaggct ccgcggccgc ccccttcacc agatctccat ggctatccta gaccttaagt    720
ccctcgtgct gaacgccatt aactactggg ccctaagaa caacaacggc atccagggcg    780
gtgacttcgg ctaccccatc tctgagaagc agatcgacac tagcatcatt accttcaccc    840
accctcgctt gatcccctac gatcttacta cccgcagaa ccttgagacc atcttcacca    900
caacgcaggt gctcaccaat aacactgacc tccagcaatc ccagaccgtg agctttgcga    960
agaagaccac taccacgacc tcaactagca cgaccaacgg ttggacagaa ggaggcaaga   1020
tcagcgacac gctggaggag aaagtttcgg ttagcattcc gttcatcggt gagggtggcg   1080
ggaagaactc gactaccata gaggccaact tcgcacacaa ctctagcacc actaccttcc   1140
agcaagcaag cactgacatt gagtggaaca ttagccaacc ggtgctggtt cctccctcta   1200
aacaagttgt cgcgaccctt gtgatcatgg gaggcaactt taccatccct atggacttga   1260
tgaccacgat tgatagtaca gagcactact cccactactc cggttaccct atcctcacct   1320
ggatctcgtc cccagataac tcttactccg gtccctttat gtcatggtac tttgcaaact   1380
ggcctaacct tccgagtgga ttcggcccac tgaatagtga taacacggtc acatacactg   1440
gctctgtcgt gtcccaagtt tcggccggtg tctacgctac cgtccggttc gatcagtatg   1500
acattcacaa tctccgtact atcgagaaga cttggtatgc tcgccatgcg acgctgcata   1560
atggcaagaa gatttctatc aacaatgtca cggaaatggc tccaacatcc cctatcaaga   1620
caaatgagca aaagttgatt tctgaggagg atttgtgagg atccaattcc cgatcgttca   1680
aacatttggc aataaagttt cttaagattg aatcctgttg ccggtcttgc gatgattatc   1740
atataatttc tgttgaatta cgttaagcat gtaataatta acatgtaatg catgacgtta   1800
tttatgagat gggtttttat gattagagtc ccgcaattat acatttaata cgcgatagaa   1860
aacaaaatat agcgcgcaaa ctaggataaa ttatcgcgcg cggtgtcatc tatgttacta   1920
gatc                                                                1924

<210> SEQ ID NO 21
<211> LENGTH: 1196
<212> TYPE: DNA
<213> ORGANISM: Artificial
<220> FEATURE:
<223> OTHER INFORMATION: Synthetic
```

<400> SEQUENCE: 21

```
ccatggcgca agttagcaga atctgcaatg gtgtgcagaa cccatctctt atctccaatc    60
tctcgaaatc cagtcaacgc aaatctccct tatcggtttc tctgaagacg cagcagcatc   120
cacgagctta tccgatttcg tcgtcgtggg gattgaagaa gagtgggatg acgttaattg   180
gctctgagct tcgtcctctt aaggtcatgt cttctgtttc cacggcgtgc atggctatcc   240
tagaccttaa gtccctcgtg ctgaacgcca ttaactactg gggccctaag aacaacaacg   300
gcatccaggg cggtgacttc ggctacccca tctctgagaa gcagatcgac actagcatca   360
ttaccttcac ccaccctcgc ttgatcccct acgatcttac tatcccgcag aaccttgaga   420
ccatcttcac cacaacgcag gtgctcacca ataacactga cctccagcaa tcccagaccg   480
tgagctttgc gaagaagacc actaccacga cctcaactag cacgaccaac ggttggacag   540
aaggaggcaa gatcagcgac acgctggagg agaaagtttc ggttagcatt ccgttcatcg   600
gtgagggtgg cgggaagaac tcgactacca tagaggccaa cttcgcacac aactctagca   660
ccactacctt ccagcaagca agcactgaca ttgagtggaa cattagccaa ccggtgctgg   720
ttcctccctc taaacaagtt gtcgcgaccc ttgtgatcat gggaggcaac tttaccatcc   780
ctatggactt gatgaccacg attgatagta cagagcacta ctcccactac tccggttacc   840
ctatcctcac ctgatctcg tccccagata actcttactc cggtcccttt atgtcatggt   900
actttgcaaa ctggcctaac cttccgagtg gattcggccc actgaatagt gataacacgg   960
tcacatacac tggctctgtc gtgtcccaag tttcggccgg tgtctacgct accgtccggt  1020
tcgatcagta tgacattcac aatctccgta ctatcgaaa gacttggtat gctcgccatg  1080
cgacgctgca taatggcaag aagatttcta tcaacaatgt cacggaaatg gctccaacat  1140
ccccctatcaa gacaaatgag caaaagttga tttctgagga ggatttgtga ggatcc     1196
```

<210> SEQ ID NO 22
<211> LENGTH: 2152
<212> TYPE: DNA
<213> ORGANISM: Artificial
<220> FEATURE:
<223> OTHER INFORMATION: Synthetic

<400> SEQUENCE: 22

```
ggtccgattg agacttttca acaaagggta atatccggaa acctcctcgg attccattgc    60
ccagctatct gtcactttat tgtgaagata gtggaaaagg aaggtggctc ctacaaatgc   120
catcattgcg ataaaggaaa ggccatcgtt gaagatgcct ctgccgacag tggtcccaaa   180
gatggacccc cacccacgag gagcatcgtg gaaaaagaag acgttccaac cacgtcttca   240
aagcaagtgg attgatgtga tggtccgatt gagacttttc aacaaagggt aatatccgga   300
aacctcctcg gattccattg cccagctatc tgtcacttta ttgtgaagat agtggaaaag   360
gaaggtggct cctacaaatg ccatcattgc gataaaggaa aggccatcgt tgaagatgcc   420
tctgccgaca gtggtcccaa agatggaccc ccacccacga ggagcatcgt ggaaaaagaa   480
gacgttccaa ccacgtcttc aaagcaagtg gattgatgtg atatctccac tgacgtaagg   540
gatgacgcac aatcccacta tccttcgcaa gacccttcct ctatataagg aagttcattt   600
catttggaga ggacacgctg acaagctgac tctagcagat atcaaacaag tttgtacaaa   660
aaagcaggct ccgcggccgc ccccttcacc agatctccat ggcgcaagtt agcagaatct   720
gcaatggtgt gcagaaccca tctcttatct ccaatctctc gaaatccagt caacgcaaat   780
ctcccttatc ggtttctctg aagacgcagc agcatccacg agcttatccg atttcgtcgt   840
```

```
cgtggggatt gaagaagagt gggatgacgt taattggctc tgagcttcgt cctcttaagg    900
tcatgtcttc tgtttccacg gcgtgcatgg ctatcctaga ccttaagtcc ctcgtgctga    960
acgccattaa ctactggggc cctaagaaca acaacggcat ccagggcggt gacttcggct   1020
accccatctc tgagaagcag atcgacacta gcatcattac cttcacccac cctcgcttga   1080
tccccctacga tcttactatc ccgcagaacc ttgagaccat cttcaccaca acgcaggtgc   1140
tcaccaataa cactgacctc cagcaatccc agaccgtgag ctttgcgaag aagaccacta   1200
ccacgacctc aactagcacg accaacggtt ggacagaagg aggcaagatc agcgacacgc   1260
tggaggagaa agtttcggtt agcattccgt tcatcggtga gggtggcggg aagaactcga   1320
ctaccataga ggccaacttc gcacacaact ctagcaccac taccttccag caagcaagca   1380
ctgacattga gtggaacatt agccaaccgg tgctggttcc tccctctaaa caagttgtcg   1440
cgacccttgt gatcatggga ggcaacttta ccatccctat ggacttgatg accacgattg   1500
atagtacaga gcactactcc cactactccg gttaccctat cctcacctgg atctcgtccc   1560
cagataactc ttactccggt cccttatgt catggtactt tgcaaactgg cctaaccttc    1620
cgagtggatt cggcccactg aatagtgata acacggtcac atacactggc tctgtcgtgt   1680
cccaagtttc ggccggtgtc tacgctaccg tccggttcga tcagtatgac attcacaatc   1740
tccgtactat cgagaagact tggtatgctc gccatgcgac gctgcataat ggcaagaaga   1800
tttctatcaa caatgtcacg gaaatggctc caacatcccc tatcaagaca aatgagcaaa   1860
agttgatttc tgaggaggat tgtgaggat ccaattcccg atcgttcaaa catttggcaa    1920
taaagtttct taagattgaa tcctgttgcc ggtcttgcga tgattatcat ataatttctg   1980
ttgaattacg ttaagcatgt aataattaac atgtaatgca tgacgttatt tatgagatgg   2040
gttttatga ttagagtccc gcaattatac atttaatacg cgatagaaaa caaaatatag    2100
cgcgcaaact aggataaaat atcgcgcgcg gtgtcatcta tgttactaga tc            2152

<210> SEQ ID NO 23
<211> LENGTH: 2122
<212> TYPE: DNA
<213> ORGANISM: Artificial
<220> FEATURE:
<223> OTHER INFORMATION: Synthetic

<400> SEQUENCE: 23
ggtccgattg agacttttca acaaagggta atatccggaa acctcctcgg attccattgc     60
ccagctatct gtcactttat tgtgaagata gtggaaaagg aaggtggctc ctacaaatgc    120
catcattgcg ataaaggaaa ggccatcgtt gaagatgcct ctgccgacag tggtcccaaa    180
gatggacccc cacccacgag gagcatcgtg gaaaagaag acgttccaac cacgtcttca    240
aagcaagtgg attgatgtga tggtccgatt gagacttttc aacaaagggt aatatccgga    300
aacctcctcg gattccattg cccagctatc tgtcacttta ttgtgaagat agtggaaaag    360
gaaggtggct cctacaaatg ccatcattgc gataaaggaa aggccatcgt tgaagatgcc    420
tctgccgaca gtggtcccaa agatggaccc ccacccacga ggagcatcgt ggaaaagaa    480
gacgttccaa ccacgtcttc aaagcaagtg gattgatgtg atatctccac tgacgtaagg   540
gatgacgcac aatcccacta tccttcgcaa gacccttcct ctatataagg aagttcattt    600
catttggaga ggacacgctg acaagctgac tctagcagat atcaaacaag tttgtacaaa    660
aaagcaggct ccgcggccgc cccttcacc agatctccat ggcgcaagtt agcagaatct     720
gcaatggtgt gcagaaccca tctcttatct ccaatctctc gaaatccagt caacgcaaat    780
```

| | |
|---|---|
| ctcccttatc ggtttctctg aagacgcagc agcatccacg agcttatccg atttcgtcgt | 840 |
| cgtggggatt gaagaagagt gggatgacgt taattggctc tgagcttcgt cctcttaagg | 900 |
| tcatgtcttc tgtttccacg gcgtgcatgg ctatcctaga ccttaagtcc ctcgtgctga | 960 |
| acgccattaa ctactggggc cctaagaaca acaacggcat ccagggcggt gacttcggct | 1020 |
| accccatctc tgagaagcag atcgacacta gcatcattac cttcacccac cctcgcttga | 1080 |
| tccccctacga tcttactatc ccgcagaacc ttgagaccat cttcaccaca acgcaggtgc | 1140 |
| tcaccaataa cactgacctc cagcaatccc agaccgtgag ctttgcgaag aagaccacta | 1200 |
| ccacgacctc aactagcacg accaacggtt ggacagaagg aggcaagatc agcgacacgc | 1260 |
| tggaggagaa agtttcggtt agcattccgt tcatcggtga gggtggcggg aagaactcga | 1320 |
| ctaccataga ggccaacttc gcacacaact ctagcaccac taccttccag caagcaagca | 1380 |
| ctgacattga gtggaacatt agccaaccgg tgctggttcc tccctctaaa caagttgtcg | 1440 |
| cgacccttgt gatcatggga ggcaacttta ccatccctat ggacttgatg accacgattg | 1500 |
| atagtacaga gcactactcc cactactccg gttaccctat cctcacctgg atctcgtccc | 1560 |
| cagataactc ttactccggt cccttttatgt catggtactt tgcaaactgg cctaaccttc | 1620 |
| cgagtggatt cggcccactg aatagtgata acacggtcac atacactggc tctgtcgtgt | 1680 |
| cccaagtttc ggccggtgtc tacgctaccg tccggttcga tcagtatgac attcacaatc | 1740 |
| tccgtactat cgagaagact tggtatgctc gccatgcgac gctgcataat ggcaagaaga | 1800 |
| tttctatcaa caatgtcacg gaaatggctc caacatcccc tatcaagaca aattgaggat | 1860 |
| ccaattcccg atcgttcaaa catttggcaa taaagtttct taagattgaa tcctgttgcc | 1920 |
| ggtcttgcga tgattatcat ataatttctg ttgaattacg ttaagcatgt aataattaac | 1980 |
| atgtaatgca tgacgttatt tatgagatgg gttttttatga ttagagtccc gcaattatac | 2040 |
| atttaatacg cgatagaaaa caaaatatag cgcgcaaact aggataaatt atcgcgcgcg | 2100 |
| gtgtcatcta tgttactaga tc | 2122 |

<210> SEQ ID NO 24
<211> LENGTH: 1919
<212> TYPE: DNA
<213> ORGANISM: Lygus hesperus

<400> SEQUENCE: 24

| | |
|---|---|
| acacccccag ggtcccccatt gttgttcagc cgtttgaaag gagtcagcaa acagcgggct | 60 |
| ttcttcttag gagatttgcg tccgtcggac cggcacaccc ccagggtccc catttttgttc | 120 |
| agtgtttgaa aggagtcagc aaacagcggc aagatgtgtg acgacgatgt agcggcgctc | 180 |
| gtagtcgaca acggctcagg aatgtgcaag gcgggcttcg ccggagatga cgctcccagg | 240 |
| gctgtcttcc cctccatcgt cggccgcccc aggcatcagg gtgtgatggt cggtatgggt | 300 |
| caaaaggact cctacgtcgg cgacgaggct cagagcaaga gaggtatcct cactctgaag | 360 |
| taccccatcg agcacggcat catcaccaac tgggacgaca tggagaagat ctggcaccac | 420 |
| accttctaca acgagctccg cgtcgctccc gaggagcacc ccatcctcct cacggaggct | 480 |
| cccctcaacc caaagccaa cagggagaag atgactcaga tcatgtttga gaccttcaac | 540 |
| acccccgcca tgtacgtcgc catccaggcc gtcctttccc tctacgcttc cggtcgtacc | 600 |
| accggtatcg tcctcgactc cggagatggt gtctcccaca ccgtccccat ctatgaaggt | 660 |
| tacgcccttc ctcacgccat cctccgtctg gacttggctg gccgtgactt gactgactac | 720 |
| ctgatgaaga tcctcaccga gaggggttac tctttcacca ccaccgctga gagggaaatc | 780 |

```
gtccgcgaca tcaaggagaa gctctgctac gtcgctctgg acttcgagca ggaaatggcc      840
accgccgccg cctccacctc cctcgagaag tcctacgagc ttcccgacgg acaggtcatc      900
accatcggca acgagaggtt ccgttgcccc gaagccctct tccagccttc cttcctgggt      960
atggaatcct gcggtatcca cgagaccgtc tacaactcca tcatgaagtg cgacgtcgac     1020
atcaggaaag acctgtacgc caacaccgtc ctctccggag gcaccaccat gtaccccggt     1080
atcgccgaca ggatgcagaa ggaaatcacc gccctcgctc cctcgaccat caagatcaag     1140
atcatcgctc ccccagaaag gaagtactcc gtatggatcg gtggctccat cctcgcctcc     1200
ctctccacct tccaacagat gtggatctcc aagcaggagt acgacgagtc cggccccggc     1260
atcgtccacc gcaagtgctt ctaagcgaaa cactcaccac atcaatacac cactacatca     1320
aaccacacaa gacgcgccag ttacaatcgg gaccgtggtg ggcgcgtctt gttgtggttt     1380
gatgcccccc cccccccccc caccccccac ctaaaaatcc caggggctcc ctcgagaaag     1440
tcctacgagc tttcccgacg tcaccatcgc gaaaggtccc cccccctgtg gaattggcct     1500
cccccgtcga ctaccatcat gtctgccaac tatcgacacc ctcgacgtgg acaatatcat     1560
tactggcgtc ctctactctt acgctattgc gcccactatt ctagtccatt gctactccat     1620
taatagagat ctacttcatt gtccatacta tatacactac tattttttac atacttactg     1680
ctcacttatt attgagtttc aattttacat attcgtttaa tacattatgc agatcttatt     1740
ctccaactag tttcgcgtag tggcttttcg gggtgaaata ggtgcgtatt gctggacttg     1800
aggtgttgtc acgctatact gttttcttgc actattctat cggtaggtag gagtcagttt     1860
cggcattttt attgttcatg cctcattcat attcatgtta tttaaatcgt gataggtga      1919
```

`<210>` SEQ ID NO 25
`<211>` LENGTH: 991
`<212>` TYPE: DNA
`<213>` ORGANISM: Lygus hesperus

`<400>` SEQUENCE: 25

```
acaaacgctt tgcagtgagg aaggtggaag gaactgaaaa tatatcttga aggagtttaa       60
catcatacaa ggtgatttca tctcgtgtca acggtacctg catctatcgg tgagatgatt      120
tacttaattt tggctctggc cataatatgg gccttcgtga aactctacac gcaggtcttc      180
aattactggg agcaacgagg gtttccgtac gtggaaggga aattccctct tggcagtgac      240
ccctgcctct ctcgcccgtc caagttcttg ggtttcgaag ttcaggaaca ttacaggaaa      300
cttttcgggc accctctcgg cgggatatac gtcggcagga gaccagatct catcgtcagg      360
gaccccaaaa taatcaagaa catcatggtc aaagattttg ctcattttcg gaatcgcagt      420
gttgagatcc cttctaaaga caatccactg acacaacact tgttctcgct ggaaggcacg      480
aaatggagag ctctccgagt caagctcaca cctactttca cgtctggcaa gttgaaactg      540
atgtacagcc tattcgtaga atgcgctcaa cgcttggaac gcaaattaaa cgaagattct      600
atgaagaacg aaggggtggt ggatataaag gacaccatcg caaggtttac cactgacata      660
atcggctctt gcgcgttcgg cctagaaatc gacagtctca caaccccga cgagcccttc       720 aggaaaatcg gaatgcgttt attccgacgt aacctgaaag gaagactcat cgagttgatc      780
tacagtttgg caccgagcct acgaaactac ttgaaactat cgaggacatc caaagagacg      840
gaaaaaatgg tcatgtcggg tatcggccag actatcgaat atcgtgagaa aaacaacgtc      900
cgacgaaatg attttctcga tctcctcatc gagctgaaaa acagggacat tttgtacgtt      960
gatcgacaga aagacagcaa atattgaaaa c                                     991
```

<210> SEQ ID NO 26
<211> LENGTH: 2656
<212> TYPE: DNA
<213> ORGANISM: Lygus hesperus
<220> FEATURE:
<221> NAME/KEY: misc_feature
<222> LOCATION: (1)..(1)
<223> OTHER INFORMATION: n is a, c, g, or t

<400> SEQUENCE: 26

```
nccctttaa agcccccgca cccgaggtgt ttccgtgatc aatattattt catcctattt      60
catctccatt acattcccgt catgcacttg gagaaccact ttgagaccgt ttcttacttt    120
taactaatca accatgggaa aagagaagat tcatatcaac atcgtcgtca ttggacacgt    180
cgactccggc aaatccacga ccaccggaca cttgatctac aaatgcggtg gtatcgacaa    240
gcgtacgatc gagaaattcg agaaggaagc ccaggaaatg ggtaaaggtt ccttcaagta    300
cgcctgggtt ttggacaagc tgaaggccga gcgtgagcgt ggtatcacca tcgatatcgc    360
cctctggaag ttcgaaactg caaatacta cgtgaccatc atcgacgccc ctggacacag    420
ggatttcatc aagaacatga tcactggaac ctcacaggct gattgcgctg tgctgatcgt    480
agcagccggt accggtgagt cgaagctgg tatctccaag aacggacaaa cccgagaaca    540
cgcccttctc gccttcaccc tcggtgtgaa acagctcatc gttggtgtga acaagatgga    600
ctctactgag cccccctaca gcgagaaccg tttcgaggaa atcaaaaagg aagtctcgtc    660
ctacatcaag aagatcggtt acaacccagc ggccgtcgcc ttcgttccca tctccggatg    720
gcacggcgac aacatgttgg aaccctctga caagatgccc tggttcaagg ggtgggccgt    780
cgagaggaag gaaggcaagg ctgacggcaa gtgcctcatc gaagccctcg acgccatcct    840
ccccccctcc cgccctaccg acaaagccct caggcttccc ctccaggacg tgtacaagat    900
cggcggtatc ggaactgtcc ccgtgggtcg tgttgagacc ggtgtcctga acccggtat    960
ggtcgtcacc ttcgcccccg tcaacctgac cactgaagtc aagtccgtgg agatgcacca   1020
cgaagccctc caggaagccg tgcccggcga caacgtcggc ttcaacgtca gaacgtctc   1080
cgtcaaggaa ttgcgtcgag ggtacgtcgc cggagactcc aaggcttctc ctcccaaggc   1140
cgcttccgac ttcaccgcac aggttattgt cctgaaccat cctggacaga tcgccaatgg   1200
ctacacccca gtgttggatt gccacactgc tcacatcgca tgcaaattcc aagacatcaa   1260
ggagaaatgc gaccgtcgta ctggtaaaac caccgaacag aaccccaaat ccatcaagtc   1320
cggtgacgct gccatcatca ccctcgtccc gaccaagccc atgtgcgtcg agtccttcca   1380
ggagttcccc cctcttggac gtttcgctgt gcgtgacatg agacagaccg tcgctgtcgg   1440
tgtcatcaag agcgtcacta caaggacat caccaccggc aaagtaacga aggccgcaga   1500
gaaggcccag aagaagaaat aactaggtgt catggaatca catacactca tcaaggggaa   1560
ccttggtcgc tattctgtac tctgcccact cctcttgtcc aagtggttgc tccaaccgtg   1620
tttccatcgc aaagagttca gaaggaaaag cggttaaagt caccacttaa ctataatccc   1680
aactttatta tatatatata aatatatagc ctcgacttgt gtacacgttt ttaattaaag   1740
aaggagactg tttattattt ttggttttgt ttttatcatt taaaaaatct atttcttttt   1800
tcgaaaaaaa gaaaacgaac ttgggtttt ttttgtatt ttacatctgg tggtataact   1860
gtgccccttt gtcctgtttt gtgtgaaaaa tagcgaattc tgttttttaa tttattttt   1920
tgcgatttta ttcttcgtca aaataatttt aaaaaaattt atttacagca ttttttaaat   1980
taattgaagc aaaaactata attgacattc tgtatagatt ggtgactaaa taaactcgaa   2040
```

```
tgcttcatga aaaaaaaaa aaagggcgg ccaaaaaaaa aaaaaaaaaa aaaaaaaaaa    2100
aaaaaaaaaa aaaaaaaaaa aaaaaaaaaa aaaaaaaaaa aaaaaaaaaa aaaaaaaaaa   2160
aaaaaaaaaa gggggggcc cctttaaaaa tcccccgggg gggcccaatt ttcccggacc   2220
cccttttttt tgaaaaaggg ggcccctaaa ggggggctat ttaaaagtag ggccggggcc   2280
gcgttttttaa accgcggggg ggggaaaaat ggttatttgg gatttttggg aaagaaccct   2340
tttttttggg ggggaaata ttgggaaaaa tcccccaaaa aatttaaagg tttaagggaa   2400
aaaaaaaatt tttaagggga aaaggggggta aaaaaacttg ctttttttg tggttgaaaa   2460
ttttttttt tgggttttttt tttttaaaaa ttttttcccc gggggttggg gttttttattg   2520
gttggggttt ttaaaattcc aagccccagg gttttttgg ggccccccac cccccaagt   2580
ttgttttgat ttaaaatccc ccaacccaat tttggaaggg gtttttttg tttaaaaaac   2640
cccccccccc ccccc                                                   2656

<210> SEQ ID NO 27
<211> LENGTH: 1043
<212> TYPE: DNA
<213> ORGANISM: Lygus hesperus

<400> SEQUENCE: 27
gtcctctcgt cttgtttcca gaggaggtgt gaatttagg atgaaatctt tgctggtgct     60
tatgtcagtg gtgggcttgg ccatgtgcca gtggggccag cctggacttc ctcaggacac    120
tcctgaagta gccgctgcca agctgccca ctacgccgct ctcgccagag ccggtacccc    180
agttcacaac gccgctccca cctggaacgc cgccctgcc tggggaactc ccgccgcccc    240
cggcgtccct caagatacgc ctgaagtcgc cgctgccaag gccgctcatt tcgctgccgt    300
cgctcaggtt cagagccaca cgcctcagca gtcttgggct cctcagcagt cctggactcc    360
ccagagccag cagtggacta gcgagcacca acccaggtgg aacggaccca tcgctctgcc    420
cccgggcttc gaccagaacg cgctccct ccccgtccaa gacacccctg aagtagctgc    480
tgagcgcgca aggcacttca acctctactc cagcggtgga catccttccc tcgccccgc    540
tcagccttcc tggaacgccg ctcctcaatg gaacgccgct cctcagtggt ccgctcccgc    600
tacccagtgg aacgctcaac ccggtctccc tcaggacacc cccgaagtcg ccgctgccaa    660
ggccgctcac ttcgccgctc acgctcaact tgctcctgcc tccaaccacg gtaggtggaa    720
gagaggaatc ctcgctgccc cagtcaccac cgtcagcgct cactccacct ccatcgtcca    780
ctctgcccc gtggtccacg ccacccccgt cgtccacgca actcccattg ttcgcgctgc    840
tcccgtagtc cacaccttgc cctaccttcg caccctggtc cacaccgccc ccatcgtccc    900
caccgccccc atcgtcccca cccgcccctc tccgcccatc gctccactgg gtaattaatg    960
actggcgaag aagccacgac tgatttttg tgtcgtagtt tacgagcttt gtagaaaaac   1020
gaaaatttga atgaattgat tgg                                         1043

<210> SEQ ID NO 28
<211> LENGTH: 2346
<212> TYPE: DNA
<213> ORGANISM: Lygus hesperus

<400> SEQUENCE: 28
actcgttcta gatcgcgatg gacgcgtggt cgagaaacga gaacgagcta cgttgagcat     60
caagagcttt cgtactattg aaattctcga aaaatcgcag atcttcgtta aaactttcga    120
ctcgggaaga ccatcaccct cgaggtcgag ccttctcgat accattgaaa acgtgaaggc    180
```

```
gaaaattcag gataaagaag gcatcccccc agatcagcag aggttgatct ttgccggcaa      240
gcagttggaa gacggacgta ctttgtctga ctacaacatc caaaaagaat ccactctcca      300
cctggtcttg agattgagag gtggcatgca gatcttcgtg aagaccctca caggaaagac      360
catcactctt gaggtcgagc cttctgactc catcgaaaac gtcaaggcta aaattcaaga      420
caaggaaggt attcctccag atcagcagag attgatcttc gccggcaaac aactcgaaga      480
tggccgtacc ctctctgact acaatattca aaaagagtcc acccttcact tggtgttgag      540
attgcgtgga ggtatgcaaa tctttgtcaa aacattgact ggaaagacca tcacccttga      600
agtcgaaccc tccgacacca tcgaaaatgt caaggccaag atccaggaca aggaaggcat      660 cccccccagat cagcagaggt tgattttcgc tggcaaacaa cttgaagacg gacgtaccct      720
ctcggactac aacatccaga aggagtcgac cctccatctt gtcctccgtc tgcgtggtgg      780
tatgcagatt tttgtcaaaa ctctgactgg caagacaatc acccttgaag tagagccctc      840
tgacaccatc gaaaatgtca aggcgaaaat ccaggacaaa gaaggcatcc cccagatca      900 gcagaggttg atcttcgccg gtaagcagct gaagacggc cgtaccctct cggactacaa      960
catccagaag gagtccaccc ttcatcttgt cctccgtctg cgtggtggta tgcagatttt     1020
cgtgaagacc ttgactggca agaccatcac tcttgaggtc gagccctctg acaccatcga     1080
aaacgtcaag gccaagatcc aggacaagga aggtatcccc ccagatcagc agaggttgat     1140
cttcgctggc aagcagctcg aggatggtcg taccctctcg gactacaaca tccagaagga     1200 gtccacccctt catcttgtcc tccgtctgcg tggtggtatg cagattttcg tgaagacctt     1260
gactggcaag accatcactc ttgaggtcga gccctctgac accattgaaa acgtcaaggc     1320
caagatccag gacaaggaag gtatcccccc agatcagcag aggttgatct cgccggtaa     1380 gcagcttgaa gacggccgta ctctctctga ttacaacatc cagaaggagt cgaccctcca     1440
ccttgtcctc cgtctgcgtg gtggtatgca gattttcgtg aagaccttga ctggcaagac     1500
catcactctt gaggtcgagc cctgacac cattgaaaac gtcaaggcca agatccagga     1560
taaggaaggc atcccccag atcagcagag gttgatcttc gccggtaagc agcttgagga     1620
tggacgtacc ctgtcagact acaacatcca aaaggagtcc accctgcact tggtgttgag     1680
attgcgtggt ggtatgcaga tcttcgtcaa gaccttgact ggcaagacga tcactttgga     1740
agtcgagccc tctgacacca ttgagaatgt caaagccaaa atccaagata aggaaggcat     1800 cccccccagat cagcagaggt tgatcttcgc tggtaagcag cttgaagacg ccgcactct     1860 ttcggattac aacatccaga aggagtcgac cctccaccct gtccttcgtc tgcgtggtgg     1920
tatgcagatc ttcgtcaaga cgttgacagg caagaccatc acccttgaag tcgagccctc     1980
tgacaccatc gaaaacgtca aggctaagat ccaggacaag gaaggtatcc ccccagatca     2040
gcaaagattg atcttcgccg gcaaacagct cgaagatggc cgtaccctct cagactacaa     2100
cattcaaaag gagtcaactc ttcatctcgt tctgaggctc cgtggcggtc gttattgatc     2160
acaattccaa acttaaaaat tgcgttccga ttttccttct ttatttggcg aaaaatacgt     2220
accctagtta attaaaatga cttgaaattt gatttttaa gaatgcttcg aatttttta     2280 tagatggttt gttacgtaga cgaatacaca acagtgaaag ccgaaaaaaa aaaaaaaagg     2340
gcggcc                                                                2346
```

<210> SEQ ID NO 29
<211> LENGTH: 1151
<212> TYPE: DNA
<213> ORGANISM: Lygus hesperus

<400> SEQUENCE: 29

```
gctcttctcg ggaatcttcg aattcttcat agcaaatctc ttcgaattca tattcgggta      60
acgctcagcc ataaaagaat agtcctcgaa caaagcagta ataagttcaa ttcaggggaa     120
tttaatcttc gtaagcctag ccagggaatg aaccttcggg aaacttcaac aagaatttta     180
acataccagg gaaccaggt cattcgaagt ttcttcagag aacgtagttc acttttcag       240
gagtaattca agaaataggg gatatcaagt ttggtctggt cagaatttga gatggggaga     300
aatattcagc agttgaaaag gaaacctcgg aaacctattg gacgtcgagg gacatcgttg     360
gtgggacggc aaaggaggta atggtggaag aaaaaaacca cgttttatgc aagtgacttt     420
ggatgattcc attgtggtgg gactcaacat caagaatact ccaaaagact gcttcatcgt     480
gaattcaagt cataatcttc gtgtcgatcg aattaatatt gacatcaaag atggggataa     540
gaagggaggg cacaacacag acgggtttgg cgtaagtgga tcgagaaatg tcacagtttc     600
aaactgccag gtccacaacc aagacgactg cttcgccacg acatctggaa gtgacacgat     660
attcgagaac agcaagtgca cgggtggtca tggcatatct gtaggatcca tgggagctgg     720
aaaagtcgtt gaaagactga cagtgaggaa ctgtaggatt ttggcgaaca gcaatggcat     780
tcgaatcaag acccgacgag gagaaacggg tgcagtccgc gatattacgt ttgaaaatat     840
agagctgaaa gacataaggc agtatggtat tgtcattcaa ggcaattatt acaacagtgg     900
accgaaggga gaccccactc cttttcccat tcataacctg gttgtcaaca acgtgcacgg     960
tactgtgagc cgtaaaggaa ccaacatcct gatctgggtg gatcctggaa gcgtcagcaa    1020
ttggaaatgg aactcaaatg tgtccggagg tcagaaggaa cttggttgta aggagttcc    1080
aagtggactg aacattcgtt gtggcgagaa ataaggtgtt tacgaccact tcatgtaaca    1140
cccaattaat g                                                          1151
```

<210> SEQ ID NO 30
<211> LENGTH: 823
<212> TYPE: DNA
<213> ORGANISM: Lygus hesperus
<220> FEATURE:
<221> NAME/KEY: misc_feature
<222> LOCATION: (729)..(729)
<223> OTHER INFORMATION: n is a, c, g, or t

<400> SEQUENCE: 30

```
ctcaaaactc aaaggttctc tcaggtatat ctttcagctt cctattcgga ttcaagacta      60
ttcattaata taagacttaa ggagtacaat aataataaat tcacgattaa ggacaaacga     120
tccttaatta atgatcctcc ttaattaata cctaacgcac tacccttttt atcacgtcag     180
gcaataaaaa gttctacacc ttatcaaaaa tcaacaaatt cctcaaaggt accttaggta     240
tgtatcattt acgtaacaat attacaatgc agaatttgca gccactacag aagggaatcg     300
caacaactat taagatttca caaggtagac taaacttact tagttacgcc gatttgatag     360
atgtagaatt atacttagtt attgccgaaa ataaattttt cttcgttaaa aaccaaata     420
aaaggtaaca ataaacgtgg gtagagaact aaatcacgaa acgtatattt tagtgattgg     480
ataataaaga aaattttgaa gtttaaacgt tgcacattta tcacacatct cccaaaatta     540
tgggagcatc aaattcaatt catacagatt tggtcagtag gtacctaaat gaaattatcg     600
aggcatcatc ctacttgagt gggcatcgaa acatacata atataataag atgctaacat     660
ctacagcaga aataaatacc tatattattt ttaaattatg gacaagaaag aaaggtactt     720
tcaactatng agagtagttt gataacatga gaaatattag taattaatca cgaatgggaa     780
```

-continued tttaaaggat tgagatttgg ttacgtacaa tattgtagct ctt    823

<210> SEQ ID NO 31
<211> LENGTH: 759
<212> TYPE: DNA
<213> ORGANISM: Lygus hesperus
<220> FEATURE:
<221> NAME/KEY: misc_feature
<222> LOCATION: (1)..(56)
<223> OTHER INFORMATION: n is a, c, g, or t
<220> FEATURE:
<221> NAME/KEY: misc_feature
<222> LOCATION: (127)..(149)
<223> OTHER INFORMATION: n is a, c, g, or t
<220> FEATURE:
<221> NAME/KEY: misc_feature
<222> LOCATION: (286)..(305)
<223> OTHER INFORMATION: n is a, c, g, or t
<220> FEATURE:
<221> NAME/KEY: misc_feature
<222> LOCATION: (457)..(478)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t

<400> SEQUENCE: 31
nnnnnnnnnn nnnnnnnnnn nnnnnnnnnn nnnnnnnnnn nnnnnnnnnn nnnnnntttc    60
aaaagtttaa cattttaaac gcaaccacgc cccccaccc ccccaccgac cctcacatcc    120
cccccnnnnn nnnnnnnnnn nnnnnnnnng tgcgctctgg tggcttcgag ggtttcttct    180
tttttaaatt tactaagaac aatcaaactt cgattttct attacccta cttcctttct    240
tctgatttgg gggttaaagt tttagaatga ttccggaaaaa tggaannnnn nnnnnnnnnn    300
nnnnntataa ttaaggacaa aatgatttac agatttagcg attaaaagaa atagagtaat    360
cgttttgata taattcttta tgttttatc ttttttattc ttggggtttt tgagtgggat    420
tttggttttt tgtttaaaat tttgaaaaag gggaatnnnn nnnnnnnnnn nnnnnnnntt    480
tgggggaatat actgacaact tgtcacccga tgttaaagga ttttaacact tttcggtttt    540
cttttgttct ttgggttatt taatttttt cgaatttatt caaaaattta aaattaatca    600
aattttcgng ggttattggt tttttaacca tttaagtttt ttatacccctt tacgttttta    660
ccaatggcgt aacacctgta taaatggttg aaaatgttat attgtttttt tctgttcatc    720
ctttcaccat ttcatcattt cataaaacgg gaaagggat                         759

<210> SEQ ID NO 32
<211> LENGTH: 903
<212> TYPE: DNA
<213> ORGANISM: Lygus hesperus
<220> FEATURE:
<221> NAME/KEY: misc_feature
<222> LOCATION: (246)..(277)
<223> OTHER INFORMATION: n is a, c, g, or t
<220> FEATURE:
<221> NAME/KEY: misc_feature
<222> LOCATION: (435)..(450)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t

<400> SEQUENCE: 32
cgacggcggg ccggcccctt ctttctttcc ttcttccgg gttaaaacct tctccttttc    60
cacttcaaaa cacaacacaa taacactccc ctacaagtta aaatggccct catcaacaag    120

```
tctagccgta aaaaatcaag tatggccact taacaaccac taatttcgac aactcggcat      180
ctaagttact tcgataaaag aaaatcaact acctactccg taacaatcag atcaaaccta      240
atcacnnnnn nnnnnnnnnn nnnnnnnnnn nnnnnnncaa taataattta ctcgtgtaat      300
ttcaaacgtt ttcaagcttc gagtacgatc gaaccttcgt tctgcgaaat aacagttagg      360
gagttgctcg aataccaacg gggatttcgt ttgagaggtc ggaagcacac gcttgctctt      420
gagcagagtg accannnnnn nnnnnnnnnn aagcaagcca aacctcatac ctatacagtt      480
cctcggccct tcgccgaacg gaaggaaggt aaagggcgtg atggaggact tcttggtgtc      540
tgagaacctg tctgggtcga acctctcagg gtcgggaaag tactgggggt cgtggtgcag      600
tgagtagacc gggatgagca cacgtattcc ctcctcgatt acgtatttgg tccccggaac      660
agcngtaagg ttttgtgcac acccgagtga gtgtgtggag agtcgggtac ttcctgatcg      720
tttcatttat gacctgatcg agataaggca tttcgtgtaa ggcttggtag ttgagaccgc      780
cgaatttact ggtgacttct tcaatttctc tacggacttt atcttgaatc acttgatggt      840
atgccaattc gtagagggcg taactctgta ctgaatgatg acgtctcgaa aacggcaatg      900
aaa                                                                   903

<210> SEQ ID NO 33
<211> LENGTH: 890
<212> TYPE: DNA
<213> ORGANISM: Lygus hesperus
<220> FEATURE:
<221> NAME/KEY: misc_feature
<222> LOCATION: (3)..(29)
<223> OTHER INFORMATION: n is a, c, g, or t

<400> SEQUENCE: 33
cgnnnnnnnn nnnnnnnnnn nnnnnnnnnt tccagctttc gagttctttc cgtcacccca       60
ggtttccccg cacctccgtc cacggttccc ctccgggttc ggtttcctcc ggtgtcgcgg      120
acgaaggagt accggcctct tttcgttttcc gggacaggag gtttctcagt agtgtcagcc      180
gcaggcttcc gtcgaggttc gagcttcaga ggcctccgcc ggcttttcag caggcttttc      240
tgtttcgtcg gtggttgatt tggtggcttc accttcagac gtcgaaggtt ttgcgtcatc      300
gggtttggtt gtcagatctt ccactttggg tttgtcctct tgttgtcac tatcctcaac      360 ctgagtaggt ttgtcggtgg gcgttggagc gggactgggg gcagcactgg tcgcagggggt      420 gccactactg ctagctgctt ccccaacact cccggcaggt ttcagctcgc caagttcctg      480 ccgcttttttg aggatttcgg gcatagaata atatccgttg atatgctcga attcttggac      540
cttcttcctg atgagtgaca tgacgcctat cctcgtaagg acgtgttgtc gagacaaacc      600
ttcgcgagga actccgtcag caaaggtctc tgcgttgtca gcacccggct cgcaaaggtg      660
ccgcataaag agggaaacgt aggctttgaa atgttttttcg gactttcctc gaaggtctcg      720
aaccaaccac tgcgaattga acgcatcttg gggaggcatt ccataccgca tgatcgcatt      780
gaggaaggcc tttctttgcc tggcgttgaa accaaggact tcgatgtttc caccaactct      840
agcgagaagt ggtggcagag gccggtcttt ctcttctcgt ctttcgggtc                 890

<210> SEQ ID NO 34
<211> LENGTH: 763
<212> TYPE: DNA
<213> ORGANISM: Lygus hesperus
<220> FEATURE:
<221> NAME/KEY: misc_feature
<222> LOCATION: (22)..(52)
<223> OTHER INFORMATION: n is a, c, g, or t
```

```
<220> FEATURE:
<221> NAME/KEY: misc_feature
<222> LOCATION: (142)..(166)
<223> OTHER INFORMATION: n is a, c, g, or t

<400> SEQUENCE: 34
cctcccgaac ccgcctaaaa annnnnnnnn nnnnnnnnnn nnnnnnnnnn nnaacgcaaa      60
tatactacta gtacggactc ggtctggtaa acgctcgggg taccgggcag ctcacatgaa     120
attcgccagt aacgtataca annnnnnnnn nnnnnnnnnn nnnnnngaaa tcaggaacga     180
gtatgttaac gggattcttc ttattttcta tggtcggttt catggcagca tcgactcatg     240
cagaaacccg taggctgagt ggatgcatcc tgtccagtgc tcggcattct tgtggtaccc     300
ttcgggcgtg tttcatctcc ctggtgctcc attgcgttcc tgcttgtttt tatttatgat     360
gttggtcatt gctctcctaa tccagttttg tacgatggga gttttcatca cgtggatggt     420
tgtcaattgg tggcaattgc tgatatcgcc aatggagatg tttatcctcg gcgactgcat     480
agtgtactag ctttgatgat tctcctgctt atttcagggc actatgtaca tgttccacat     540
actgaattga tattcggaga gatccctgta cctgctgtta ctgatattat tcgacggaat     600
tgccatatca tgaaggcttt ggaaatctga cttctagcaa ccaattctct aaatgataag     660
ctactaacat gtggattgtg tgtagagtca tctgtgtcga caacatgctt gatgtctgca     720
tcaagattgt cgttatcatt ctctctcact ccactctcat cat                       763

<210> SEQ ID NO 35
<211> LENGTH: 1929
<212> TYPE: DNA
<213> ORGANISM: Lygus hesperus
<220> FEATURE:
<221> NAME/KEY: misc_feature
<222> LOCATION: (1920)..(1920)
<223> OTHER INFORMATION: n is a, c, g, or t

<400> SEQUENCE: 35
cagaggtcgt atcgtggcaa cgcaatatct gctgaacgcg gaagctgtct aaattttcg       60 taaggatcat gcgggtaggg ccccttgagc gcccatacga attctatcat gaatcgacag     120
tattaatggc cggtgtgaaa acttaacgct tccggagctt cttgaactgg tagaggaacc     180
gaggtctgcc ttgcgtgaca acaggtcccg gcatctcaag cttcttctta ttgaattatc     240
tccaaccaac tctcaaaatg cgtgagtgca tcagcgtaca cgtcggccag gccggagttc     300
agatcggtaa tgcctgctgg gagctctact gcttggaaca tggaattcag cctgatggac     360
acatgccgtc agacaagacc gttggaagcg gtgatgactc cttcaacacg ttttctctg     420 agactggagc tgggaagcac gttccccgtg ctgtctttgt tgatcttgag cccactgtcg     480
tcgacgaagt taggactgga acttacagac agctcttcca ccccgagcaa ctcatcactg     540
gtaaggaaga tgctgccaac aactacgccc gaggtcacta cacgatcggt aaggagatcg     600
tagacgtggt gctggatagg atccgcaagc tgtctgatca gtgtaccgga ctccagggct     660
ttttgatttt ccactccttc ggcggcggca ctggctctgg atttacctcc cttcttatgg     720
aacgcctttc ggttgactac ggcaagaaat ccaagctcga attcgctgtc taccctgctc     780
ctcaggtctc taccgctgtt gttgaaccct acaactccat cctcactacg cacactaccc     840
tcgagcactc cgactcgcca ttcatggtcg acaatgagcg tatttatgac atctgccgcc     900
gtaacctgga tattgagagg ccgacctaca ccaacctcaa caggctgatt ggtcagatcg     960
tttcctcaat aacagcctct cttcggttcg atggagccct taatgtcgac ctcacggagt    1020
tccagacgaa cttggtcccc taccccagaa tccacttccc cctcgtaacc tacgcccctg    1080
```

| | |
|---|---|
| tcatctcggc cgagaaagcc taccacgaac agctctctgt cggtgagatc accaacgctt | 1140 |
| gcttcgagcc cgccaaccag atggtgaaat gcgacccgcg ccacggcaag tacatggcct | 1200 |
| gctgcatgtt gtacaggggt gatgttgtac ccaaagacgt caacgccgcc atcgccacca | 1260 |
| tcaagaccaa gaggtccatc cagttcgtcg actggtgtcc cactggtttc aaggtcggca | 1320 |
| tcaactacca gccccccacc gtcgttcctg gaggtgactt ggccaaagtc cagcgagccg | 1380 |
| tctgcatgtt gtccaacacg accgccatcg ccgaggcctg ggctcgcctc gatcacaagt | 1440 |
| tcgacttgat gtacgccaag cgagcctttg tccactggta cgtcggcgag gcatggagg | 1500 |
| aaggagaatt ctctgaagcc cgagaggatt tggctgccct tgagaaagac tacgaagagg | 1560 |
| ttggaatgga ctccgtcgaa ggagatggcg aaggagctga agaatactaa atctacggt | 1620 |
| gtattatatt ttatatgtat tattattcaa aacacgtttc tgtgctatat tacttgtacc | 1680 |
| tacgagaatt tcatacaata atgtttgtta atttcgcttt ataaattatt acagttttct | 1740 |
| acagatcaaa aaaaaaaaaa aagggcgcc acgcgtccgc ccacgcgtcc ggacccacgc | 1800 |
| gtccggcaca actgagtact cattctcacg ccaaagtacg tgactaccat cgcgaaagct | 1860 |
| ttttttttac ttacctgaag gttttttcc actatttatt ttaaagcaga tttaattaan | 1920 |
| tggcgtaat | 1929 |

<210> SEQ ID NO 36
<211> LENGTH: 3641
<212> TYPE: DNA
<213> ORGANISM: Lygus hesperus

<400> SEQUENCE: 36

| | |
|---|---|
| cccccccccc ccccacccca aacataaaaa aaaaaaaatt ttcttttggg tgttgggggg | 60 |
| gtttgtgggg cccccccccc cccccccccc caaaaaaaaa accggagaga aaaaaaaaaa | 120 |
| aaaccttttt tttttgtgag aaaaaattgg ggggggtgtt ttttttttt ttttttttt | 180 |
| cccccccctt aaaaaaggc gcaaaaaaaa aaaataatt acaccccccac aaactccctt | 240 |
| tttttttctt tttttttttt gttttggggg gggggggggg ggggggtttt ttttttaaaa | 300 |
| aaaaaaaac cccccccaa aaatgggggg tggtgtttta ttttttacaaa aacaccccctt | 360 |
| gggggggggg ggggggcccaa aaaaaacccc cggggggtttt tttttaaaaa aacccaccac | 420 |
| aaaaaaaaaa cccccccccc cccgggtaat tttttttta aaaaaccccc cggaaaaaaa | 480 |
| aatctccccc cccccaaaaa aaccgggggtt ttccccccccc cccccccaa aaaaattttt | 540 |
| tttctcccca ggccctaaat tttctggggg ggggtttccc aaaaaccccc cccccaaaa | 600 |
| aaagtgttt tccaaaaaaa acccaaaaaa aattttttcc cccccccgt ttttaaaaac | 660 |
| cccccccccc cccctttttt aaaaaccccc ccctttgggg cccccttttt aaaaaaaaaa | 720 |
| gggggcccca aaaattggcc ccccccgggg aaattttaaaa accccccccc ccctttttt | 780 |
| tttttttttt tttttttttt ttttttttt tttttttttt tttttttttt tttttttttt | 840 |
| tttttttttt tttttttttt tttttttttt tttttttttt tttttttttt tttttttttt | 900 |
| tttttttttt tttttttttt tttttttttt tttttttttt tttttttttt tttttttttt | 960 |
| ttttcggtag taaatgttga gtgtaatctc aacaacaat ataaatatat aaaatcaagt | 1020 |
| gcgtaatata taaacaatgt tctgccagaa aagagaaaaa attgggaagg cgaaggagcg | 1080 |
| agatcgggag tccaaaatat aagttgcaac aaaaacgaag aaagaataca cgtaaaaaaa | 1140 |
| ttactaaacc gggtttaaat taacaaagct caaggaatgt tcgatcgcta agctccagtt | 1200 |
| tatgttgcag gggtacaaat agagggaggg aactgccagc tggggatatc gtgtacaaaa | 1260 |

```
caaatataga aaaaacactg cgctctcgag gcgcagaatc accaggctgg ccacacgtct   1320
agtgtgaggg aatgaattcg acttttttt tttggttgag gggggacatt tttgttttgt    1380
gtcgggaatg gggggggggg ggggggggat ttagttttcg tcgatctctt gttcttgctc   1440
ctcgtcgaat tcggcgtcct cgtcggcggt ggcctcctgg tactgctggt actcggacac   1500
caagtcgttc atgttggact cggcttcagt gaattccatc tcgtccatgc cctcgccggt   1560
gtaccaatgc aagaaagcct ttctcctgaa catggcagtg aattgctcgg agattctctt   1620
gaagagctcc tggatggcag tggagttgcc gatgaaggtg gcggacattt tgagtcctct   1680
gggggaatg tcgcacacgg ctgtcttcac gttgttgggg atccattcca cgaagtacga    1740
ggagttcttg ttttggatgt tgagcatctg ctcgtccact tccttcatcg acattcgccc   1800
tctgaaaatg gcggcgacag tgaggtatcg tccgtgtctg gggtcgcaag cggccatcat   1860
gttcttggcg tcgaacatct gctgggtcag ttcggggacg gacagagcgc ggtactgctg   1920
ggacccgcgt gacgtcagag gagcgaatcc tggcatgaag aagtggagtc gcgggaaggg   1980
aaccatgttg acggcgagtt tcctcagatc cgcgttgagc tgacctggga atcggaagca   2040
ggtggtgacg ccggacatgg tgaggctcac gaggtggttg aggtcgccgt aagtcggggt   2100
cgacagcttc aacgtcctga agcagatgtc gtagagggct tcgttatcta tgcagtaggt   2160
ctcgtccgtg ttttcgacga gttgatgtac cgagagtgtg gcgttgtagg gctccactac   2220
agtgtcggac accttgggag atggtacgac cgagtaagtg ttcatgattc tatcggggta   2280
ttcttctcgg attttgaga tcaataacgt tcccatgcca gatccagttc cacctccaag    2340
agagtgagtc aattgaaatc cctgtaagca atcacagcct tcggcctctt tcctgacgac   2400
atccaaaacg gcatcaacga gttcagcgcc ctccgtgtag tgacctttgg cccagttgtt   2460
tcccgctcca gactgtccga aaacgaagtt gtccggtctg aagagctgac caaagggtcc   2520
tgagcggact gagtccatgg ttccgggttc caagtcaacg aggatggctc tcggtacata   2580
ttttccaccg gatgcttcat tgtaataaac gttgatccgt tcaagctgga ggtcggagtc   2640
gccgtggtag gaaccggtgg ggtcgatgcc gtgttcgtcg gaaatgattt cccagaactt   2700
ggctccgatc tggttgccgc actggccggc ctgaatgtgt acgatttccc tcatttcgtg   2760
cgactgcgaa gaaaatgaa aaacgagag ctgaaaaatt cgactgaaac gaagcaacgg     2820
cttctgacaa ccactgccag acccagtaaa gtaaacaaag ctactgttgc tgctgcagta   2880
gttgccacca gaaacgatgc tgttgctgcc gtcagttctg ccaagcaaac cgtggctgct   2940
gaagcttccg ctgcatcttc taaagtcaac gccaaggtta cctctgccaa aaataacgta   3000
gcctctgctg tttcctctgc caaggacaag gtttccgctg atgtctctca agctaaagag   3060
aaggcttcag ccaccactgc caaaatcgaa gagaagaaga acgccgctaa agagaaggct   3120
tcagaaatcg ctgccaaaat cgaagagaag accagctctg ccgtcgcagc cgctaaagaa   3180
aatatcagca aagctaaagc caccgccgcc aacaagcttg agtccgctaa agagacagct   3240
caagagtata tcaaagaagc aaaagctaaa gctgaagctt tgaaggagaa aatcgctgcc   3300
aacgaaaacg tccaaaaagt ccaagagaaa gtggacgcta tgaagagcta cgtgagccag   3360
gccgtcaacc agaaactgga tgcgcaccct caaatcaaag cacagatcca gaaagctgac   3420
cagaaattgt ctgcacttac cgacaccatc aagagccaaa tgaatgaaaa ggtcccagcc   3480
ctgaaggaga agctcgaatc actcagtgcc agcttcaaac aatccttcga caagaacata   3540
gaaaaggcga aggagatgtt cgcctcctcg taattccatt tacaagggcc acacatgctc   3600
gaaaaatcga gtatccgatg tatataattc aataaaacta c                      3641
```

<210> SEQ ID NO 37
<211> LENGTH: 1760
<212> TYPE: DNA
<213> ORGANISM: Lygus hesperus

<400> SEQUENCE: 37

| | | | | | |
|---|---|---|---|---|---|
| ggccggaaag | tggggaaaaa | agccgttcgg | gaaaatcccc | tgaaacctgg | ccagaagtgg | 60 |
| aacccagctg | gggaatggcc | tgctgatcat | ggcgggtttg | gatgtgatgt | tagttgggtg | 120 |
| tggaggggtg | aggaggaacc | ccctagcctc | gagagaatgg | atctctcaga | catttggagg | 180 |
| cgctgggcga | ctggggggat | cctcgctaac | gtcgctggca | atcgcgacac | gtccgacttc | 240 |
| atatcagaca | gcagctcctc | cagctgttca | gtacctgtgg | aggacagcat | tggcgggctt | 300 |
| gttgccagcc | aaactctcct | tgctcaggtg | ctgatgggac | tcggccagac | attcgacctc | 360 |
| cgcgaacctc | gcgttgaggg | acatggcagg | atggttggga | tcctgcgtca | ggttcaggta | 420 |
| agcagctctc | ctcagttgct | cttcgatgac | caacgcctgc | tccaaaagct | tgaacctcct | 480 |
| ggcaaggaat | tgttcttga | tttcgaggaa | gtttcctttg | ccaacgtcca | ttttgaatgg | 540 |
| ttcgttgatg | atcgcgaaac | ggatgtcgtt | ctgaatgtct | tgccagcggc | cgtaaccgtg | 600 |
| cgtaacaata | cctccgagca | gccagtaatc | atgcctcctg | tgccagatct | cgtactctcg | 660 |
| accgggtacc | gcagccttct | cttcattctg | ccacagagtg | tggagttctg | taaagcctcc | 720 |
| gtcggcgatg | ttgaacatga | acttcctctt | ggatttgtct | tcttcgaagt | caggaagctt | 780 |
| gactttctcc | tcgtcctccg | tcttctcgtc | cttttcttct | tgacgacgg | attcttcttt | 840 |
| ttctcgctcg | tcacccccctt | ttttttttt | tttcgtttca | gctttaggtt | cttccgtcac | 900 |
| ctcaggtttc | tccgcatcta | cgtccatagg | ttcctctttg | gtttggttt | cttccggtgt | 960 |
| tgtggacgaa | ggagtatcgg | cttctttcgt | ttctgggaca | ggtggtttct | cagtagtgtc | 1020 |
| agctgcaggc | tccgttgagg | tttgagcttc | agaggcctct | gccggctttt | cagcaggctt | 1080 |
| ttctgtttcg | tcggtggttg | atttggtggc | ttcaccttca | gacgtcgaag | gttttgcgtc | 1140 |
| atcgggtttg | gttgtcagat | cttccacttt | gggtttgtcc | tctttgttgt | cactatcctc | 1200 |
| aacctgagta | ggtttgtcgg | tgggcgttgg | agcgggactg | ggggcagcac | tggtcgcagg | 1260 |
| ggtgccacta | ctgctagctg | cttccccaac | actcccggca | ggtttcagct | cgccaagttc | 1320 |
| ctgccgcttt | ttgaggattt | cgggcataga | ataatatccg | ttgatatgct | cgaattcttg | 1380 |
| gaccttcttc | ctgatgagtg | acatgacgcc | tatcctcgta | aggacgtgtt | gtcgagacaa | 1440 |
| accttcgcga | ggaactccgt | cagcaaaggt | ctctgcgttg | tcagcacccg | gctcgcaaag | 1500 |
| gtgccgcata | aagagggaaa | cgtaggcttt | gaaatgtttt | tcggactttc | ctcgaaggtc | 1560 |
| tcgaaccaac | cactgcgaat | tgaacgcatc | ttggggaggc | attccatacc | gcatgatcgc | 1620 |
| attgaggaag | gcctttcttt | gcctggcgtt | gaaaccaagg | acttcgatgt | ttccaccaac | 1680 |
| tctagcgaga | agtggtggca | gaggccggtc | tttctcttct | cgtctttcgg | gtcgcctctt | 1740 |
| cttcttcata | gtaccatcgt | | | | | 1760 |

<210> SEQ ID NO 38
<211> LENGTH: 1156
<212> TYPE: DNA
<213> ORGANISM: Lygus hesperus

<400> SEQUENCE: 38

| | | | | | |
|---|---|---|---|---|---|
| ggctcttgtc | tgtgaccctg | gtcgtcttct | gtaactttt | ctcttcgaat | ttttgagttt | 60 |
| ttgacttttg | tgacattcag | taggtactaa | aatcaccgaa | aatggctctc | agcgacgcag | 120 |

```
atgtacaaaa acaaatcaaa cacatgatgg ctttcattga gcaagaagcc aatgaaaaag      180
ccgaagaaat cgatgctaaa gctgaggaag agttcaacat tgaaagggt cgacttgtac      240 agaaccagcg attgaagatc atggactact acgagaggaa agagaagcaa gtcgagctcc      300
agaagaaaat ccaatcttcc aacatgttga accaagcgag gctgaaggct ttgaaagtac      360
gtgaagatca cgtaagaaat gtcatggacg atgctcgtaa aaggcttgtc cagtccgccc      420
aaaatcctca acaatactct gaaatcttga taaaactcgt catgcaagct ctccttcagt      480
tgttggagaa ggaagtcacc ctcaaaatca gagaaaagga ccaagacctc atcaacaacc      540
ttgtgcccat gatccaggac aagtacaagg agatctccgg tctcgatatc aagctcaaaa      600
tcgacactga ctccttcctt cctcccgagt ccagcggagg catcgaactc tatgctctta      660
agaactgcat gaaggtgtcc aacactctcg agagccgtct cgacctgatc gctcaacagc      720
tggtccctca ggtccgaact gctctcttcg gcaggaaccc caaccgtaga ttcgatgatt      780
agatcctcat tttcaaccca tccactcgag aaattatatc tttacgtata aaattattag      840
actcaggaat cccctccaa actcttgcat taaattttt cggtctagta ccaaattttg      900
aacaacgttt tcgttatcct attagtgctc agcttgctcc cttccactaa cctaaaacta      960
agcctaggta ccattctaat tccacatctc tccccccat atgttttctt aacggggggt     1020 ggaaattaa aggaaaaaaa taacattcca ctttttccaaa aaaccgggcc ccccccccct     1080 taaaacctc aaaaaaattc ctggtttttt tttagggggc ccccaaaaa aaatttttt      1140 tgggaaagcc ttaaca                                                    1156

<210> SEQ ID NO 39
<211> LENGTH: 2928
<212> TYPE: DNA
<213> ORGANISM: Lygus hesperus

<400> SEQUENCE: 39
cccacgcgtc cgggttggtg gtttggttgg actggacgac attctgcgaa gttaactttg       60
tctacaaata acagattcaa ccatggcttt acccagaatc cgtgatgagg agaaagaatc      120
cagatttgga tatgtattcg ccgtttctgg ccctgtcgtc actgcggaga gatgtcggg      180 ggccgctatg tacgagctgg tgcgcgtcgg gtacttcgag ttggtcggcg aaatcattcg      240
tcttgaagga gacatggcca ccattcaggt ctacgaagaa catccggtg taacagttgg      300 agatcccgtg ttgagaactg ggaaaccact ttccggtggag ctcggtccgg gtattatgag      360
cagcattttt gacggtattc agcgacctt gaaagacatt tgcgagctga ctcagagcat      420
ctacatcccc aagggagtca acgttccagc tctgtccagg tctattgcat gggacttcac      480
tccgtccaac aatatcaagg tgggagcaca catcactggt ggtgatttgt atgccgtcgt      540
tcacgaaaac acgcttgtca agcaaaaaat gatcatgccg ccagaggaa ggggtaccgt      600 gaaatacatc gctcccctg gcaactacac tgttgatgac gtcgtaatgg aaactgaatt      660
cgacggagag aaaactgaaa tcaagatgtt gcaagtttgg cctgtccgac agccccgtcc      720
agttgccgaa aaactgcctg ctaactatcc actcttgact ggtcaacgag ttttggatgc      780
cctcttcccg tgtgtccaag gtggtaccac cgccattccc ggtgccttcg gctgtggaaa      840
aactgtcatc tcacaagctc tgtccaaata ctcaaactct gacgtcatca tttacgtcgg      900
atgcggtgaa cgtggtaacg aaatgtctga ggtattgaga gatttccccg aactcacagt      960
tgagattgac ggtgtaactg agtccatcat gaagcgtact gctctggtcg ccaacacatc     1020
caacatgcct gtagctgctc gagaagcttc catttatact ggtatcacat gtccgaata     1080
```

```
cttccgtgac atgggttaca acgtgtcgat gatggctgac tccacctctc gatgggccga    1140
agccttgaga gaaatttcag gtcgtctcgc tgaaatgcct gctgacagtg gttaccctgc    1200
ctacttggga gcccgtttgg cttccttcta cgagcgagct ggtcgtgtca aatgtcttgg    1260
aagtcccgac agagagggct cagtcagtat cgtcggtgcc gtgtcgcctc ctggtggtga    1320
cttttcggat cctgtcactt cagccaccct tggtatcgta caggtcttct ggggtctcga    1380
caagaaattg gcacaaagga aacacttccc ctccatcaac tggctcatct cttacagtaa    1440
gtacatgaga gctttggacg acttctatga caaacggtac cctgaattcg tgcccctgag    1500
gaccaaggtc aaggagatcc tccaggagga agaagatttg gctgaaattg tgcagctcgt    1560
cggtaaaggt tcgctggccg agtctgataa gatcacattg gaaatcgcta agatcttgaa    1620
agacgatttc ttgcaacaaa acagctactc gccctacgac agattctgtc cgttctacaa    1680
gacggtcggt atgttgaaga acatgatctc tttctatgat cttgcgaggc acacggtgga    1740
atcaacagca caaagcgaca acaagatcac ttggactgtc atcaaagaaa gcatgggcaa    1800
catcctctac cagctgtcct caatgaaatt caaggacccc gtcaaagacg gagaagccaa    1860
gatcaaaggc gacttcgaac agctccacga agacatgcaa caagctttcc gcaacctcga    1920
agactaaaca gttttctcgt tcgctacctt attgttgaca atagtggcac tacagattaa    1980
cttcagtgca atttttaaca gcaaccgcaa atatcctcct cctccccccc ttgaaactca    2040
tactatcgtt acacaatttg tacatataaa aacacgtctg ttgtaattac acataattat    2100
tgtatatctt tcgagggtag tatttgggta gcagataatg aaactagta actagcgagt    2160 agactacaat attaaaaata ttctgtcaac cccaatcaat tcacgagaaa aagggaagc    2220 atttatgatt tgttttctc gcgagcacat tactttctac gagctgcatt ccaatccttt    2280
aatttcttag tcgtgtcatt tcaacgtgtt caatttattg attgacttcg ttgtatcact    2340
tcggtctagt tttccttgtc tcggttaatt gttaagcttt acaagtagag aaaaaaaagt    2400 acttttttaat tcagtattaa attgttttt tgtaatatag gtggcgtgtc taatagaaaa    2460
agacaatttg ctccgcttgg gcaaaactac aaggaacata actcttctgg atttgattct    2520
ttcgttgtgt gatatttttc gaagtctact tttccccatt ttcgagcgca aaagcttcgg    2580 tacttacccct ccaaattttg aaaattaata tctgaagtgt gaagatgaac gagttcaact    2640
ggaacaactc ttgggagttt ctaattcaca ggatgtttct gtacctataa cttttaatta    2700
ttttctgttc aggatgtttt taatcaaatt aagattaaat attgtattat attgttgaaa    2760
aaggtttttt tttttttggc ttccaagtaa agccagtaat tgtttacatt tccttggaaa    2820 cttttttgtgt agttagggct actgaacgct ctattatttc tgtgaagggg cagagtaaaa    2880
ataaaatatt ttgaaaagtt gttaaaaaaa aaaaaaaaa gggggggg                  2928
```

<210> SEQ ID NO 40
<211> LENGTH: 1894
<212> TYPE: DNA
<213> ORGANISM: Artificial
<220> FEATURE:
<223> OTHER INFORMATION: Synthetic

<400> SEQUENCE: 40

```
ggtccgattg agacttttca acaaagggta atatccggaa acctcctcgg attccattgc      60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa     180
gatggacccc cacccacgag gagcatcgtg gaaaagaag acgttccaac cacgtcttca     240
```

```
aagcaagtgg attgatgtga tggtccgatt gagactttc aacaaagggt aatatccgga      300
aacctcctcg gattccattg cccagctatc tgtcacttta ttgtgaagat agtggaaaag      360
gaaggtggct cctacaaatg ccatcattgc gataaaggaa aggccatcgt tgaagatgcc      420
tctgccgaca gtggtcccaa agatggaccc ccacccacga ggagcatcgt ggaaaagaa       480
gacgttccaa ccacgtcttc aaagcaagtg gattgatgtg atatctccac tgacgtaagg      540
gatgacgcac aatcccacta tccttcgcaa gacccttcct ctatataagg aagttcattt      600
catttggaga ggacacgctg acaagctgac tctagcagat atcaaacaag tttgtacaaa      660
aaagcaggct ccgcggccgc ccccttcacc agatctccat ggctatccta gaccttaagt      720
ccctcgtgct gaacgccatt aactactggg gccctaagaa caacaacggc atccagggcg      780
gtgacttcgg ctaccccatc tctgagaagc agatcgcaca tagcatcatt accttcaccc      840
accctcgctt gatcccctac gatcttacta tcccgcagaa ccttgagacc atcttcacca      900
caacgcaggt gctcaccaat aacactgacc tccagcaatc ccagaccgtg agctttgcga      960
agaagaccac taccacgacc tcaactagca cgaccaacgg ttggacagaa ggaggcaaga     1020
tcagcgcacg gctggaggag aaagtttcgg ttagcattcc gttcatcggt gagggtggcg     1080
ggaagaactc gactaccata gaggccaact tcgcacacaa ctctagcacc actaccttcc     1140
agcaagcaag cactgacatt gagtggaaca ttagccaacc ggtgctggtt cctccctcta     1200
aacaagttgt cgcgaccctt gtgatcatgg gaggcaactt taccatccct atggacttga     1260
tgaccacgat tgatagtaca gagcactact cccactactc cggttaccct atcctcacct     1320
ggatctcgtc cccagataac tcttactccg gtccctttat gtcatggtac tttgcaaact     1380
ggcctaacct tccgagtgga ttcggcccac tgaatagtga taacacggtc acatacactg     1440
gctctgtcgt gtcccaagtt tcggccggtg tctacgctac cgtccggttc gatcagtatg     1500
acattcacaa tctccgtact atcgagaaga cttggtatgc tcgccatgcg acgctgcata     1560
atggcaagaa gatttctatc aacaatgtca cggaaatggc tccaacatcc cctatcaaga     1620
caaattgagg atccaattcc cgatcgttca aacatttggc aataaagttt cttaagattg     1680
aatcctgttg ccggtcttgc gatgattatc atataatttc tgttgaatta cgttaagcat     1740
gtaataatta acatgtaatg catgacgtta tttatgagat gggtttttat gattagagtc     1800
ccgcaattat acatttaata cgcgatagaa aacaaaatat agcgcgcaaa ctaggataaa     1860
ttatcgcgcg cggtgtcatc tatgttacta gatc                                  1894
```

<210> SEQ ID NO 41
<211> LENGTH: 340
<212> TYPE: PRT
<213> ORGANISM: Bacillus thuringiensis

<400> SEQUENCE: 41

Met Ala Ile Met Asn Asp Ile Ala Gln Asp Ala Arg Ala Trp Asp
1               5                   10                  15

Ile Ile Ala Gly Pro Phe Ile Arg Pro Gly Thr Thr Pro Thr Asn Arg
                20                  25                  30

Gln Leu Phe Asn Tyr Gln Ile Gly Asn Ile Glu Val Glu Pro Gly Asn
            35                  40                  45

Leu Asn Phe Ser Val Val Pro Glu Leu Asp Phe Ser Val Ser Gln Asp
        50                  55                  60

Leu Phe Asn Asn Thr Ser Val Gln Gln Ser Gln Thr Ala Ser Phe Asn
65                  70                  75                  80

```
Glu Ser Arg Thr Glu Thr Ser Thr Ala Val Thr His Gly Val Lys
            85                  90                  95
Ser Gly Val Thr Val Ser Ala Ser Ala Lys Phe Asn Ala Lys Ile Leu
            100                 105                 110
Val Lys Ser Ile Glu Gln Thr Ile Thr Thr Val Ser Thr Glu Tyr
            115                 120                 125
Asn Phe Ser Ser Thr Thr Thr Arg Thr Asn Thr Val Thr Arg Gly Trp
130                 135                 140
Ser Ile Ala Gln Pro Val Leu Val Pro Pro His Ser Arg Val Thr Ala
145                 150                 155                 160
Thr Leu Gln Ile Tyr Lys Gly Asp Phe Thr Val Pro Val Leu Leu Ser
                165                 170                 175
Leu Arg Val Tyr Gly Gln Thr Gly Thr Leu Ala Gly Asn Pro Ser Phe
            180                 185                 190
Pro Ser Leu Tyr Ala Ala Thr Tyr Glu Asn Thr Leu Leu Gly Arg Ile
            195                 200                 205
Arg Glu His Ile Ala Pro Pro Ala Leu Phe Arg Ala Ser Asn Ala Tyr
            210                 215                 220
Ile Ser Asn Gly Val Gln Ala Ile Trp Arg Gly Thr Ala Thr Arg
225                 230                 235                 240
Val Ser Gln Gly Leu Tyr Ser Val Val Arg Ile Asp Glu Arg Pro Leu
                245                 250                 255
Ala Gly Tyr Ser Gly Glu Thr Arg Thr Tyr Tyr Leu Pro Val Thr Leu
            260                 265                 270
Ser Asn Ser Ser Gln Ile Leu Thr Pro Gly Ser Leu Gly Ser Glu Ile
            275                 280                 285
Pro Ile Ile Asn Pro Val Pro Asn Ala Ser Cys Lys Lys Glu Asn Ser
290                 295                 300
Pro Ile Ile Ile His His Asp Arg Glu Lys His Arg Glu Arg Asp Tyr
305                 310                 315                 320
Asp Lys Glu His Ile Cys His Asp Gln Ala Glu Lys Tyr Glu Arg Asp
                325                 330                 335
Tyr Asp Lys Glu
            340

<210> SEQ ID NO 42
<211> LENGTH: 2101
<212> TYPE: DNA
<213> ORGANISM: Artificial
<220> FEATURE:
<223> OTHER INFORMATION: Synthetic

<400> SEQUENCE: 42
ggtccgattg agactttca acaaagggta atatccggaa acctcctcgg attccattgc      60
ccagctatct gtcactttat tgtgaagata gtggaaaagg aaggtggctc ctacaaatgc    120
catcattgcg ataaggaaa ggccatcgtt gaagatgcct ctgccgacag tggtcccaaa    180
gatggacccc cacccacgag gagcatcgtg gaaaaagaag acgttccaac cacgtcttca    240
aagcaagtgg attgatgtga tgtccgatt gagacttttc aacaaagggt aatatccgga    300
aacctcctcg gattccattg cccagctatc tgtcacttta ttgtgaagat agtggaaaag    360
gaaggtggct cctacaaatg ccatcattgc gataaggaaa ggccatcgt tgaagatgcc    420 tctgccgaca gtggtcccaa agatggaccc ccacccacga ggagcatcgt ggaaaaagaa    480
gacgttccaa ccacgtcttc aaagcaagtg gattgatgtg atatctccac tgacgtaagg    540
gatgacgcac aatcccacta tccttcgcaa gaccccttcct ctatataagg aagttcattt    600
```

```
catttggaga ggacacagaa acattcgcaa aaacaaaatc ccagtatcaa aattcttctc      660 ttttttttcat atttcgcaaa gatttaaaaa gatctgctag aaataatttt gtttaacttt     720
aagaaggaga tatatccatg gcgcaagtta gcagaatctg caatggtgtg cagaacccat     780
ctcttatctc caatctctcg aaatccagtc aacgcaaatc tcccttatcg gtttctctga     840
agacgcagca gcatccacga gcttatccga tttcgtcgtc gtggggattg aagaagagtg     900
ggatgacgtt aattggctct gagcttcgtc ctcttaaggt catgtcttct gtttccacgg     960
cgtgcatggc tatcctagac cttaagtccc tcgtgctgaa cgccattaac tactggggcc    1020
ctaagaacaa caacggcatc cagggcggtg acttcggcta ccccatctct gagaagcaga    1080
tcgacactag catcattacc ttcacccacc ctcgcttgat cccctacgat cttactatcc    1140
cgcagaacct tgagaccatc ttcaccacaa cgcaggtgct caccaataac actgacctcc    1200
agcaatccca gaccgtgagc tttgcgaaga agaccactac cacgacctca actagcacga    1260
ccaacggttg gacagaagga ggcaagatca gcgacacgct ggaggagaaa gtttcggtta    1320
gcattccgtt catcggtgag ggtggcggga agaactcgac taccatagag gccaacttcg    1380
cacacaactc tagcaccact accttccagc aagcaagcac tgacattgag tggaacatta    1440
gccaaccggt gctggttcct ccctctaaac aagttgtcgc gacccttgtg atcatgggag    1500
gcaactttac catccctatg gacttgatga ccacgattga tagtacagag cactactccc    1560
actactccgg ttaccctatc ctcacctgga tctcgtcccc agataactct tactccggtc    1620
cctttatgtc atggtacttt gcaaactggc ctaaccttcc gagtggattc ggcccactga    1680
atagtgataa cacggtcaca tacactggct ctgtcgtgtc ccaagtttcg gccggtgtct    1740
acgctaccgt ccggttcgat cagtatgaca ttcacaatct ccgtactatc gagaagactt    1800
ggtatgctcg ccatgcgacg ctgcataatg gcaagaagat ttctatcaac aatgtcacgg    1860
aaatggctcc aacatcccct atcaagacaa attgaggatc caaatcacca gtctctctct    1920
acaaatctat ctctctctat ttttctccag aataatgtgt gagtagttcc cagataaggg    1980
aattagggtt cttatagggt ttcgctcatg tgttgagcat ataagaaacc cttagtatgt    2040
atttgtattt gtaaaatact tctatcaata aaatttctaa ttcctaaaac caaaatccag    2100
t                                                                   2101
```

```
<210> SEQ ID NO 43
<211> LENGTH: 1873
<212> TYPE: DNA
<213> ORGANISM: Artificial
<220> FEATURE:
<223> OTHER INFORMATION: Synthetic

<400> SEQUENCE: 43
```

```
ggtccgattg agacttttca acaaagggta atatccggaa acctcctcgg attccattgc      60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa     180
gatggacccc cacccacgag gagcatcgtg gaaaagaag acgttccaac cacgtcttca     240
aagcaagtgg attgatgtga tgtccgattg agacttttc aacaaagggt aatatccgga     300
aacctcctcg gattccattg cccagctatc tgtcacttta ttgtgaagat agtggaaaag     360
gaaggtggct cctacaaatg ccatcattgc gataaaggaa aggccatcgt tgaagatgcc     420
tctgccgaca gtggtcccaa agatggaccc ccacccacga ggagcatcgt ggaaaagaa     480 gacgttccaa ccacgtcttc aaagcaagtg gattgatgtg atatctccac tgacgtaagg     540
```

```
gatgacgcac aatcccacta tccttcgcaa gacccttcct ctatataagg aagttcattt      600
catttggaga ggacacagaa acattcgcaa aaacaaaatc ccagtatcaa aattcttctc      660 ttttttttcat atttcgcaaa gatttaaaaa gatctgctag aaataatttt gtttaacttt    720
aagaaggaga tatatccatg gctatcctag accttaagtc cctcgtgctg aacgccatta     780
actactgggg ccctaagaac aacaacggca tccagggcgg tgacttcggc tacccccatct    840 ctgagaagca gatcgacact agcatcatta ccttcaccca ccctcgcttg atcccctacg     900
atcttactat cccgcagaac cttgagacca tcttcaccac aacgcaggtg ctcaccaata     960
acactgacct ccagcaatcc cagaccgtga gctttgcgaa gaagaccact accacgacct    1020
caactagcac gaccaacggt tggacagaag gaggcaagat cagcgacacg ctggaggaga    1080
aagtttcggt tagcattccg ttcatcggtg agggtggcgg gaagaactcg actaccatag    1140
aggccaactt cgcacacaac tctagcacca ctaccttcca gcaagcaagc actgacattg    1200
agtggaacat tagccaaccg gtgctggttc ctccctctaa acaagttgtc gcgacccttg    1260
tgatcatggg aggcaacttt accatcccta tggacttgat gaccacgatt gatagtacag    1320
agcactactc ccactactcc ggttacccta tcctcacctg gatctcgtcc ccagataact    1380
cttactccgg tcccttatg tcatggtact ttgcaaactg gcctaacctt ccgagtggat     1440
tcggcccact gaatagtgat aacacggtca catacactgg ctctgtcgtg tcccaagttt    1500
cggccggtgt ctacgctacc gtccggttcg atcagtatga cattcacaat ctccgtacta    1560 tcgagaaagac ttggtatgct cgccatgcga cgctgcataa tggcaagaag atttctatca   1620
acaatgtcac ggaaatggct ccaacatccc ctatcaagac aaattgagga tccaaatcac    1680
cagtctctct ctacaaatct atctctctct attttttctcc agaataatgt gtgagtagtt   1740
cccagataag ggaattaggg ttcttatagg gtttcgctca tgtgttgagc atataagaaa    1800
cccttagtat gtatttgtat ttgtaaaata cttctatcaa taaatttct aattcctaaa     1860 accaaaatcc agt                                                       1873

<210> SEQ ID NO 44
<211> LENGTH: 930
<212> TYPE: DNA
<213> ORGANISM: Artificial
<220> FEATURE:
<223> OTHER INFORMATION: Synthetic

<400> SEQUENCE: 44
atggcaattt tagatttaaa atctttagta ctcaatgcaa taattattg gggtcctaaa       60 aataataatg gcatacaggg tggtgatttt ggttacccta tcagaaaaa acaaatagat     120 acgtctatta aacttttac tcatcctcgt ttaattccat atgatttaac aattcctcaa     180
aatttagaaa ctattttac tacaactcaa gtattaacaa ataatacaga tttacaacaa    240
agtcaaactg tttcttttgc taaaaaaaca acgacaacaa cttcaacttc aactacaaat   300
ggttggacag aaggtgggaa aatttcagat acattagaag aaaaagtaag tgtatctatt    360 cctttttattg gagagggagg aggaaaaaac agtacaacta gaagctaa ttttgcacat    420 aactctagta ctactacttt tcaacaggct tcaactgata tagagtggaa tatttcacaa   480
ccagtattgg ttcccccaag taaacaagtt gtagcaacat tagttattat gggaggtaat   540
tttactattc ctatggattt gatgactact atagattcta cagaacatta tagccattat   600
agtggttatc caatattaac atggatacg agccccgata atagttatag tggtccattt   660
atgagttggt attttgcaaa ttggcccaat ttaccatcgg ggtttggtcc tttaaattca    720
```

| | |
|---|---|
| gataatacgg tcacttatac aggttctgtt gtaagtcaag tatcagctgg tgtatatgcc | 780 |
| actgtacgat ttgatcaata tgatatacac aatttaagga caattgaaaa aacttggtat | 840 |
| gcacgacatg caactcttca taatggaaag aaaatatcta taaataatgt tactgaaatg | 900 |
| gcaccaacaa gtccaataaa aacaaattaa | 930 |

<210> SEQ ID NO 45
<211> LENGTH: 930
<212> TYPE: DNA
<213> ORGANISM: Artificial
<220> FEATURE:
<223> OTHER INFORMATION: Synthetic

<400> SEQUENCE: 45

| | |
|---|---|
| atggctatcc tcgatcttaa gtccctcgtt ctgaacgcta tcaactactg gggccccaag | 60 |
| aacaataacg gtattcaggg cggtgacttc ggctacccta tctctgagaa gcagattgat | 120 |
| acttccatta ttaccttcac tcatcctagg cttattccct atgacctgac tattccacag | 180 |
| aatctggaga ctatcttcac taccacgcag gtgcttacta acaacactga cttgcaacag | 240 |
| tctcagactg ttagcttcgc caagaagact accactacaa cctccacttc taccacaaac | 300 |
| gggtggactg agggtggcaa gatcagcgac actctcgaag agaaggtgtc agtctctatc | 360 |
| cccttcattg gcgagggcgg tggaaagaac tctactacta ttgaagcgaa cttcgctcat | 420 |
| aattcttcca ctaccacttt ccaacaggca tctactgaca tagaatggaa catctctcaa | 480 |
| ccggtccttg tgcctccctc taaacaggtt gttgccactc tcgttatcat gggtggcaac | 540 |
| ttcactattc ctatggatct tatgactacc attgactcta ctgagcatta ctctcactac | 600 |
| tctggctacc ccattctcac ttggatctct tctcctgaca atagctactc cggtccattc | 660 |
| atgtcatggt acttcgctaa ctggccgaat ctcccttctg gctttggtcc tcttaactct | 720 |
| gataacactg tgacctacac tggctctgtc gtcagtcagg tctctgccgg tgtgtacgca | 780 |
| actgttcgct tcgatcagta tgacatccat aatctcagga ctattgagaa gacctggtac | 840 |
| gctcgtcatg cgacgcttca caacggcaag aagatcagca tcaataacgt gacagaaatg | 900 |
| gcccctacca gcccgatcaa gactaactga | 930 |

<210> SEQ ID NO 46
<211> LENGTH: 930
<212> TYPE: DNA
<213> ORGANISM: Artificial
<220> FEATURE:
<223> OTHER INFORMATION: Synthetic

<400> SEQUENCE: 46

| | |
|---|---|
| atggctatcc tggacttgaa atcccttgtg ctcaacgcta tcaactattg gggccctaaa | 60 |
| aacaacaacg gaatccaggg cggtgacttt ggatacccca tctctgagaa acagatcgac | 120 |
| acttccatca ttacattcac ccatccacgt cttatccctt acgatcttac cattcctcag | 180 |
| aatcttgaga ccatcttcac aactactcag gtgttgacta acaacacaga cctccagcag | 240 |
| tcccaaacgg tttcctttgc gaagaaaacg actaccacga caagtacttc gactactaat | 300 |
| ggttggacag agggtggcaa aatctcagac actctggagg agaaagtgag cgtgtctatc | 360 |
| ccattcattg gggagggagg tgggaagaac tctacaacca tcgaggcaaa cttcgctcac | 420 |
| aatagtagca caaccacctt ccagcaagct tccaccgaca tcgaatggaa catctcacaa | 480 |
| ccggttctcg tccctccctc taagcaggtc gtcgcaaccc tcgtcatcat gggaggcaac | 540 |
| ttcactatcc ctatggatct catgactacc attgattcta ccgaacatta ctcacattac | 600 |

| | |
|---|---|
| agcggttatc ctatcctcac ctggatctca tccnctgata actcatacag cggcccattc | 660 |
| atgtcatggt acttcgcaaa ctggcccaac cttccatcag gatttggtcc actaaacagc | 720 |
| gataacaccg tcacttacac tggttccgtg gtctcccagg tttctgctgg cgtttatgca | 780 |
| acagtgcgtt tcgatcaata cgacattcat aacctcagga ccatcgagaa gacttggtac | 840 |
| gcaaggcacg ctacacttca caatggcaag aagatttcca tcaacaacgt cactgaaatg | 900 |
| gcacctacct ctccgatcaa gactaactga | 930 |

<210> SEQ ID NO 47
<211> LENGTH: 930
<212> TYPE: DNA
<213> ORGANISM: Artificial
<220> FEATURE:
<223> OTHER INFORMATION: Synthetic

<400> SEQUENCE: 47

| | |
|---|---|
| atggccatcc tggacctgaa gagcctcgtg ctgaacgcta tcaactactg ggccctaag | 60 |
| aacaacaatg gtatccaagg tggcgacttc ggctacccca tcagcgagaa gcagatcgac | 120 |
| acgagcatca tcacgttcac ccatccgcgc ctcatcccgt acgacctcac catcccgcag | 180 |
| aacctggaga ccatcttcac gacgacccag gtgctcacca acaacacgga tctccagcag | 240 |
| tcgcagaccg tgagcttcgc gaagaagacc actaccacga cctccacgag caccacgaac | 300 |
| ggctggaccg aaggaggcaa gatcagcgac accctggagg agaaggtgtc cgtgtcgatc | 360 |
| cccttcatcg gcgagggcgg cggcaagaac tccaccacca tcgaagcgaa cttcgcccac | 420 |
| aactccagca ccactacctt ccagcaggcc tcgaccgaca tcgaatggaa catcagccaa | 480 |
| ccggtcctgg tcccgccctc caagcaggtg gtggcgacgc tcgtcatcat gggcgggaac | 540 |
| ttcaccatcc cgatggatct tatgaccacc atcgacagca ccgagcatta tcgcactac | 600 |
| tcgggctacc cgatcctcac ctggatctcg tcccccgaca actcgtacag cggcccgttc | 660 |
| atgtcctggt acttcgcgaa ctggcctaac ctccccagcg ggttcggccc gctgaacagc | 720 |
| gacaacacag tgacctacac cggcagcgtg gtctcccagg tgtcggctgg ggtgtacgcg | 780 |
| accgtccgct tcgatcagta cgacatccac aacctccgca ctatcgagaa gacatggtac | 840 |
| gcgaggcacg cgaccctcca caacggcaag aagatcagca tcaacaacgt gaccgagatg | 900 |
| gccccgactt ctcccatcaa gaccaactga | 930 |

<210> SEQ ID NO 48
<211> LENGTH: 930
<212> TYPE: DNA
<213> ORGANISM: Artificial
<220> FEATURE:
<223> OTHER INFORMATION: Synthetic

<400> SEQUENCE: 48

| | |
|---|---|
| atggccatcc tggacctgaa gagcctcgtg ctgaacgcta tcaactactg ggccctaag | 60 |
| aacaacaatg gtatccaagg tggcgacttc ggctacccca tcagcgagaa gcagatcgac | 120 |
| acgagcatca tcacgttcac ccatccgcgc ctcatcccgt acgacctcac catcccgcag | 180 |
| aacctggaga ccatcttcac gacgacccag gtgctcacca acaacacgga tctccagcag | 240 |
| tcgcagaccg tgagcttcgc gaagaagacc actaccacga cctccacgag caccacgaac | 300 |
| ggctggaccg aaggaggcaa gatcagcgac accctggagg agaaggtgtc cgtgtcgatc | 360 |
| cccttcatcg gcgagggcgg cggcaagaac tccaccacca tcgaagcgaa cttcgcccac | 420 |
| aactccagca ccactacctt ccagcaggcc tcgaccgaca tcgaatggaa catcagccaa | 480 |

```
ccggtgctgg ttcctccctc taaacaagtt gtcgcgaccc ttgtgatcat gggaggcaac    540
tttaccatcc ctatggactt gatgaccacg attgatagta cagagcacta ctcccactac    600
tccggttacc ctatcctcac ctggatctcg tccccagata actcttactc cggtcccttt    660
atgtcatggt actttgcaaa ctggcctaac cttccgagtg gattcggccc actgaatagt    720
gataacacgg tcatacacac tggctctgtc gtgtcccaag tttcggccgg tgtctacgct    780
accgtccggt tcgatcagta tgacattcac aatctccgta ctatcgagaa gacttggtat    840
gctcgccatg cgacgctgca taatggcaag aagatttcta tcaacaatgt cacggaaatg    900
gctccaacat cccctatcaa gacaaattga                                     930

<210> SEQ ID NO 49
<211> LENGTH: 930
<212> TYPE: DNA
<213> ORGANISM: Artificial
<220> FEATURE:
<223> OTHER INFORMATION: Synthetic

<400> SEQUENCE: 49
atggccatcc tggacctgaa gagcctcgtg ctgaacgcta tcaactactg gggccctaag     60
aacaacaatg gtatccaagg tggcgacttc ggctacccca tcagcgagaa gcagatcgac    120
acgagcatca tcacgttcac ccatccgcgc tcatcccgt acgacctcac catcccgcag    180
aacctggaga ccatcttcac gacgacccag gtgctcacca caacacgga tctccagcag    240 tcgcagaccg tgagcttcgc gaagaagacc actaccacga cctccacgag caccacgaac    300
ggctggaccg aaggaggcaa gatcagcgac accctggagg agaaggtgtc cgtgtcgatc    360
cccttcatcg gcgagggcgg cggcaagaac tccaccacca tcgaagcgaa cttcgcccac    420
aactccagca ccactacctt ccagcaggcc tcgaccgaca tcgaatggaa catcagccaa    480
ccggtccttg tgcctccctc taaacaggtt gttgccactc tcgttatcat gggtggcaac    540
ttcactattc ctatggatct tatgactacc attgactcta ctgagcatta ctctcactac    600
tctggctacc ccattctcac ttggatctct tctcctgaca atagctactc cggtccattc    660
atgtcatggt acttcgctaa ctggccgaat ctcccttctg gctttggtcc tcttaactct    720
gataacactg tgacctacac tggctctgtc gtcagtcagg tctctgccgg tgtgtacgca    780
actgttcgct tcgatcagta tgacatccat aatctcagga ctattgagaa gacctggtac    840
gctcgtcatg cgacgcttca caacggcaag aagatcagca tcaataacgt gacagaaatg    900
gcccctacca gcccgatcaa gactaactga                                     930

<210> SEQ ID NO 50
<211> LENGTH: 930
<212> TYPE: DNA
<213> ORGANISM: Artificial
<220> FEATURE:
<223> OTHER INFORMATION: Synthetic

<400> SEQUENCE: 50
atggccatcc tggacctgaa gagcctcgtg ctgaacgcta tcaactactg gggccctaag     60
aacaacaatg gtatccaagg tggcgacttc ggctacccca tcagcgagaa gcagatcgac    120
acgagcatca tcacgttcac ccatccgcgc tcatcccgt acgacctcac catcccgcag    180
aacctggaga ccatcttcac gacgacccag gtgctcacca caacacgga tctccagcag    240 tcgcagaccg tgagcttcgc gaagaagacc actaccacga cctccacgag caccacgaac    300
ggctggaccg aaggaggcaa gatcagcgac accctggagg agaaggtgtc cgtgtcgatc    360
```

```
cccttcatcg gcgagggcgg cggcaagaac tccaccacca tcgaagcgaa cttcgcccac      420
aactccagca ccactacctt ccagcaggcc tcgaccgaca tcgaatggaa catcagccaa      480
ccggttctcg tccctccctc taagcaggtc gtcgcaaccc tcgtcatcat gggaggcaac      540
ttcactatcc ctatggatct catgactacc attgattcta ccgaacatta ctcacattac      600
agcggttatc ctatcctcac ctggatctca tccctgata  actcatacag cggcccattc      660
atgtcatggt acttcgcaaa ctggcccaac cttccatcag gatttggtcc actaaacagc      720
gataacaccg tcacttacac tggttccgtg gtctcccagg tttctgctgg cgtttatgca      780
acagtgcgtt tcgatcaata cgacattcat aacctcagga ccatcgagaa gacttggtac      840
gcaaggcacg ctacacttca caatggcaag aagatttcca tcaacaacgt cactgaaatg      900
gcacctacct ctccgatcaa gactaactga                                      930
```

```
<210> SEQ ID NO 51
<211> LENGTH: 930
<212> TYPE: DNA
<213> ORGANISM: Artificial
<220> FEATURE:
<223> OTHER INFORMATION: Synthetic

<400> SEQUENCE: 51
atggctatcc tagaccttaa gtccctcgtg ctgaacgcca ttaactactg gggccctaag       60
aacaacaacg gcatccaggg cggtgacttc ggctacccca tctctgagaa gcagatcgac      120
actagcatca ttaccttcac ccaccctcgc ttgatcccct acgatcttac tatcccgcag      180
aaccttgaga ccatcttcac cacaacgcag gtgctcacca ataacactga cctccagcaa      240
tcccagaccg tgagctttgc gaagaagacc actaccacga cctcaactag cacgaccaac      300
ggttggacag aaggaggcaa gatcagcgac acgctggagg agaaagtttc ggttagcatt      360
ccgttcatcg gtgagggtgg cgggaagaac tcgactacca tagaggccaa cttcgcacac      420
aactctagca ccactacctt ccagcaagca agcactgaca ttgagtggaa cattagccaa      480
ccggtccttg tgcctccctc taaacaggtt gttgccactc tcgttatcat gggtggcaac      540
ttcactattc ctatggatct tatgactacc attgactcta ctgagcatta ctctcactac      600
tctggctacc ccattctcac ttggatctct tctcctgaca atagctactc cggtccattc      660
atgtcatggt acttcgctaa ctggccgaat ctcccttctg gctttggtcc tcttaactct      720
gataacactg tgacctacac tggctctgtc gtcagtcagg tctctgccgg tgtgtacgca      780
actgttcgct tcgatcagta tgacatccat aatctcagga ctattgagaa gacctggtac      840
gctcgtcatg cgacgcttca caacggcaag aagatcagca tcaataacgt gacagaaatg      900 gccccctacca gcccgatcaa gactaactga                                     930
```

```
<210> SEQ ID NO 52
<211> LENGTH: 930
<212> TYPE: DNA
<213> ORGANISM: Artificial
<220> FEATURE:
<223> OTHER INFORMATION: Synthetic

<400> SEQUENCE: 52
atggctatcc tagaccttaa gtccctcgtg ctgaacgcca ttaactactg gggccctaag       60
aacaacaacg gcatccaggg cggtgacttc ggctacccca tctctgagaa gcagatcgac      120
actagcatca ttaccttcac ccaccctcgc ttgatcccct acgatcttac tatcccgcag      180
aaccttgaga ccatcttcac cacaacgcag gtgctcacca ataacactga cctccagcaa      240
```

```
tcccagaccg tgagctttgc gaagaagacc actaccacga cctcaactag cacgaccaac    300
ggttggacag aaggaggcaa gatcagcgac acgctggagg agaaagtttc ggttagcatt    360
ccgttcatcg gtgagggtgg cgggaagaac tcgactacca tagaggccaa cttcgcacac    420
aactctagca ccactacctt ccagcaagca agcactgaca ttgagtggaa cattagccaa    480
ccggttctcg tccctccctc taagcaggtc gtcgcaaccc tcgtcatcat gggaggcaac    540
ttcactatcc ctatggatct catgactacc attgattcta ccgaacatta ctcacattac    600
agcggttatc ctatcctcac ctggatctca tccctgata  actcatacag cggcccattc    660
atgtcatggt acttcgcaaa ctggcccaac cttccatcag gatttggtcc actaaacagc    720
gataacaccg tcacttacac tggttccgtg gtctcccagg tttctgctgg cgtttatgca    780
acagtgcgtt tcgatcaata cgacattcat aacctcagga ccatcgagaa gacttggtac    840
gcaaggcacg ctacacttca caatggcaag aagatttcca tcaacaacgt cactgaaatg    900
gcacctacct ctccgatcaa gactaactga                                      930

<210> SEQ ID NO 53
<211> LENGTH: 930
<212> TYPE: DNA
<213> ORGANISM: Artificial
<220> FEATURE:
<223> OTHER INFORMATION: Synthetic

<400> SEQUENCE: 53
atggctatcc tagaccttaa gtccctcgtg ctgaacgcca ttaactactg gggccctaag     60
aacaacaacg gcatccaggg cggtgacttc ggctacccca tctctgagaa gcagatcgac    120
actagcatca ttaccttcac ccaccctcgc ttgatcccct acgatcttac tatcccgcag    180
aaccttgaga ccatcttcac cacaacgcag gtgctcacca ataacactga cctccagcaa    240
tcccagaccg tgagctttgc gaagaagacc actaccacga cctcaactag cacgaccaac    300
ggttggacag aaggaggcaa gatcagcgac acgctggagg agaaagtttc ggttagcatt    360
ccgttcatcg gtgagggtgg cgggaagaac tcgactacca tagaggccaa cttcgcacac    420
aactctagca ccactacctt ccagcaagca agcactgaca ttgagtggaa cattagccaa    480
ccggtcctgg tcccgccctc caagcaggtg gtggcgacgc tcgtcatcat gggcgggaac    540
ttcaccatcc cgatggatct tatgaccacc atcgacagca ccgagcatta ctcgcactac    600
tcgggctacc cgatcctcac ctggatctcg tccccgaca  actcgtacag cggcccgttc    660
atgtcctggt acttcgcgaa ctggcctaac ctccccagcg ggttcggccc gctgaacagc    720
gacaacacag tgacctacac cggcagcgtg gtctcccagg tgtcggctgg ggtgtacgcg    780
accgtccgct tcgatcagta cgacatccac aacctccgca ctatcgagaa gacatggtac    840
gcgaggcacg cgaccctcca caacggcaag aagatcagca tcaacaacgt gaccgagatg    900
gccccgactt ctcccatcaa gaccaactga                                      930

<210> SEQ ID NO 54
<211> LENGTH: 2101
<212> TYPE: DNA
<213> ORGANISM: Artificial
<220> FEATURE:
<223> OTHER INFORMATION: Synthetic

<400> SEQUENCE: 54
ggtccgattg agacttttca acaaagggta atatccggaa acctcctcgg attccattgc     60
ccagctatct gtcactttat tgtgaagata gtggaaaagg aaggtggctc ctacaaatgc    120
```

```
catcattgcg ataaaggaaa ggccatcgtt gaagatgcct ctgccgacag tggtcccaaa      180
gatggacccc cacccacgag gagcatcgtg aaaaagaag acgttccaac cacgtcttca       240
aagcaagtgg attgatgtga tggtccgatt gagactttc aacaaagggt aatatccgga       300
aacctcctcg gattccattg cccagctatc tgtcacttta ttgtgaagat agtggaaaag      360
gaaggtggct cctacaaatg ccatcattgc gataaaggaa aggccatcgt tgaagatgcc      420
tctgccgaca gtggtcccaa agatggaccc ccacccacga ggagcatcgt ggaaaaagaa      480
gacgttccaa ccacgtcttc aaagcaagtg gattgatgtg atatctccac tgacgtaagg      540
gatgacgcac aatcccacta tccttcgcaa gacccttcct ctatataagg aagttcattt      600
catttggaga ggacacagaa acattcgcaa aaacaaaatc ccagtatcaa aattcttctc      660 ttttttttcat atttcgcaaa gatttaaaaa gatctgctag aaataatttt gtttaacttt     720
aagaaggaga tatatccatg gcgcaagtta gcagaatctg caatggtgtg cagaacccat      780
ctcttatctc caatctctcg aaatccagtc aacgcaaatc tcccttatcg gtttctctga      840
agacgcagca gcatccacga gcttatccga tttcgtcgtc gtggggattg aagaagagtg      900
ggatgacgtt aattggctct gagcttcgtc ctcttaaggt catgtcttct gtttccacgg      960
cgtgcatggc tatcctagac cttaagtccc tcgtgctgaa cgccattaac tactggggcc     1020
ctaagaacaa caacggcatc cagggcgtg acttcggcta ccccatctct gagaagcaga     1080
tcgacactag catcattacc ttcacccacc ctcgcttgat ccctacgat cttactatcc      1140 cgcagaacct tgagaccatc ttcaccacaa cgcaggtgct caccaataac actgacctcc     1200
agcaatccca gaccgtgagc tttgcgaaga agaccactac cacgacctca actagcacga     1260
ccaacggttg gacagaagga ggcaagatca gcgacacgct ggaggagaaa gtttcggtta     1320
gcattccgtt catcggtgag ggtggcggga agaactcgac taccatagag gccaacttcg     1380
cacacaactc tagcaccact accttccagc aagcaagcac tgacattgag tggaacatta     1440
gccaaccggt gctggttcct ccctctaaac aagttgtcgc gaccccttgtg atcatgggag     1500 gcaactttac catccctatg gacttgatga ccacgattga tagtacagag cactactccc      1560
actactccgg ttaccctatc ctcacctgga tctcgtcccc agataactct tactccggtc     1620
cctttatgtc atggtacttt gcaaactggc ctaaccttcc gagtggattc ggcccactga     1680
atagtgataa cacggtcaca tacactggct ctgtcgtgtc ccaagtttcg gccggtgtct     1740
acgctaccgt ccggttcgat cagtatgaca ttcacaatct ccgtactatc gagaagactt     1800
ggtatgctcg ccatgcgacg ctgcataatg gcaagaagat ttctatcaac aatgtcacgg     1860
aaatggctcc aacatcccct atcaagacaa attgaggatc caaatcacca gtctctctct     1920
acaaatctat ctctctctat ttttctccag aataatgtgt gagtagttcc cagataaggg     1980
aattagggtt cttataggt ttcgctcatg tgttgagcat ataagaaacc cttagtatgt      2040
atttgtattt gtaaaatact tctatcaata aaatttctaa ttcctaaaac caaaatccag     2100
t                                                                     2101
```

<210> SEQ ID NO 55
<211> LENGTH: 1873
<212> TYPE: DNA
<213> ORGANISM: Artificial
<220> FEATURE:
<223> OTHER INFORMATION: Synthetic

<400> SEQUENCE: 55

```
ggtccgattg agacttttca acaaagggta atatccggaa acctcctcgg attccattgc      60
```

| | |
|---|---|
| ccagctatct gtcactttat tgtgaagata gtggaaaagg aaggtggctc ctacaaatgc | 120 |
| catcattgcg ataaaggaaa ggccatcgtt gaagatgcct ctgccgacag tggtcccaaa | 180 |
| gatggacccc cacccacgag gagcatcgtg aaaaagaag acgttccaac cacgtcttca | 240 |
| aagcaagtgg attgatgtga tggtccgatt gagactttc aacaaagggt aatatccgga | 300 |
| aacctcctcg gattccattg cccagctatc tgtcactta ttgtgaagat agtggaaaag | 360 |
| gaaggtggct cctacaaatg ccatcattgc gataaaggaa aggccatcgt tgaagatgcc | 420 |
| tctgccgaca gtggtcccaa agatggaccc ccacccacga ggagcatcgt ggaaaaagaa | 480 |
| gacgttccaa ccacgtcttc aaagcaagtg gattgatgtg atatctccac tgacgtaagg | 540 |
| gatgacgcac aatcccacta tccttcgcaa gacccttcct ctatataagg aagttcattt | 600 |
| catttggaga ggacacagaa acattcgcaa aaacaaaatc ccagtatcaa aattcttctc | 660 |
| ttttttcat atttcgcaaa gatttaaaaa gatctgctag aaataatttt gtttaacttt | 720 |
| aagaaggaga tatatccatg gctatcctag accttaagtc cctcgtgctg aacgccatta | 780 |
| actactgggg ccctaagaac aacaacggca tccagggcgg tgacttcggc taccccatct | 840 |
| ctgagaagca gatcgacact agcatcatta ccttcaccca ccctcgcttg atcccctacg | 900 |
| atcttactat cccgcagaac cttgagacca tcttcaccac aacgcaggtg ctcaccaata | 960 |
| acactgacct ccagcaatcc cagaccgtga gctttgcgaa gagaccact accacgacct | 1020 |
| caactagcac gaccaacggt tggacagaag gaggcaagat cagcgacacg ctggaggaga | 1080 |
| aagtttcggt tagcattccg ttcatcggtg agggtggcgg gaagaactcg actaccatag | 1140 |
| aggccaactt cgcacacaac tctagcacca ctaccttcca gcaagcaagc actgacattg | 1200 |
| agtggaacat tagccaaccg gtgctggttc ctccctctaa acaagttgtc gcgacccttg | 1260 |
| tgatcatggg aggcaacttt accatcccta tggacttgat gaccacgatt gatagtacag | 1320 |
| agcactactc ccactactcc ggttacccta tcctcacctg gatctcgtcc ccagataact | 1380 |
| cttactccgg tccctttatg tcatggtact ttgcaaactg gcctaacctt ccgagtggat | 1440 |
| tcggcccact gaatagtgat aacacggtca atacactgg ctctgtcgtg tcccaagttt | 1500 |
| cggccggtgt ctacgctacc gtccggttcg atcagtatga cattcacaat ctccgtacta | 1560 |
| tcgagaagac ttggtatgct cgccatgcga cgctgcataa tggcaagaag atttctatca | 1620 |
| acaatgtcac ggaaatggct ccaacatccc ctatcaagac aaattgagga tccaaatcac | 1680 |
| cagtctctct ctacaaatct atctctctct atttttctcc agaataatgt gtgagtagtt | 1740 |
| cccagataag ggaattaggg ttcttatagg gtttcgctca tgtgttgagc atataagaaa | 1800 |
| cccttagtat gtatttgtat ttgtaaaata cttctatcaa taaatttct aattcctaaa | 1860 |
| accaaaatcc agt | 1873 |

<210> SEQ ID NO 56
<211> LENGTH: 2870
<212> TYPE: DNA
<213> ORGANISM: Artificial
<220> FEATURE:
<223> OTHER INFORMATION: Synthetic

<400> SEQUENCE: 56

| | |
|---|---|
| gaagttgaag acaaaagaag gtcttaaatc ctggctagca acactgaact atgccagaaa | 60 |
| ccacatcaaa gatatgggca agcttcttgg cccattatat ccaaagacct cagagaaagg | 120 |
| tgagcgaagg ctcaattcag aagattggaa gctgatcaat aggatcaaga caatggtgag | 180 |
| aacgcttcca aatctcacta ttccaccaga agatgcatac attatcattg aaacagatgc | 240 |

```
atgtgcaact ggatggggag cagtatgcaa gtggaagaaa aacaaggcag acccaagaaa    300
tacagagcaa atctgtaggt atgccagtgg aaaatttgat aagccaaaag gaacctgtga    360
tgcagaaatc tatggggtta tgaatggctt agaaaagatg agattgttct acttggacaa    420
aagagagatc acagtcagaa ctgacagtag tgcaatcgaa aggttctaca acaagagtgc    480
tgaacacaag ccttctgaga tcagatggat caggttcatg gactacatca ctggtgcagg    540
accagagata gtcattgaac acataaaagg gaagagcaat ggtttagctg acatcttgtc    600
caggctcaaa gccaaattag ctcagaatga accaacggaa gagatgatcc tgcttacaca    660
agccataagg gaagtaattc cttatccaga tcatccatac actgagcaac tcagagaatg    720
gggaaacaaa attctggatc cattccccac attcaagaag gacatgttcg aaagaacaga    780
gcaagctttt atgctaacag aggaaccagt tctactctgt gcatgcagga agcctgcaat    840
tcagttagtg tccagaacat ctgccaaccc aggaaggaaa ttcttcaagt gcgcaatgaa    900
caaatgccat tgctggtact gggcagatct cattgaagaa cacattcaag acagaattga    960
tgaatttctc aagaatcttg aagttctgaa gaccggtggc gtgcaaacaa tggaggagga   1020
acttatgaag gaagtcacca agctgaagat agaagagcag gagttcgagg aataccaggc   1080
cacaccaagg gctatgtcgc cagtagccgc agaagatgtg ctagatctcc aagacgtaag   1140
caatgacgat tgaggaggca ttgacgtcag ggatgaccgc agcggagagt actgggccca   1200
ttcagtggat gctccactga gttgtattat tgtgtgcttt tcggacaagt gtgctgtcca   1260
cttctttttg gcacctgtgc cactttattc cttgtctgcc acgatgcctt tgcttagctt   1320
gtaagcaagg atcgcagtgc gtgtgtgaca ccacccccct tccgacgctc tgcctatata   1380
aggcaccgtc tgtaagctct tacgatcatc ggtagttcac caacacagaa acattcgcaa   1440
aaacaaaatc ccagtatcaa aattcttctc tttttttcat atttcgcaaa gaactagtga   1500
aacaatggct caagtgtcgc gcatctgtaa cggagttcag aaccctagcc tgatctctaa   1560
cttgagcaag tctagccagc gtaagtcacc attgagcgtg agcttgaaga ctcaacagca   1620
ccctagagcc tacccaataa gctctagttg gggactcaag aagtccggta tgactctgat   1680
tggatctgag ttacgtcctc tgaaagtgat gagttccgtt agtaccgctt gcatggctat   1740
cctagacctt aagtccctcg tgctgaacgc cattaactac tggggcccta agaacaacaa   1800
cggcatccag ggcggtgact tcggctaccc catctctgag aagcagatcg acactagcat   1860
cattaccttc acccaccctc gcttgatccc ctacgatctt actatcccgc agaaccttga   1920
gaccatcttc accacaacgc aggtgctcac caataacact gacctccagc aatcccagac   1980
cgtgagcttt gcgaagaaga ccactaccac gacctcaact agcacgacca acggttggac   2040
agaaggaggc aagatcagcg acacgctgga ggagaaagtt tcggttagca ttccgttcat   2100
cggtgagggt ggcgggaaga actcgactac catagaggcc aacttcgcac acaactctag   2160
caccactacc ttccagcaag caagcactga cattgagtgg aacattagcc aaccggtgct   2220
ggttcctccc tctaaacaag ttgtcgcgac ccttgtgatc atgggaggca actttaccat   2280
ccctatggac ttgatgacca cgattgatag tacagagcac tactcccact actccggtta   2340
ccctatcctc acctggatct cgtccccaga taactcttac tccggtccct ttatgtcatg   2400
gtactttgca aactggccta accttccgag tggattcggc ccactgaata gtgataacac   2460
ggtcacatac actggctctg tcgtgtccca agtttcggcc ggtgtctacg ctaccgtccg   2520
gttcgatcag tatgacattc acaatctccg tactatcgag aagacttggt atgctcgcca   2580
tgcgacgctg cataatggca agaagatttc tatcaacaat gtcacggaaa tggctccaac   2640
```

| | |
|---|---:|
| atcccctatc aagacaaatt gagtctagac aaatcaccag tctctctcta caaatctatc | 2700 |
| tctctctatt tttctccaga ataatgtgtg agtagttccc agataaggga attagggttc | 2760 |
| ttatagggtt tcgctcatgt gttgagcata aagaaaccc ttagtatgta tttgtatttg | 2820 |
| taaaatactt ctatcaataa aatttctaat tcctaaaacc aaaatccagt | 2870 |

<210> SEQ ID NO 57
<211> LENGTH: 2642
<212> TYPE: DNA
<213> ORGANISM: Artificial
<220> FEATURE:
<223> OTHER INFORMATION: Synthetic

<400> SEQUENCE: 57

| | |
|---|---:|
| gaagttgaag acaaaagaag gtcttaaatc ctggctagca acactgaact atgccagaaa | 60 |
| ccacatcaaa gatatgggca agcttcttgg cccattatat ccaaagacct cagagaaagg | 120 |
| tgagcgaagg ctcaattcag aagattggaa gctgatcaat aggatcaaga caatggtgag | 180 |
| aacgcttcca aatctcacta ttccaccaga agatgcatac attatcattg aaacagatgc | 240 |
| atgtgcaact ggatggggag cagtatgcaa gtggaagaaa acaaggcag acccaagaaa | 300 |
| tacagagcaa atctgtaggt atgccagtgg aaaatttgat aagccaaaag gaacctgtga | 360 |
| tgcagaaatc tatggggtta tgaatggctt agaaaagatg agattgttct acttggacaa | 420 |
| aagagagatc acagtcagaa ctgacagtag tgcaatcgaa aggttctaca caagagtgc | 480 |
| tgaacacaag ccttctgaga tcagatggat caggttcatg gactacatca ctggtgcagg | 540 |
| accagagata gtcattgaac acataaaagg gaagagcaat ggtttagctg acatcttgtc | 600 |
| caggctcaaa gccaaattag ctcagaatga accaacggaa gagatgatcc tgcttacaca | 660 |
| agccataagg gaagtaattc cttatccaga tcatccatac actgagcaac tcagagaatg | 720 |
| gggaaacaaa attctggatc cattccccac attcaagaag gacatgttcg aaagaacaga | 780 |
| gcaagctttt atgctaacag aggaaccagt tctactctgt gcatgcagga agcctgcaat | 840 |
| tcagttagtg tccagaacat ctgccaaccc aggaaggaaa ttcttcaagt gcgcaatgaa | 900 |
| caaatgccat tgctggtact gggcagatct cattgaagaa cacattcaag acagaattga | 960 |
| tgaatttctc aagaatcttg aagttctgaa gaccggtggc gtgcaaacaa tggaggagga | 1020 |
| acttatgaag gaagtcacca agctgaagat agaagagcag gagttcgagg aataccaggc | 1080 |
| cacaccaagg gctatgtcgc cagtagccgc agaagatgtg ctagatctcc aagacgtaag | 1140 |
| caatgacgat tgaggaggca ttgacgtcag ggatgaccgc agcggagagt actgggccca | 1200 |
| ttcagtggat gctccactga gttgtattat tgtgtgcttt tcggacaagt gtgctgtcca | 1260 |
| cttttctttg gcacctgtgc cactttattc cttgtctgcc acgatgcctt tgcttagctt | 1320 |
| gtaagcaagg atcgcagtgc gtgtgtgaca ccacccccct tccgacgctc tgcctatata | 1380 |
| aggcaccgtc tgtaagctct tacgatcatc ggtagttcac caacacagaa acattcgcaa | 1440 |
| aaacaaaatc ccagtatcaa aattcttctc tttttttcat atttcgcaaa gaactagtga | 1500 |
| aacaatggct atcctagacc ttaagtccct cgtgctgaac gccattaact actggggccc | 1560 |
| taagaacaac aacggcatcc agggcggtga cttcggctac cccatctctg agaagcagat | 1620 |
| cgacactagc atcattacct tcacccaccc tcgcttgatc ccctacgatc ttactatccc | 1680 |
| gcagaacctt gagaccatct tcaccacaac gcaggtgctc accaataaca ctgacctcca | 1740 |
| gcaatcccag accgtgagct ttgcgaagaa gaccactacc acgacctcaa ctagcacgac | 1800 |
| caacggttgg acagaaggag gcaagatcag cgacacgctg gaggagaaag tttcggttag | 1860 |

```
cattccgttc atcggtgagg gtggcgggaa gaactcgact accatagagg ccaacttcgc   1920
acacaactct agcaccacta ccttccagca agcaagcact gacattgagt ggaacattag   1980
ccaaccggtg ctggttcctc cctctaaaca agttgtcgcg acccttgtga tcatgggagg   2040
caactttacc atccctatgg acttgatgac cacgattgat agtacagagc actactccca   2100
ctactccggt tacccctatcc tcacctggat ctcgtcccca gataactctt actccggtcc   2160
ctttatgtca tggtactttg caaactggcc taaccttccg agtggattcg gcccactgaa   2220
tagtgataac acggtcacat acactggctc tgtcgtgtcc caagtttcgg ccggtgtcta   2280
cgctaccgtc cggttcgatc agtatgacat tcacaatctc cgtactatcg agaagacttg   2340
gtatgctcgc catgcgacgc tgcataatgg caagaagatt tctatcaaca atgtcacgga   2400
aatggctcca acatccccta tcaagacaaa ttgagtctag acaaatcacc agtctctctc   2460
tacaaatcta tctctctcta tttttctcca gaataatgtg tgagtagttc ccagataagg   2520
gaattagggt tcttataggg tttcgctcat gtgttgagca tataagaaac ccttagtatg   2580
tatttgtatt tgtaaaatac ttctatcaat aaaatttcta attcctaaaa ccaaaatcca   2640
gt                                                                  2642

<210> SEQ ID NO 58
<211> LENGTH: 930
<212> TYPE: DNA
<213> ORGANISM: Bacillus thuringiensis
<220> FEATURE:
<221> NAME/KEY: misc_feature
<222> LOCATION: (1)..(930)
<223> OTHER INFORMATION: cry51Aa1 from NCBI Acc. No. DQ836184.
<220> FEATURE:
<221> NAME/KEY: misc_feature
<222> LOCATION: (1)..(930)
<223> OTHER INFORMATION: cry51Aa1 from NCBI Acc. No. DQ836184
<220> FEATURE:
<221> NAME/KEY: CDS
<222> LOCATION: (1)..(930)

<400> SEQUENCE: 58 atg att ttt ttg gca att tta gat tta aaa tct tta gta ctc aat gca    48
Met Ile Phe Leu Ala Ile Leu Asp Leu Lys Ser Leu Val Leu Asn Ala
1               5                   10                  15 ata aat tat tgg ggt cct aaa aat aat aat ggc ata cag ggt ggt gat    96
Ile Asn Tyr Trp Gly Pro Lys Asn Asn Asn Gly Ile Gln Gly Gly Asp
            20                  25                  30 ttt ggt tac cct ata tca gaa aaa caa ata gat acg tct att ata act   144
Phe Gly Tyr Pro Ile Ser Glu Lys Gln Ile Asp Thr Ser Ile Ile Thr
        35                  40                  45 tct act cat cct cgt tta att cca cat gat tta aca att cct caa aat   192
Ser Thr His Pro Arg Leu Ile Pro His Asp Leu Thr Ile Pro Gln Asn
    50                  55                  60 tta gaa act att ttt act aca act caa gta tta aca aat aat aca gat   240
Leu Glu Thr Ile Phe Thr Thr Thr Gln Val Leu Thr Asn Asn Thr Asp
65                  70                  75                  80 tta caa caa agt caa act gtt tct ttt gct aaa aaa aca acg aca aca   288
Leu Gln Gln Ser Gln Thr Val Ser Phe Ala Lys Lys Thr Thr Thr Thr
                85                  90                  95 act tca act tca act aca aat ggt tgg aca gaa ggt ggg aaa att tca   336
Thr Ser Thr Ser Thr Thr Asn Gly Trp Thr Glu Gly Gly Lys Ile Ser
            100                 105                 110 gat aca tta gaa gaa aaa gta agt gta tct att cct ttt att gga gag   384
Asp Thr Leu Glu Glu Lys Val Ser Val Ser Ile Pro Phe Ile Gly Glu
        115                 120                 125
```

```
gga gga gga aaa aac agt aca act ata gaa gct aat ttt gca cat aac      432
Gly Gly Gly Lys Asn Ser Thr Thr Ile Glu Ala Asn Phe Ala His Asn
        130                 135                 140 tct agt act act act ttt caa cag gct tca act gat ata gag tgg aat      480
Ser Ser Thr Thr Thr Phe Gln Gln Ala Ser Thr Asp Ile Glu Trp Asn
145                 150                 155                 160 att tca caa cca gta ttg gtt ccc cca cgt aaa caa gtt gta gca aca      528
Ile Ser Gln Pro Val Leu Val Pro Pro Arg Lys Gln Val Val Ala Thr
                165                 170                 175 tta gtt att atg gga ggt aat ttt act att cct atg gat ttg atg act      576
Leu Val Ile Met Gly Gly Asn Phe Thr Ile Pro Met Asp Leu Met Thr
            180                 185                 190 act ata gat tct aca gaa cat tat agt ggt tat cca ata tta aca tgg     624
Thr Ile Asp Ser Thr Glu His Tyr Ser Gly Tyr Pro Ile Leu Thr Trp
        195                 200                 205 ata tcg agc ccc gat aat agt tat aat ggt cca ttt atg agt tgg tat     672
Ile Ser Ser Pro Asp Asn Ser Tyr Asn Gly Pro Phe Met Ser Trp Tyr
    210                 215                 220 ttt gca aat tgg ccc aat tta cca tcg ggg ttt ggt cct tta aat tca     720
Phe Ala Asn Trp Pro Asn Leu Pro Ser Gly Phe Gly Pro Leu Asn Ser
225                 230                 235                 240 gat aat acg gtc act tat aca ggt tct gtt gta agt caa gta tca gct     768
Asp Asn Thr Val Thr Tyr Thr Gly Ser Val Val Ser Gln Val Ser Ala
                245                 250                 255 ggt gta tat gcc act gta cga ttt gat caa tat gat ata cac aat tta     816
Gly Val Tyr Ala Thr Val Arg Phe Asp Gln Tyr Asp Ile His Asn Leu
            260                 265                 270 agg aca att gaa aaa act tgg tat gca cga cat gca act ctt cat aat     864
Arg Thr Ile Glu Lys Thr Trp Tyr Ala Arg His Ala Thr Leu His Asn
        275                 280                 285 gga aag aaa ata tct ata aat aat gtt act gaa atg gca cca aca agt     912
Gly Lys Lys Ile Ser Ile Asn Asn Val Thr Glu Met Ala Pro Thr Ser
    290                 295                 300 cca ata aaa aca aat taa                                              930
Pro Ile Lys Thr Asn
305

<210> SEQ ID NO 59
<211> LENGTH: 309
<212> TYPE: PRT
<213> ORGANISM: Bacillus thuringiensis

<400> SEQUENCE: 59

Met Ile Phe Leu Ala Ile Leu Asp Leu Lys Ser Leu Val Leu Asn Ala
1               5                   10                  15

Ile Asn Tyr Trp Gly Pro Lys Asn Asn Gly Ile Gln Gly Gly Asp
            20                  25                  30

Phe Gly Tyr Pro Ile Ser Glu Lys Gln Ile Asp Thr Ser Ile Ile Thr
        35                  40                  45

Ser Thr His Pro Arg Leu Ile Pro His Asp Leu Thr Ile Pro Gln Asn
    50                  55                  60

Leu Glu Thr Ile Phe Thr Thr Thr Gln Val Leu Thr Asn Asn Thr Asp
65                  70                  75                  80

Leu Gln Gln Ser Gln Thr Val Ser Phe Ala Lys Lys Thr Thr Thr Thr
            85                  90                  95

Thr Ser Thr Ser Thr Thr Asn Gly Trp Thr Glu Gly Gly Lys Ile Ser
        100                 105                 110

Asp Thr Leu Glu Glu Lys Val Ser Val Ser Ile Pro Phe Ile Gly Glu
    115                 120                 125
```

```
Gly Gly Gly Lys Asn Ser Thr Thr Ile Glu Ala Asn Phe Ala His Asn
        130                 135                 140

Ser Ser Thr Thr Thr Phe Gln Gln Ala Ser Thr Asp Ile Glu Trp Asn
145                     150                 155                 160

Ile Ser Gln Pro Val Leu Val Pro Pro Arg Lys Gln Val Val Ala Thr
                165                 170                 175

Leu Val Ile Met Gly Gly Asn Phe Thr Ile Pro Met Asp Leu Met Thr
            180                 185                 190

Thr Ile Asp Ser Thr Glu His Tyr Ser Gly Tyr Pro Ile Leu Thr Trp
        195                 200                 205

Ile Ser Ser Pro Asp Asn Ser Tyr Asn Gly Pro Phe Met Ser Trp Tyr
    210                 215                 220

Phe Ala Asn Trp Pro Asn Leu Pro Ser Gly Phe Gly Pro Leu Asn Ser
225                 230                 235                 240

Asp Asn Thr Val Thr Tyr Thr Gly Ser Val Val Ser Gln Val Ser Ala
                245                 250                 255

Gly Val Tyr Ala Thr Val Arg Phe Asp Gln Tyr Asp Ile His Asn Leu
            260                 265                 270

Arg Thr Ile Glu Lys Thr Trp Tyr Ala Arg His Ala Thr Leu His Asn
        275                 280                 285

Gly Lys Lys Ile Ser Ile Asn Asn Val Thr Glu Met Ala Pro Thr Ser
    290                 295                 300

Pro Ile Lys Thr Asn
305
```